United States Patent [19]

Iwaki et al.

[11] Patent Number: 5,217,645
[45] Date of Patent: Jun. 8, 1993

[54] MESOMORPHIC COMPOUND, LIQUID CRYSTAL COMPOSITION, LIQUID CRYSTAL DEVICE, DISPLAY APPARATUS AND DISPLAY METHOD

[75] Inventors: Takashi Iwaki, Machida; Takao Takiguchi, Tokyo; Takeshi Togano, Yokohama; Yoko Yamada; Shinichi Nakamura, both of Atsugi, all of Japan

[73] Assignee: Canon Kabushiki Kaisha, Tokyo, Japan

[21] Appl. No.: 759,442

[22] Filed: Sep. 13, 1991

[30] Foreign Application Priority Data

Sep. 17, 1990 [JP] Japan .................. 2-243712

[51] Int. Cl.$^5$ .................. C09K 19/34; C07F 7/02; C07F 7/04; G02F 1/13
[52] U.S. Cl. .................. 252/299.61; 252/299.63; 252/299.01; 252/299.67; 252/299.16; 546/14; 546/284; 556/413; 556/416; 556/417; 556/418; 556/437; 556/438; 556/453; 556/454; 556/456; 359/103; 359/104
[58] Field of Search .................. 252/299.01, 299.61, 252/299.63, 299.66, 299.67; 544/229, 242, 298, 335; 546/14, 250, 268, 284, 314; 556/413, 416, 417, 418, 437, 438, 453, 454, 456; 359/103, 104

[56] References Cited

U.S. PATENT DOCUMENTS

| | | | |
|---|---|---|---|
| 4,367,924 | 1/1983 | Clark et al. | 359/17 |
| 4,678,283 | 7/1987 | Kreuzer et al. | 252/299.4 |
| 4,730,904 | 3/1988 | Panluth et al. | 252/299.5 |
| 5,034,151 | 7/1991 | Shinjo et al. | 252/299.61 |

FOREIGN PATENT DOCUMENTS 0355008 2/1990 European Pat. Off. .
56-107216 8/1981 Japan .

OTHER PUBLICATIONS

Schadt et al., "Applied Physics Letters", vol. 18, No. 4, p. 127 (1971).

Primary Examiner—Robert L. Stoll
Assistant Examiner—Shean C. Wu
Attorney, Agent, or Firm—Fitzpatrick, Cella, Harper & Scinto

[57] ABSTRACT

A mesomorphic compound represented by the following formula (I):

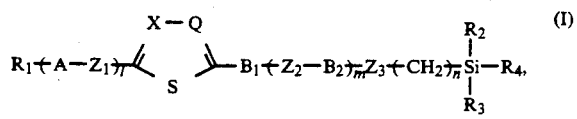

wherein $R_1$ denotes a linear or branched alkyl group having 2-16 carbon atoms capable of including one or non-neighboring two methylene groups which can be replaced with —O—, —S—, —CO—, —COO— or —OCO— and capable of including a hydrogen atom which can be replaced with a fluorine atom; A denotes —$A_1$— or —$A_1$—$A_2$—; $B_2$ denotes —$B_3$— or —$B_3$—$B_4$—; $A_1$, $A_2$, $B_1$, $B_3$ and $B_4$ independently denote

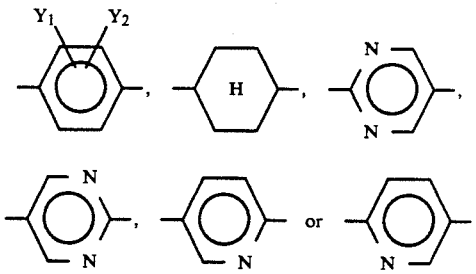

wherein $Y_1$ and $Y_2$ independently denote a hydrogen atom, F, Cl, Br, —$CH_3$, —CN or —$CF_3$, with the proviso that $B_1$ can be a single bond; $Z_1$ and $Z_2$ independently denote a single bond, —COO—, —OCO—, —$CH_2O$— or —$OCH_2$—; $Z_3$ denotes —O—, —CO—, —COO— or —OCO—; $R_2$, $R_3$ and $R_4$ independently denote a linear or branched alkyl group having 1—16 carbon atoms capable of including one or two methylene groups, other than those directly connected to Si, which can be replaced with —O—, —COO— or —OCO— with the proviso that —O— cannot directly be connected to —O—; l and m independently denote 0 or 1 with the proviso that $l+m \neq 0$; n is an integer of 1-12; and X and Q independently denote CH or N with the proviso that X and Q cannot be N simultaneously. The mesomorphic compound is effective for providing a ferroelectric liquid crystal composition showing an improved low-temperature operation characteristic and a decreased temperature-dependence of response speed.

40 Claims, 4 Drawing Sheets

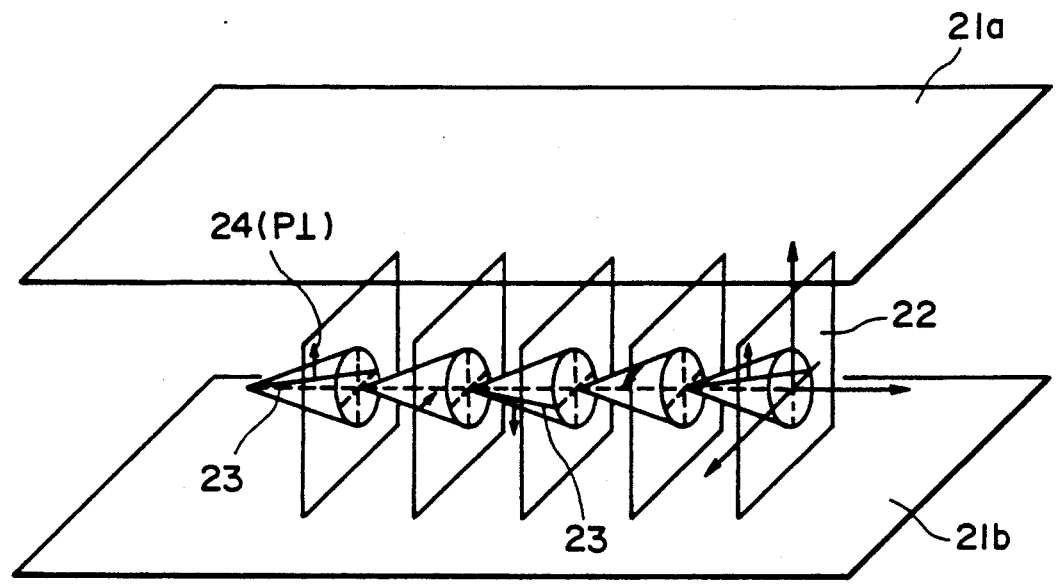
F I G. 2
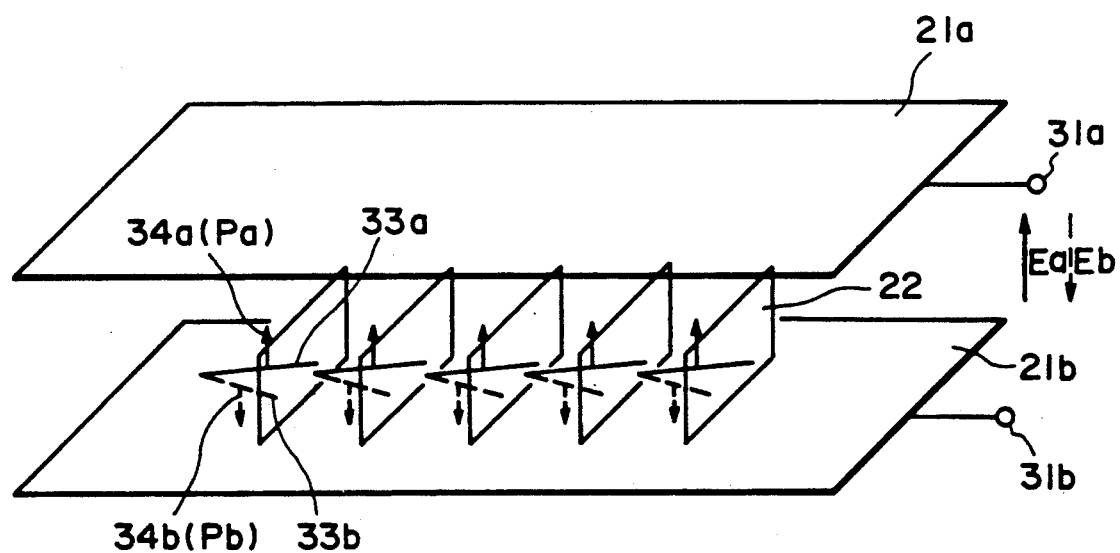
F I G. 3

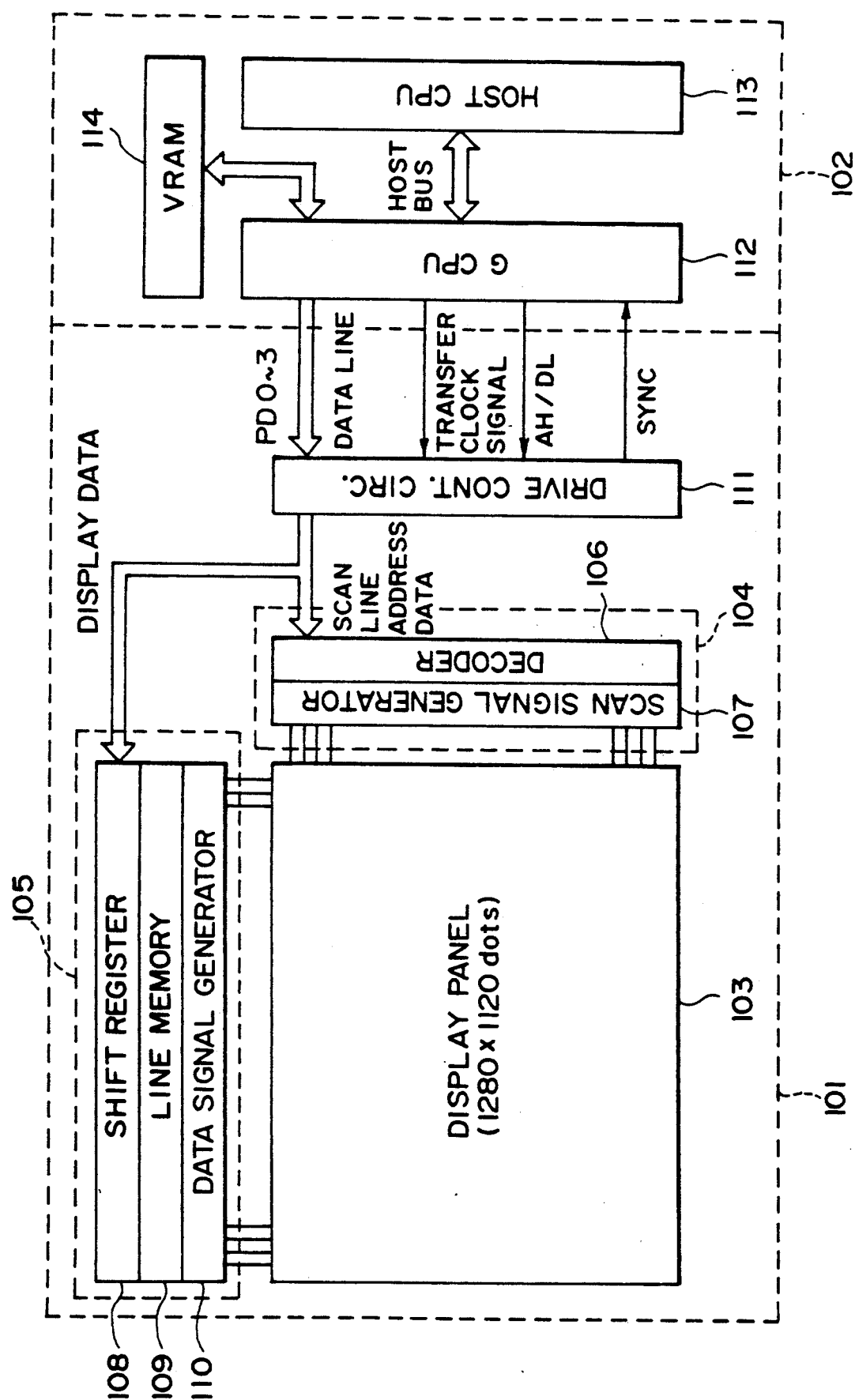
F I G. 4

MESOMORPHIC COMPOUND, LIQUID CRYSTAL COMPOSITION, LIQUID CRYSTAL DEVICE, DISPLAY APPARATUS AND DISPLAY METHOD

FIELD OF THE INVENTION AND RELATED ART

The present invention relates to a novel mesomorphic compound, a liquid crystal composition, a liquid crystal device, a display apparatus and a display method, and more particularly to a novel mesomorphic compound and a liquid crystal composition with improved responsiveness to an electric field, a liquid crystal device using the liquid crystal composition for use in a display device, a liquid crystal-optical shutter, etc., a display apparatus using the device, and a display method using the composition and device.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of milli-seconds, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected (or regions where a scanning electrode is not selected and a signal electrode is selected), which regions are called "half-selected points". If the difference between a voltage applied to the selected points and a voltage applied to the halfselected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. This leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed. However, any method is not sufficient to overcome the above-mentioned drawbacks. As a result, the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216; U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, previous ferroelectric liquid crystal materials do not sufficiently satisfy characteristics required for a liquid crystal device including low-temperature operation characteristic, high-speed responsiveness, etc. Among a response time $\tau$, the magnitude of spontaneous polarization Ps and viscosity $\eta$, the following relationship exists: $\tau = \eta/(Ps \cdot E)$, where E is an applied voltage. Accordingly, a high response speed can be obtained by (a) increasing the spontaneous polarization Ps, (b) lowering the viscosity $\eta$, or (c) increasing the applied voltage E. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Moreover, if it is assumed that the operation temperature of an actual display device is 5°–40° C., the response speed changes by a factor of about 20, so that it actually exceeds the range controllable by driving voltage and frequency.

Thus, as described hereinabove, commercialization of a ferroelectric liquid crystal device requires a liquid crystal composition assuming a chiral smectic phase which has not only a large spontaneous polarization but also a low viscosity, a high-speed responsiveness and a small temperature-dependence of response speed.

SUMMARY OF THE INVENTION

An object of the present invention is to provide a mesomorphic compound, a liquid crystal composition, particularly a chiral smectic liquid crystal composition, containing the mesomorphic compound for providing a practical ferroelectric liquid crystal device, a liquid crystal device using the liquid crystal composition and having a high response speed and a smaller temperature-dependence of the response speed, a display apparatus using the device, and a display method using the composition and device.

According to the present invention, there is provided a mesomorphic compound represented by the following formula (I):

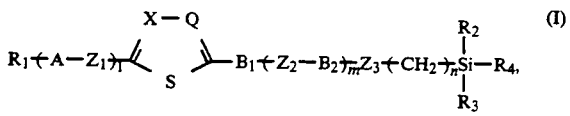

wherein $R_1$ denotes a linear or branched alkyl group having 2-16 carbon atoms capable of including one or non-neighboring two methylene groups which can be replaced with —O—, —S—, —CO—, —COO— or —OCO— and capable of including a hydrogen atom which can be replaced with a fluorine atom; A denotes —$A_1$— or —$A_1$—$A_2$; $B_2$ denotes —$B_3$— or —$B_3$—$B_4$—; $A_1$, $A_2$, $B_1$, $B_3$ and $B_4$ independently denote

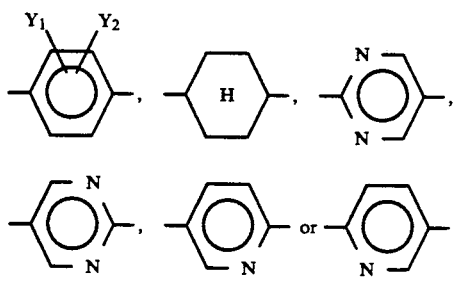

wherein $Y_1$ and $Y_2$ independently denote a hydrogen atom, F, Cl, Br, —$CH_3$, —CN or —$CF_3$, with the proviso that $B_1$ can be a single bond; $Z_1$ and $Z_2$ independently denote a single bond, —COO—, —OCO—, —$CH_2O$— or —$OCH_2$—; $Z_3$ denotes —O—, —CO—, —COO— or —OCO—; $R_2$, $R_3$ and $R_4$ independently denote a linear or branched alkyl group having 1-16 carbon atoms capable of including one or two methylene groups, other than those directly connected to Si, which can be replaced with —O—, —COO— or —OCO— with the proviso that —O— cannot directly be connected to —O—; l and m independently denote 0 or 1 with the proviso that $1+m \neq 0$; n is an integer of 1-12; and X and Q independently denote CH or N with the proviso that X and Q cannot be N simultaneously.

According to the present invention, there is further provided a liquid crystal composition containing at least one species of the mesomorphic compound as described above.

The present invention provides a liquid crystal device comprising a pair of electrode plates and the liquid crystal composition described above disposed between the electrode plates.

The present invention further provides a display apparatus comprising the liquid crystal device, and voltage application means for driving the liquid crystal device.

The present invention still further provides a display method using the liquid crystal composition or the liquid crystal device described above and switching the alignment direction of liquid crystal molecules by applying voltages to the liquid crystal composition to effect display.

We have accomplished the present invention based on a discovery of the compounds of the formula (I) containing thiophene or thiazole ring and containing a terminal trialkylsilylalkyl group. More specifically, we found that the compound represented by the formula (I) according to the present invention had a lower melting point and a wider temperature range of a mesomorphic phase compared with the conventional mesomorphic compounds. We also found that a liquid crystal device using a liquid crystal composition containing the above compound of the invention showed a good alignment characteristic, an improved response speed, a decreased temperature-dependence of response speed and a good display characteristic.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIGS. 2 and 3 are schematic perspective views of a device cell embodiment for illustrating the operation principle of a liquid crystal device utilizing ferroelectricity of a liquid crystal composition;

FIG. 4 is a block diagram showing a display apparatus comprising a liquid crystal device utilizing ferroelectricity of a liquid crystal composition and a graphic controller.

DETAILED DESCRIPTION OF THE INVENTION

Figure 1:
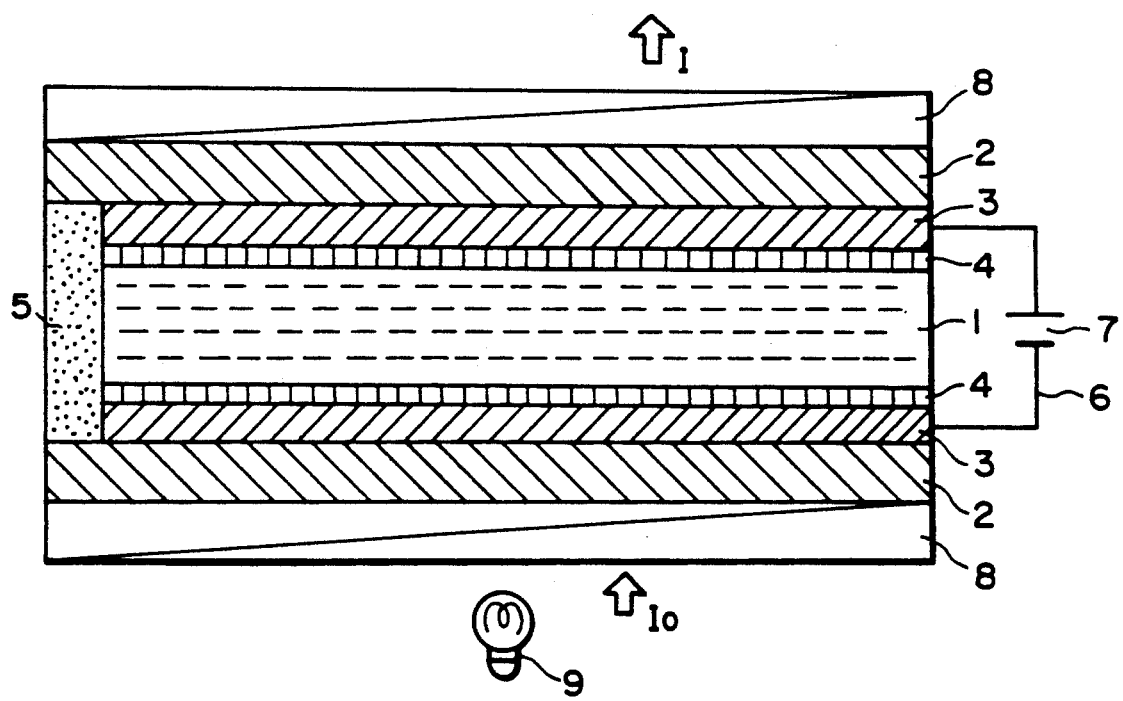
FIG. 1 is a schematic sectional view of a liquid crystal display device using a liquid crystal composition assuming a chiral smectic phase.

In the formula (I) as described above, preferred examples of $R_1$ may include alkyl, alkoxy, alkanoyloxy and alkoxycarbonyl groups.

Preferred examples of $A_1$, $A_2$, $B_1$, $B_2$ and $B_4$ each may include

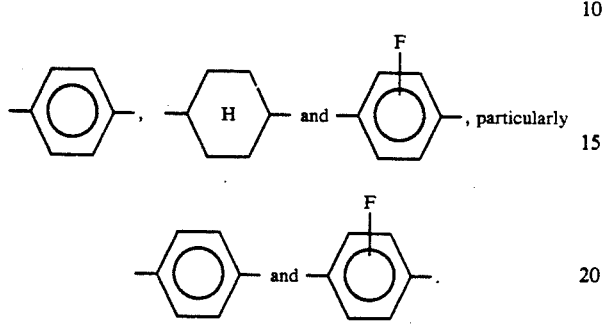

Further, $R_2$, $R_3$ and $R_4$ each may include an alkyl group having 1-12 carbon atoms, preferably a linear alkyl group having 1-8 carbon atoms. Particularly, at least two groups of $R_2$, $R_3$ and $R_4$ may preferably be methyl group.

The mesomorphic compounds represented by the general formula (I) may be synthesized through the following reaction schemes (A) and (B).

Scheme (A)
(Case where m = 1)

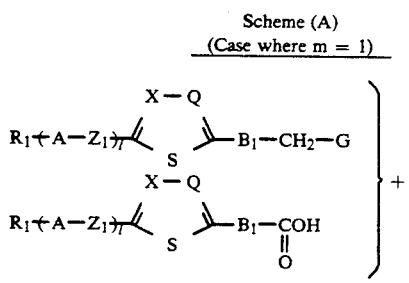

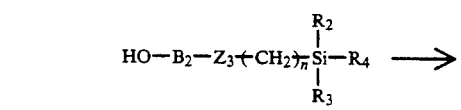

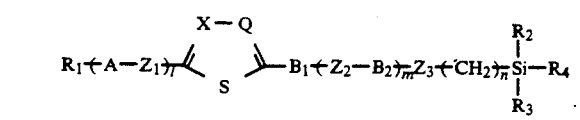

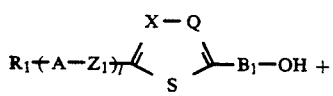

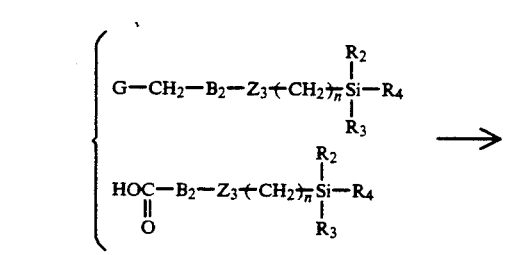

Scheme (A) -continued
(Case where m = 1)

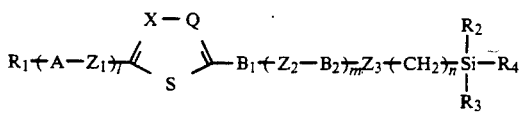

Scheme (B)
(Case where m = 1)

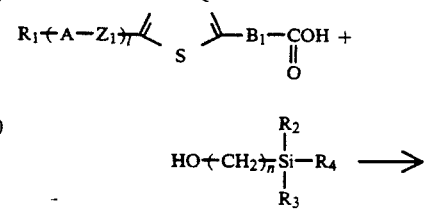

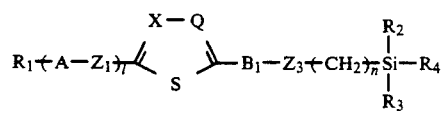

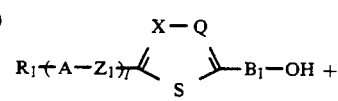

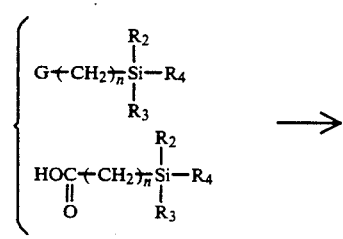

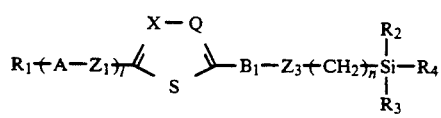

In the schemes (A) and (B), G denotes halogen or

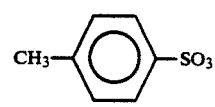

structure.
Further,

group can be introduced finally in the following manner.

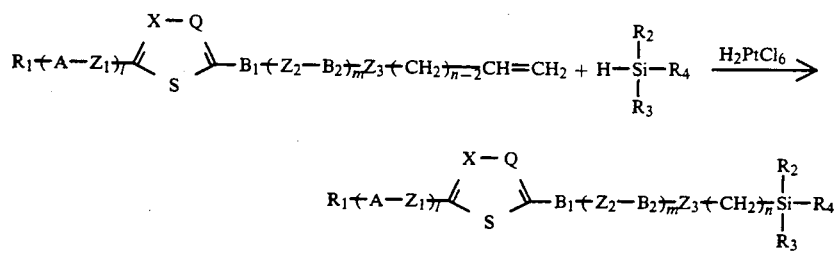
In the above, $R_1$, $R_2$, $R_3$, $R_4$, A, $B_1$, $B_2$, $A_1$, $Z_2$, $Z_3$, l, m, n, X and Q are the same as defined in the formula (I).
Specific examples of the mesomorphic compounds represented by the above-mentioned general formula (I) may include those shown by the following structural formulae.
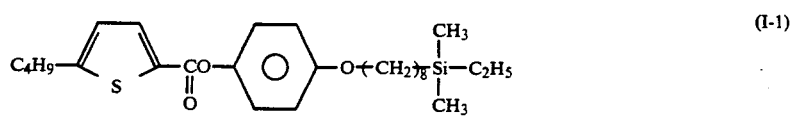
(I-1)
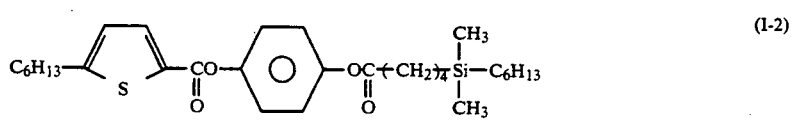
(I-2)
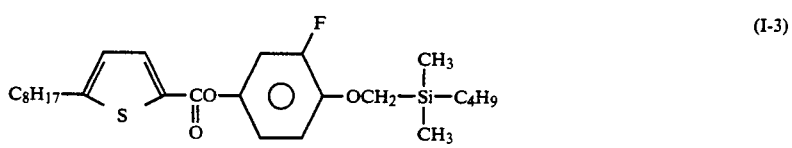
(I-3)
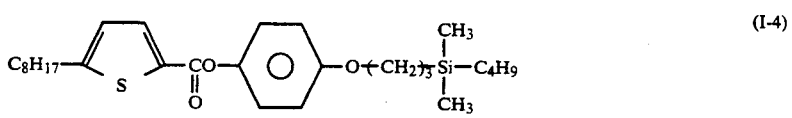
(I-4)
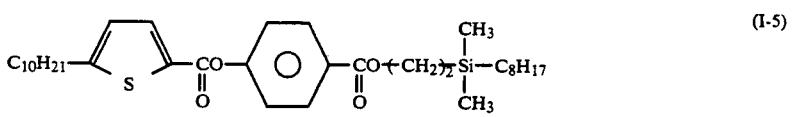
(I-5)
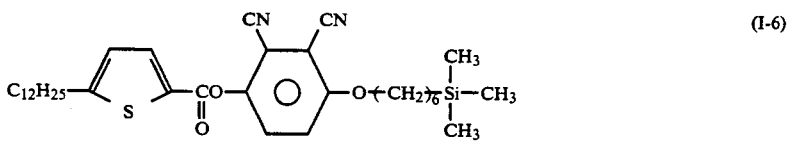
(I-6)
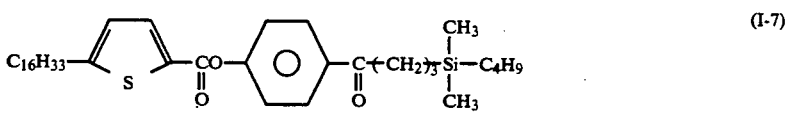
(I-7)
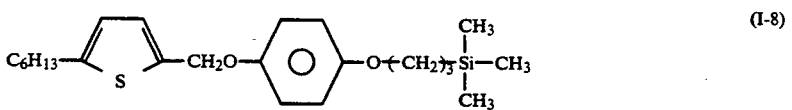
(I-8)
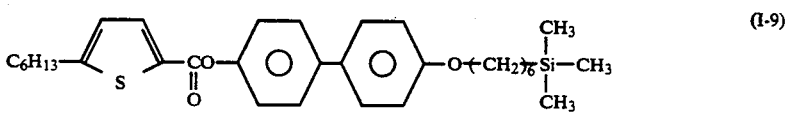
(I-9)
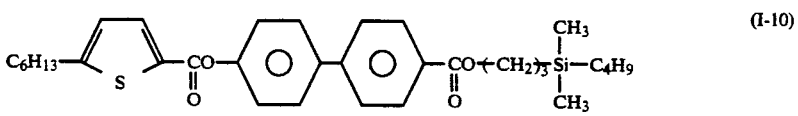
(I-10)

-continued
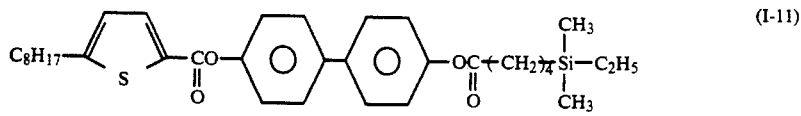
(I-11)
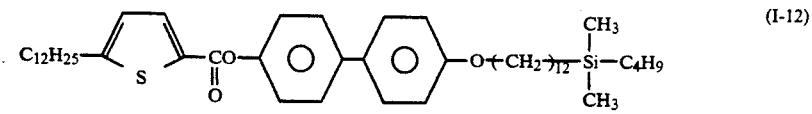
(I-12)
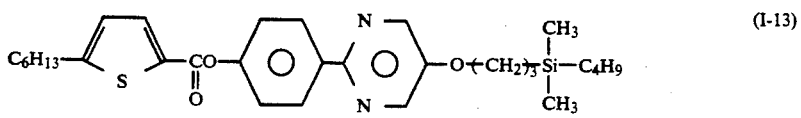
(I-13)
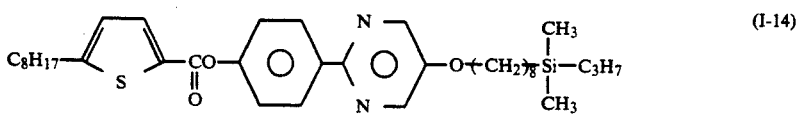
(I-14)
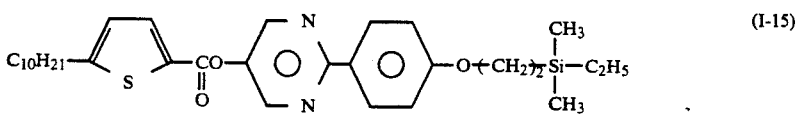
(I-15)
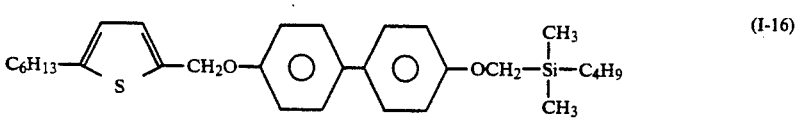
(I-16)
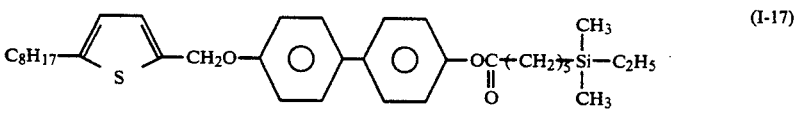
(I-17)
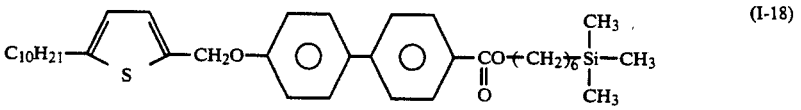
(I-18)
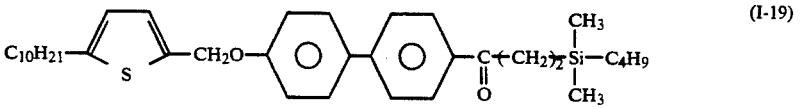
(I-19)
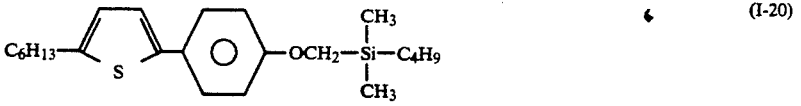
(I-20)
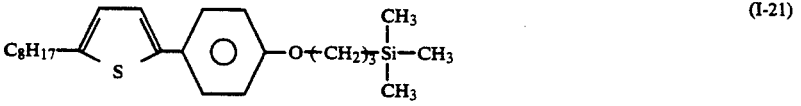
(I-21)
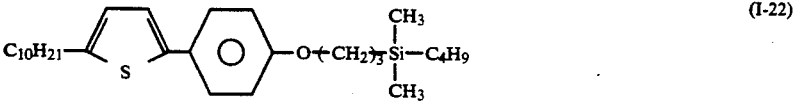
(I-22)
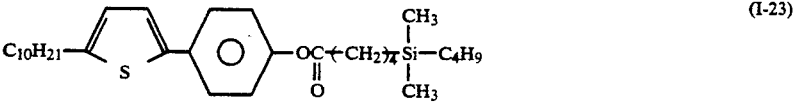
(I-23)

-continued
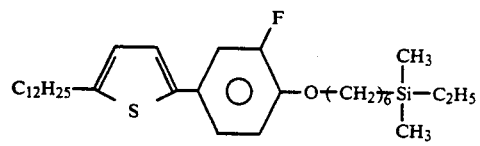 (I-24)
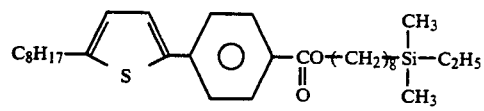 (I-25)
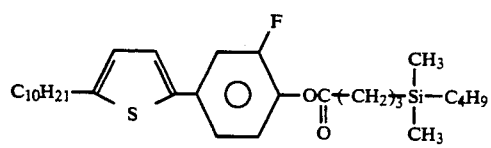 (I-26)
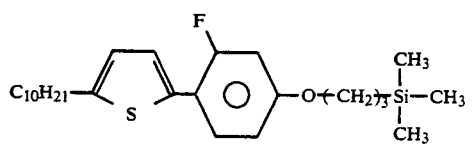 (I-27)
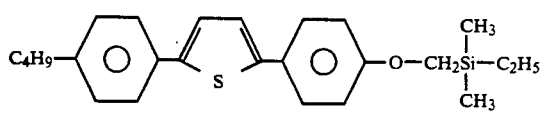 (I-28)
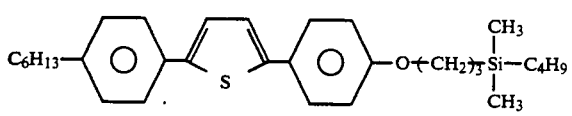 (I-29)
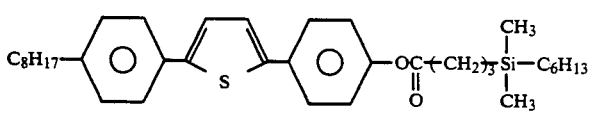 (I-30)
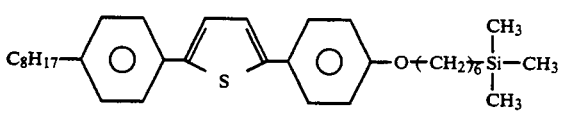 (I-31)
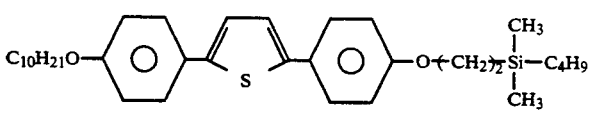 (I-32)
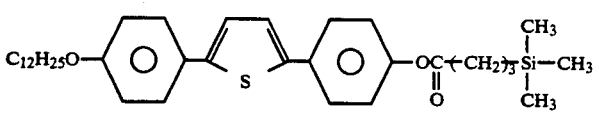 (I-33)
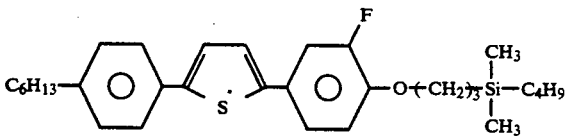 (I-34)
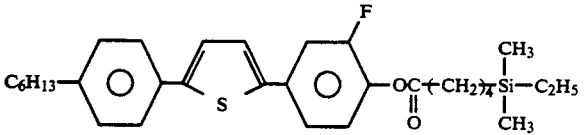 (I-35)

-continued
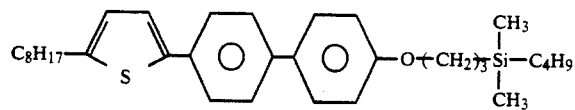 (I-36)
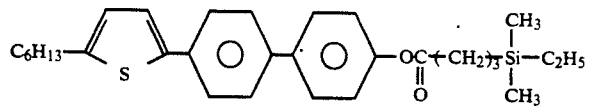 (I-37)
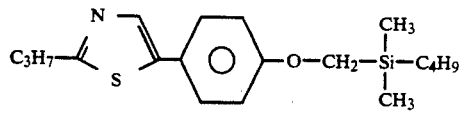 (I-38)
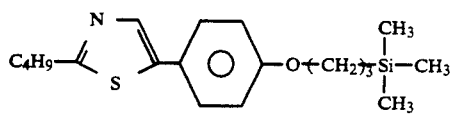 (I-39)
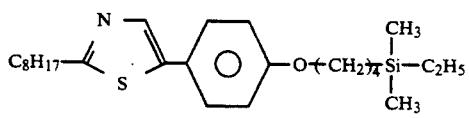 (I-40)
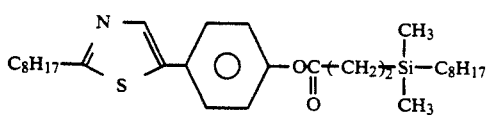 (I-41)
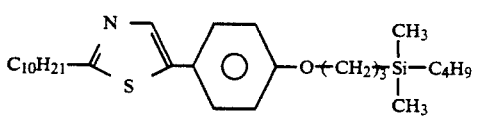 (I-42)
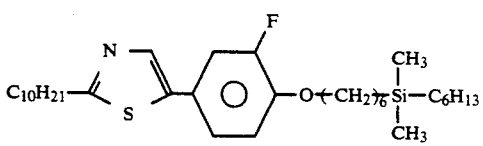 (I-43)
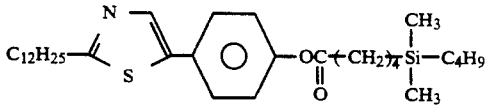 (I-44)
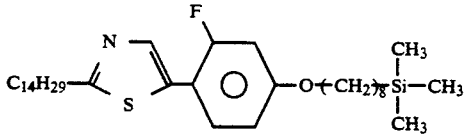 (I-45)
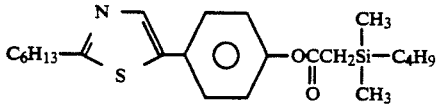 (I-46)
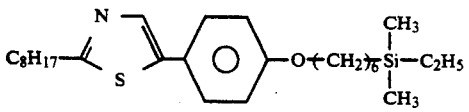 (I-47)
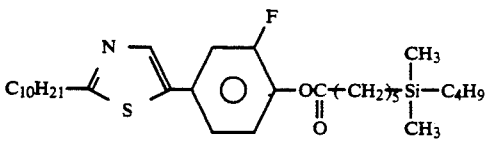 (I-48)

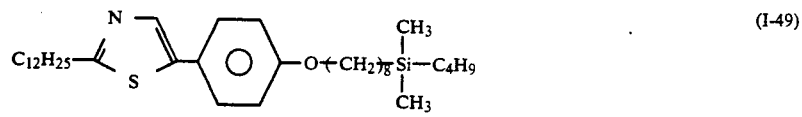 (I-49)
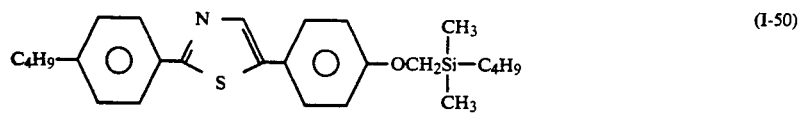 (I-50)
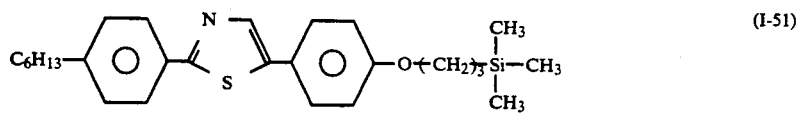 (I-51)
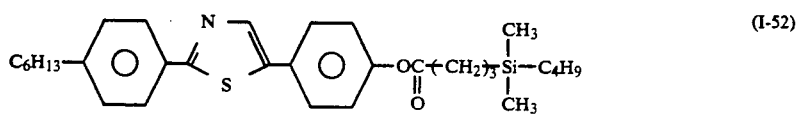 (I-52)
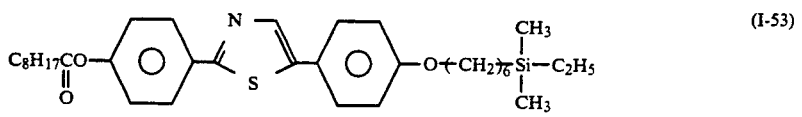 (I-53)
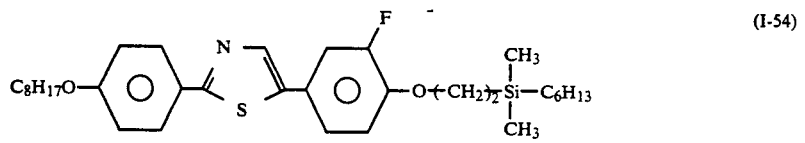 (I-54)
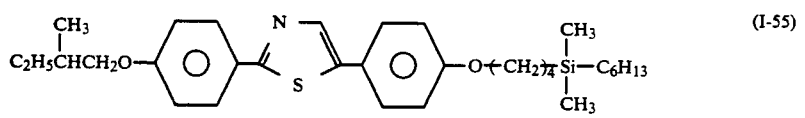 (I-55)
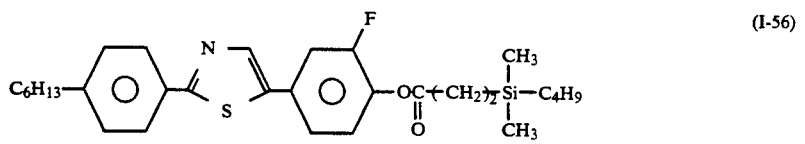 (I-56)
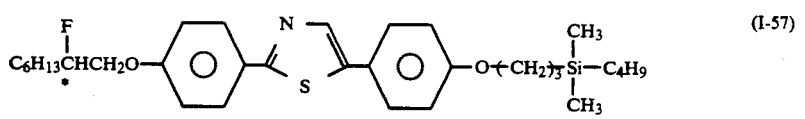 (I-57)
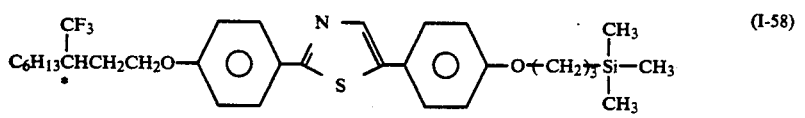 (I-58)
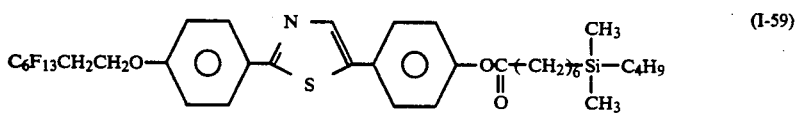 (I-59)
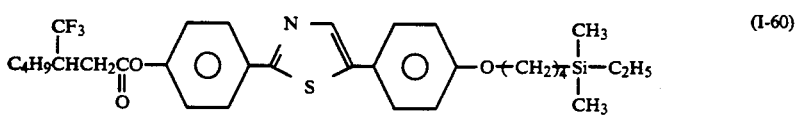 (I-60)

-continued
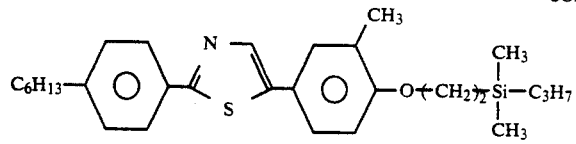
(I-61)
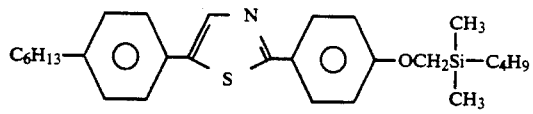
(I-62)
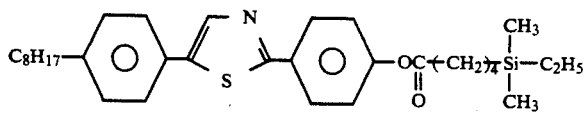
(I-63)
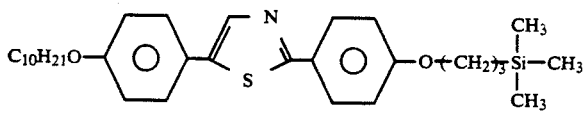
(I-64)
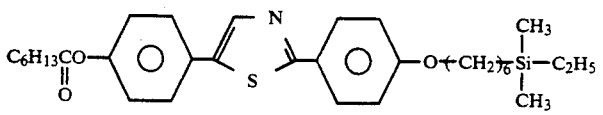
(I-65)
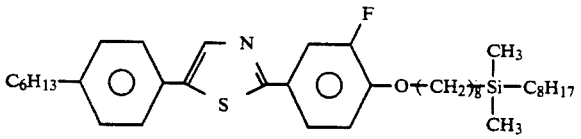
(I-66)
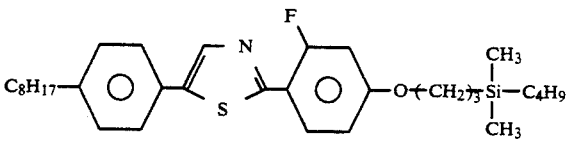
(I-67)
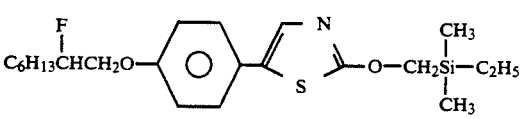
(I-68)
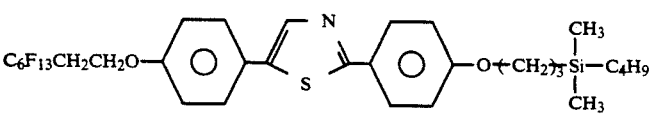
(I-69)
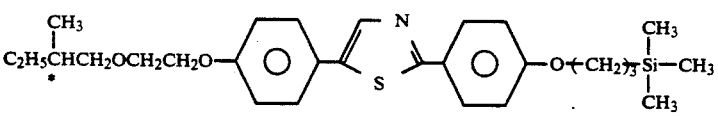
(I-70)
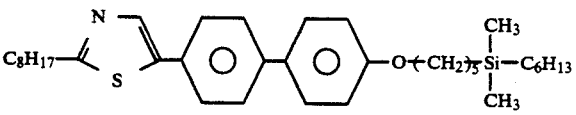
(I-71)
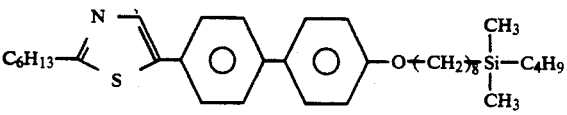
(I-72)
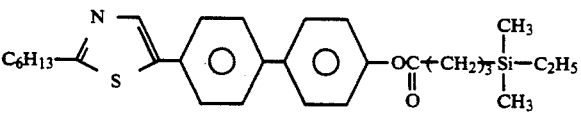
(I-73)

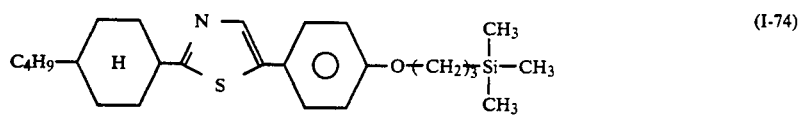 (I-74)
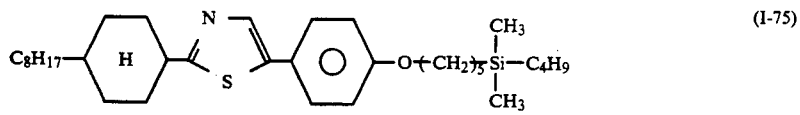 (I-75)
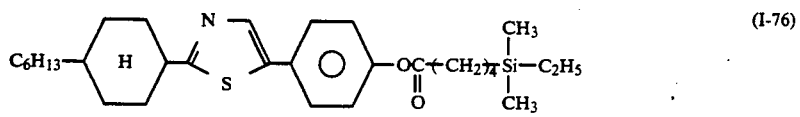 (I-76)
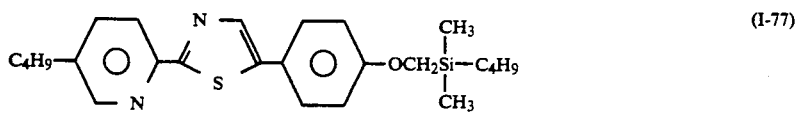 (I-77)
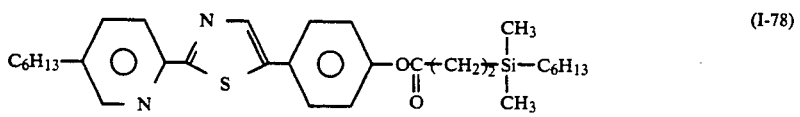 (I-78)
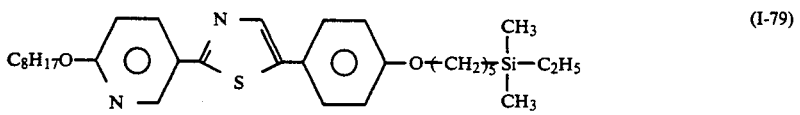 (I-79)
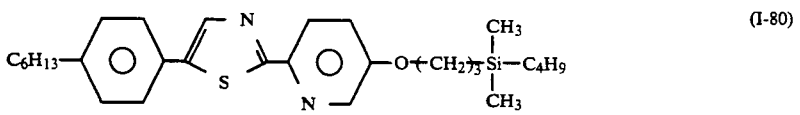 (I-80)
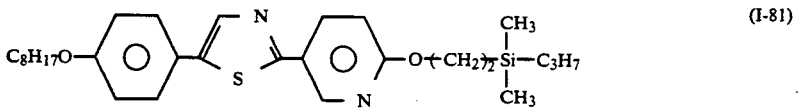 (I-81)
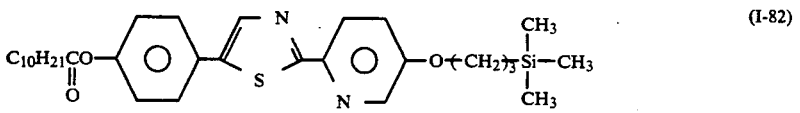 (I-82)
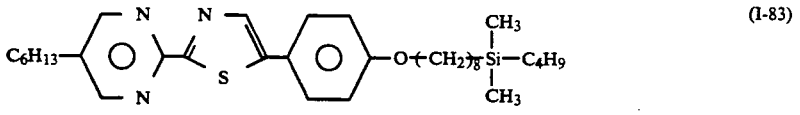 (I-83)
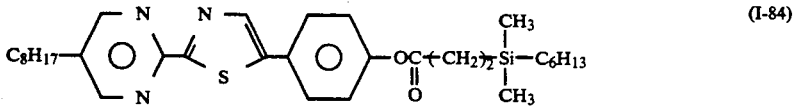 (I-84)
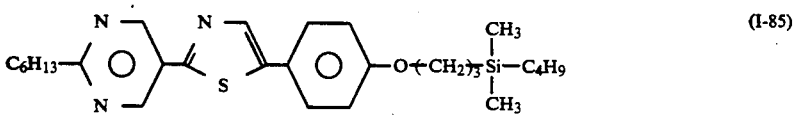 (I-85)
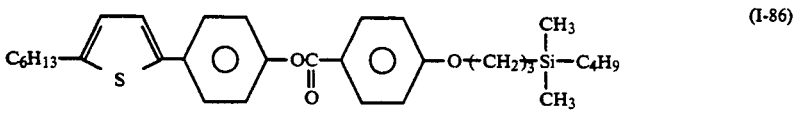 (I-86)

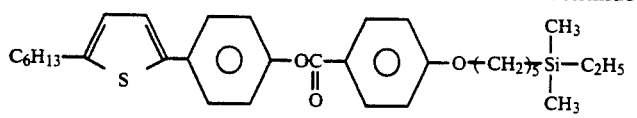 (I-87)
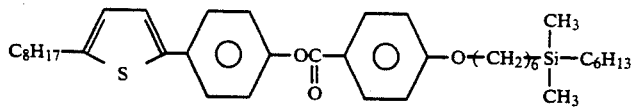 (I-88)
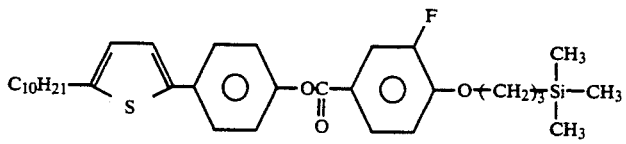 (I-89)
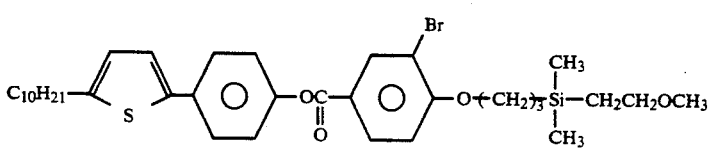 (I-90)
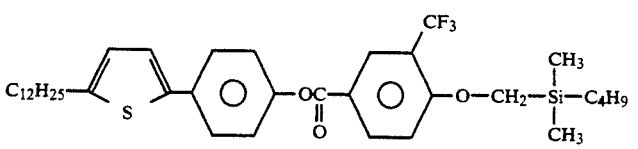 (I-91)
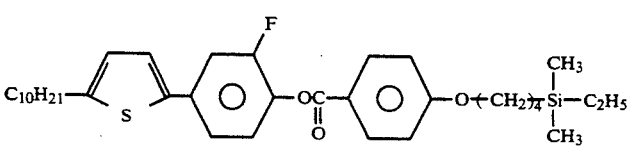 (I-92)
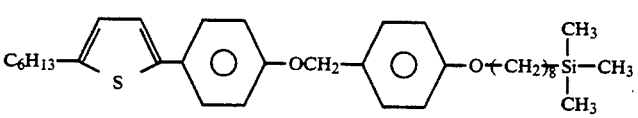 (I-93)
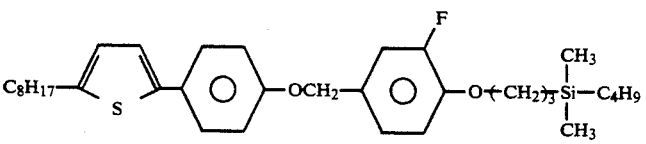 (I-94)
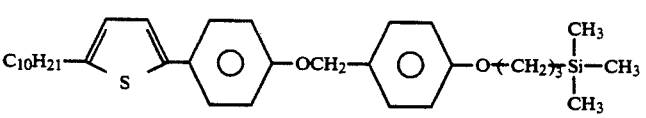 (I-95)
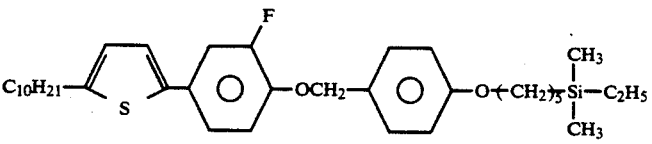 (I-96)
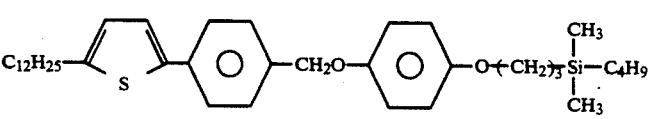 (I-97)
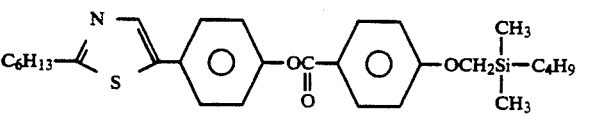 (I-98)

-continued
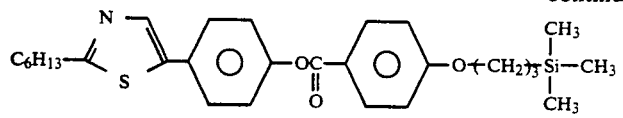  (I-99)
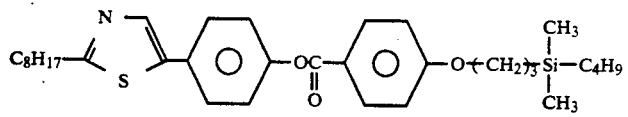  (I-100)
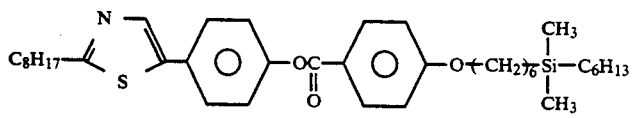  (I-101)
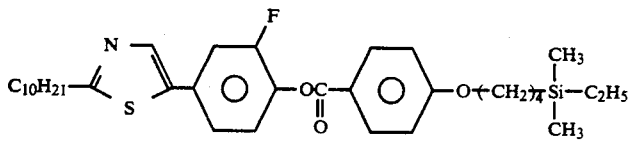  (I-102)
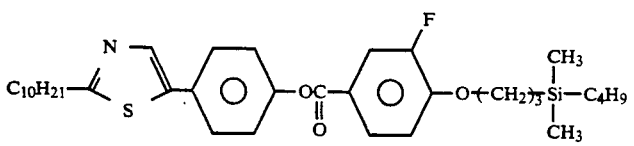  (I-103)
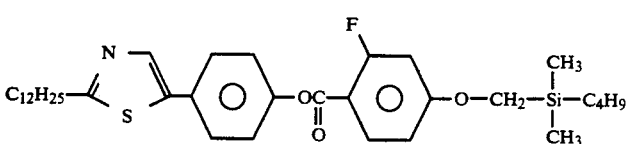  (I-104)
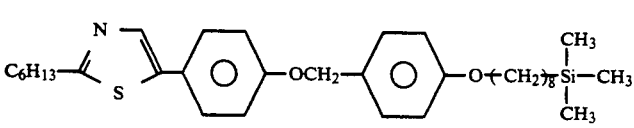  (I-105)
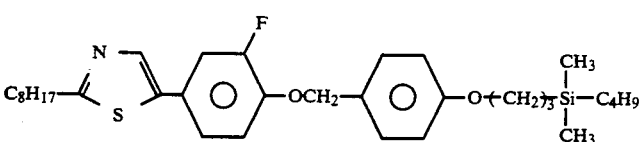  (I-106)
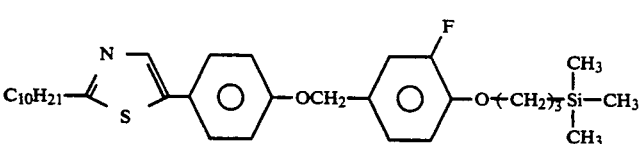  (I-107)
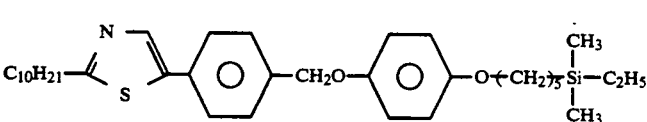  (I-108)
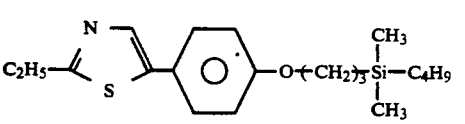  (I-109)
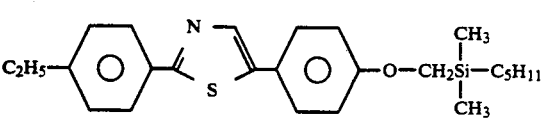  (I-110)

-continued
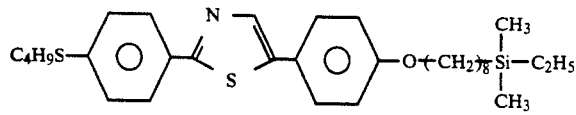 (I-111)
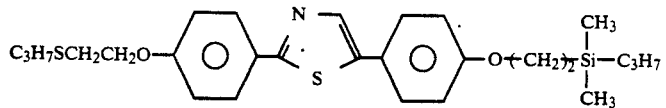 (I-112)
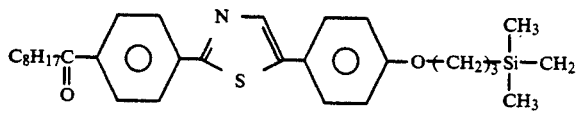 (I-113)
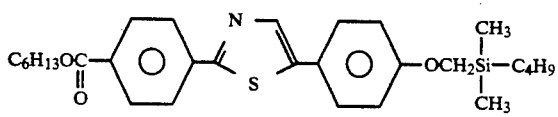 (I-114)
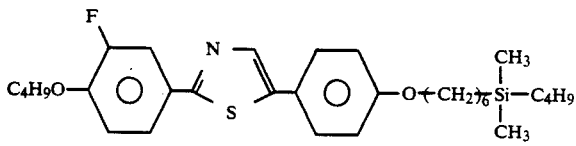 (I-115)
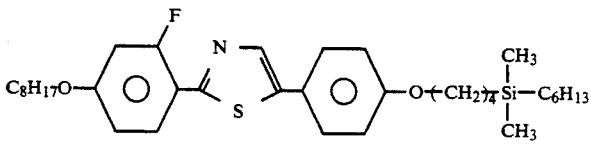 (I-116)
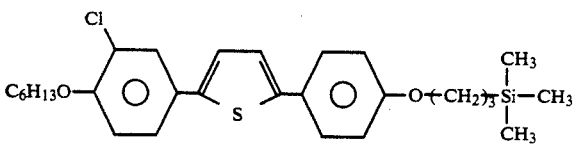 (I-117)
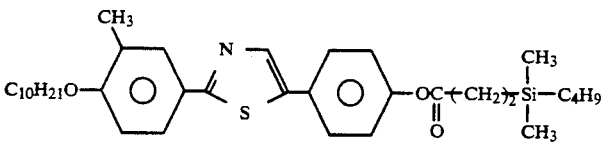 (I-118)
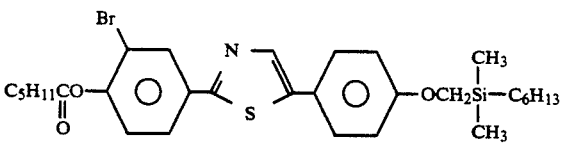 (I-119)
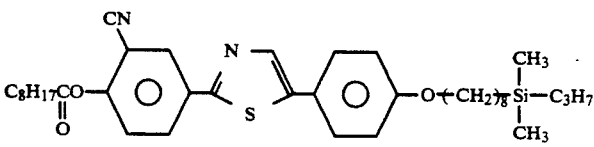 (I-120)
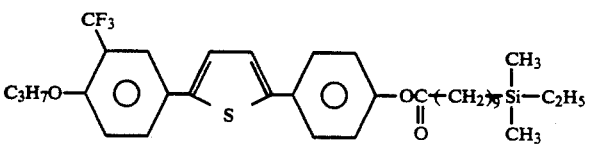 (I-121)
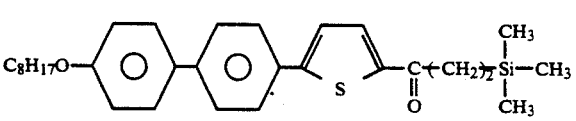 (I-122)

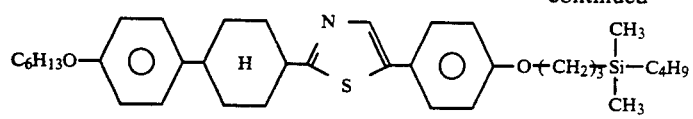 (I-123)
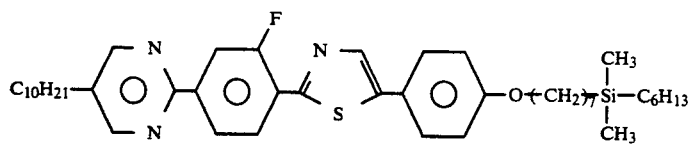 (I-124)
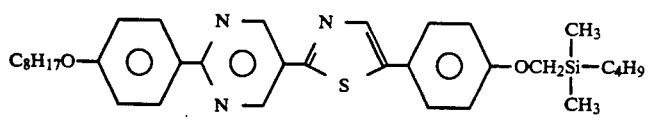 (I-125)
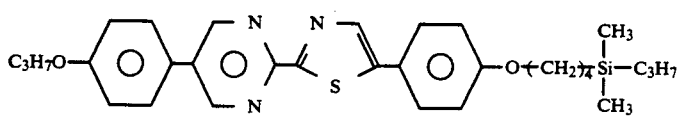 (I-126)
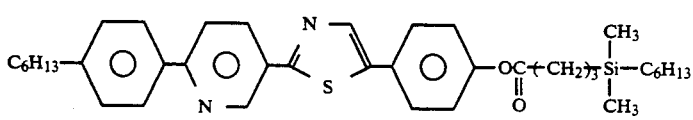 (I-127)
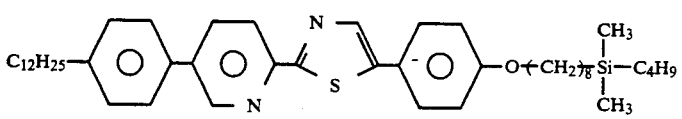 (I-128)
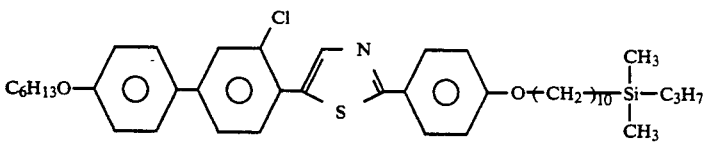 (I-129)
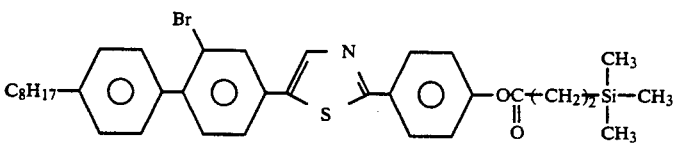 (I-130)
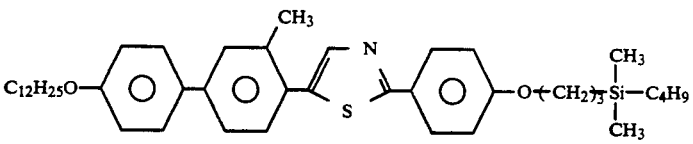 (I-131)
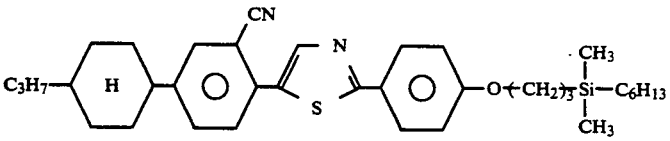 (I-132)
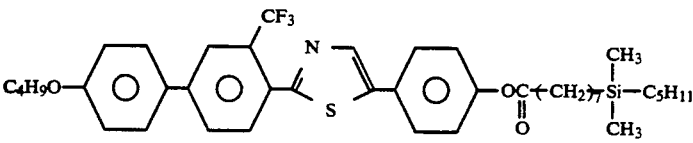 (I-133)
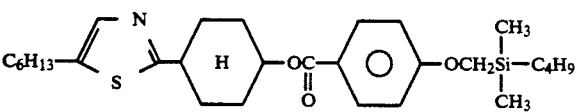 (I-134)

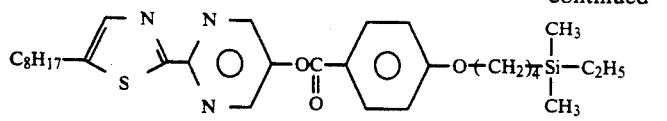 (I-135)
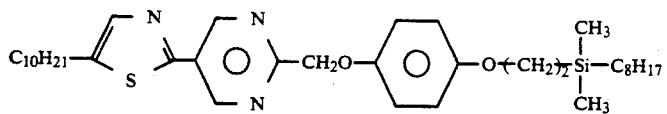 (I-136)
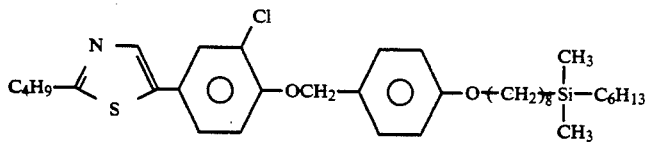 (I-137)
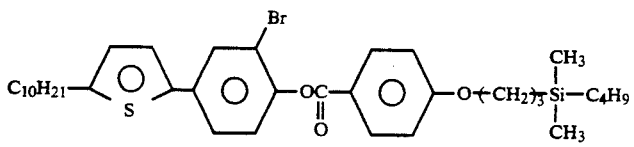 (I-138)
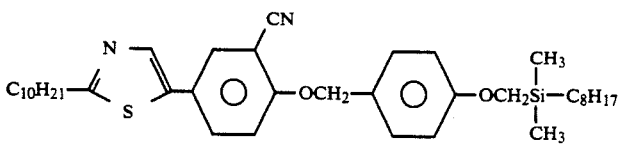 (I-139)
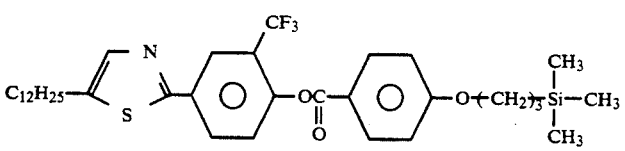 (I-140)
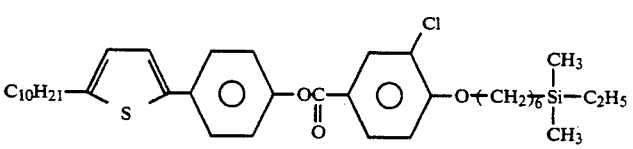 (I-141)
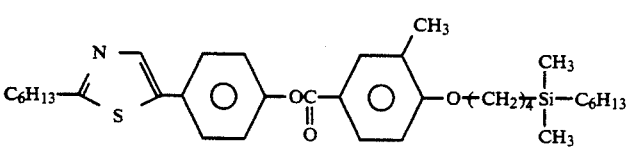 (I-142)
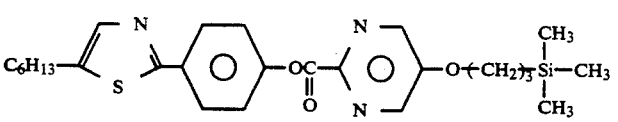 (I-143)
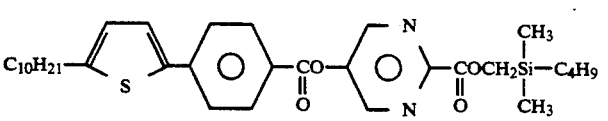 (I-144)
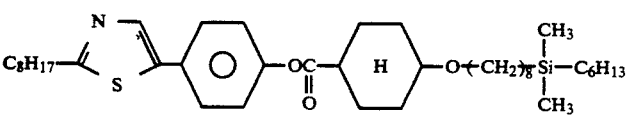 (I-145)
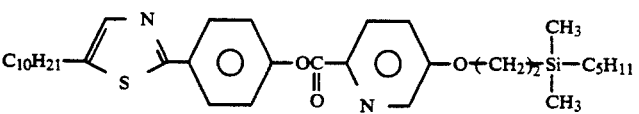 (I-146)

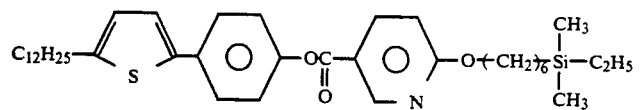
(I-147)
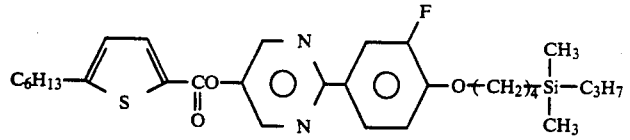
(I-148)
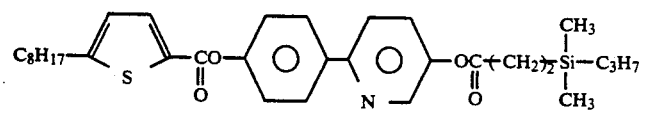
(I-149)
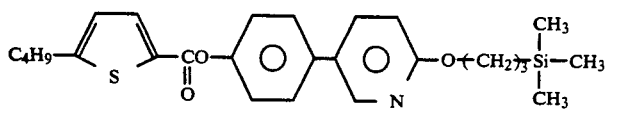
(I-150)
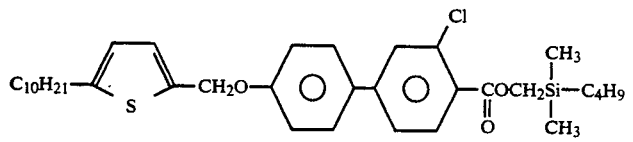
(I-151)
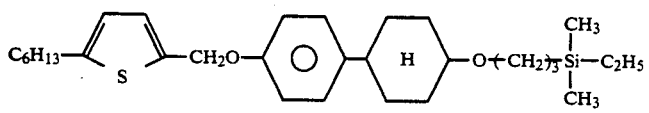
(I-152)
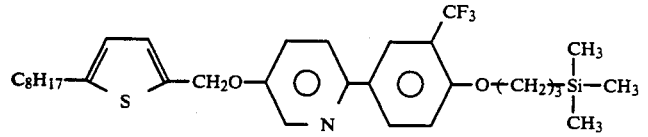
(I-153)
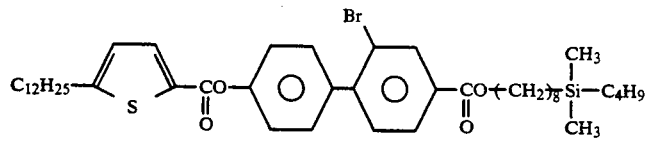
(I-154)
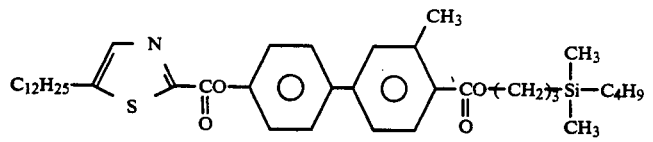
(I-155)
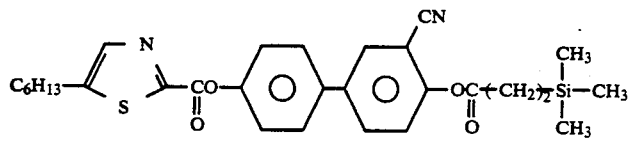
(I-156)
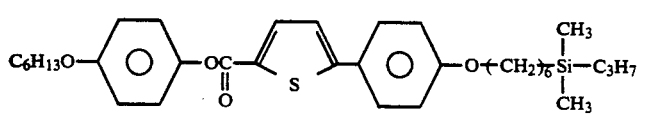
(I-157)
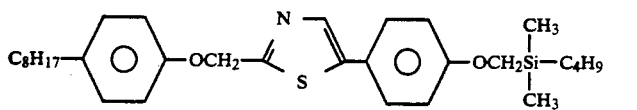
(I-158)

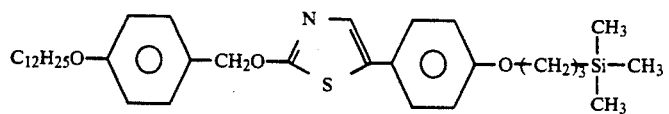 (I-159)
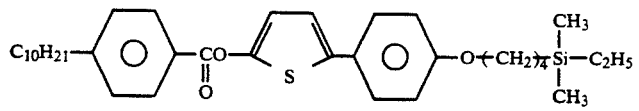 (I-160)
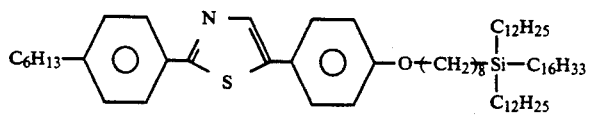 (I-161)
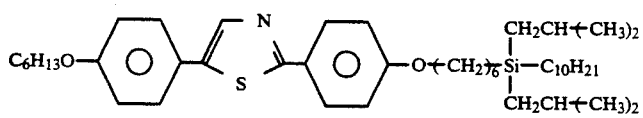 (I-162)
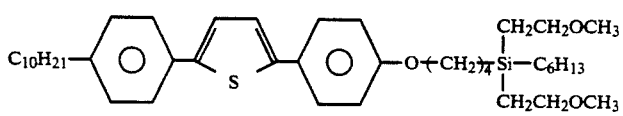 (I-163)
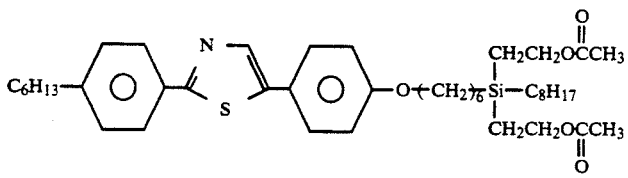 (I-164)
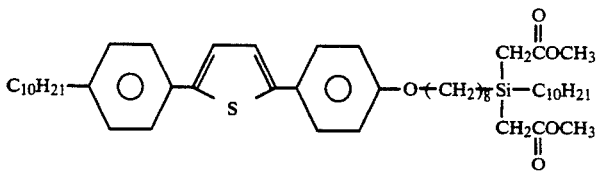 (I-165)
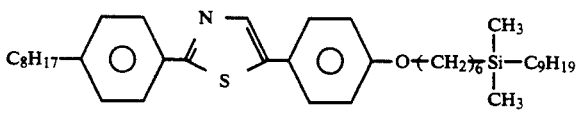 (I-166)
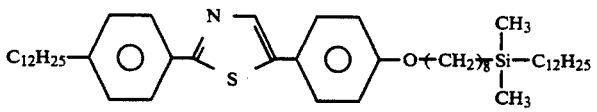 (I-167)
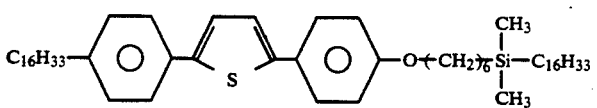 (I-168)
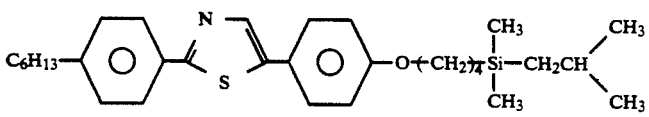 (I-169)
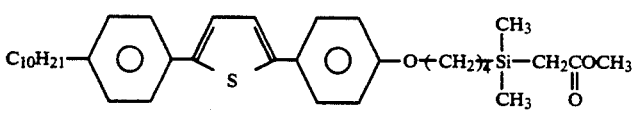 (I-170)

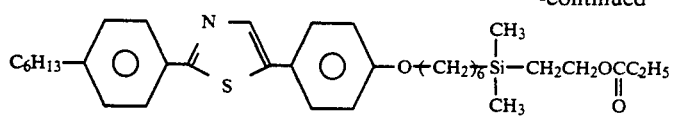 (I-171)

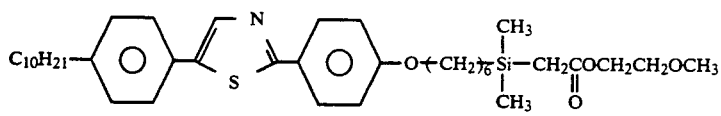 (I-172)

The liquid crystal composition according to the present invention may be obtained by mixing at least one species of the compound represented by the formula (I) and another mesomorphic compound in appropriate proportions. The liquid crystal composition according to the present invention may preferably be formulated as a liquid crystal composition capable of utilizing ferroelectricity, particularly a liquid crystal composition showing a chiral smectic phase.

Specific examples of another mesomorphic compound as described above may include those denoted by the following formulas (III) to (XI).

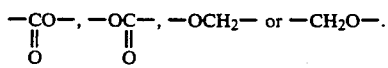

In the formula (III), preferred compounds thereof may include those represented by the following formulas (IIIa) to (IIId):

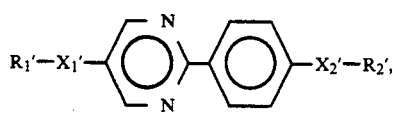 (IIIa)

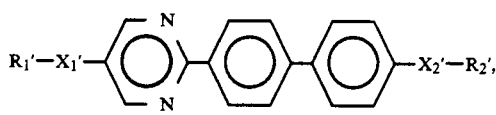 (IIIb)

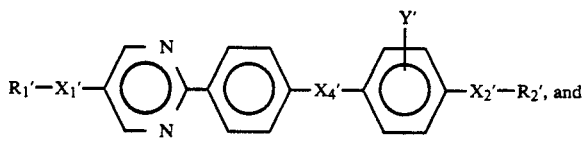 (IIIc)

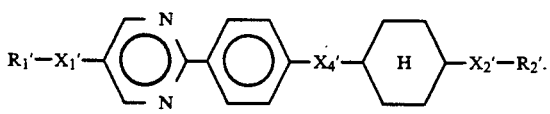 (IIId)

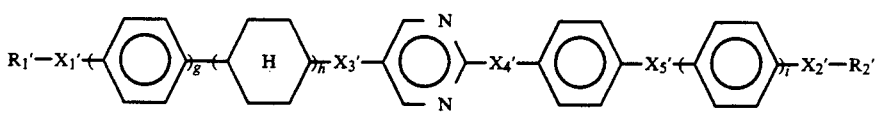 (IV)

wherein g and h respectively denote 0 or 1 with proviso that g+h=1; i denotes 0 or 1; $X_1'$ and $X_2'$ respectively denote a single bond, (III)

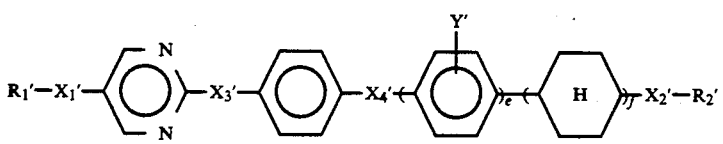

wherein e denotes 0 or 1 and f denotes 0 or 1 with proviso that e+f=0 or 1; Y' denotes H, halogen, $CH_3$ or $CF_3$; $X_1'$ and $X_2'$ respectively denote a single bond,

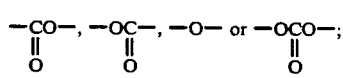

and $X_3'$ and $X_4'$ respectively denote a single bond

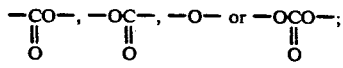

and $X_3'$, $X_4'$ and $X_5'$ respectively denote a single bond,

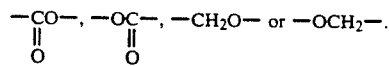

In the formula (IV), preferred compounds thereof may include those represented by the following formulas (IVa) to (IVc):

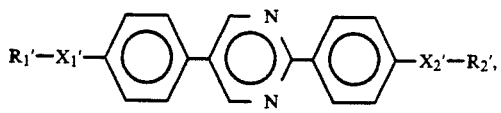
(IVa)

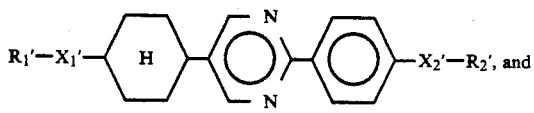
(IVb)

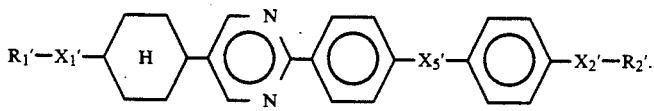
(IVc)

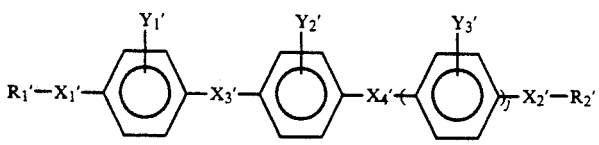
(V)

wherein j denotes 0 or 1; $Y_1'$, $Y_2'$ and $Y_3'$ respectively denote H, halogen, $CH_3$ or $CF_3$; $X_1'$ and $X_2'$ respectively denote a single bond,

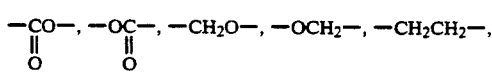

and $X_3'$ and $X_4'$ respectively denote a single bond,

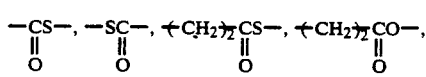

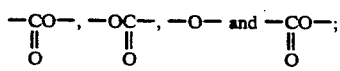

-continued

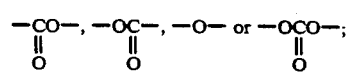

In the formula (V), preferred compounds thereof may include those represented by the following formulas (Va) and (Vb):

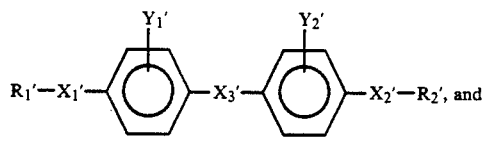
(Va)

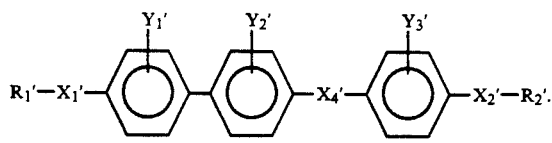
(Vb)

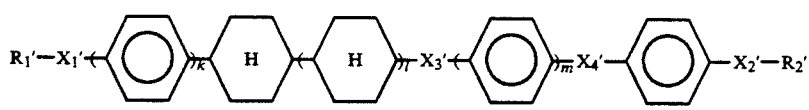
(VI)

wherein k, l and m respectively denote 0 to 1 with proviso that k+l+m=0, 1 or 2; $X_1'$ and $X_2'$ respectively denote a single bond,

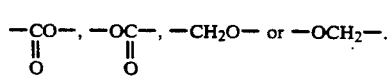

and $X_3'$ and $X_4'$ respectively denote a single bond,

-CO-, -OC-, -CH₂O- or -OCH₂-.

In the formula (VI), preferred compounds thereof may include those represented by the following formulas (VIa) to (VIf):

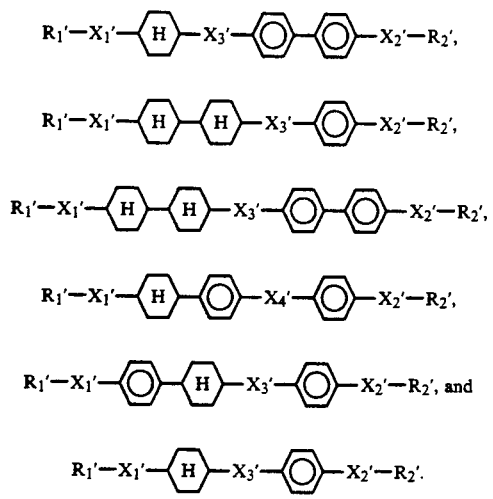

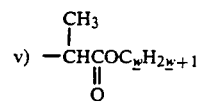

wherein w denotes an integer of 1-15 (optically active or inactive);

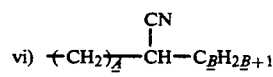

wherein A denotes an integer of 0-2 and B denotes an integer of 1-15 (optically active or inactive); and

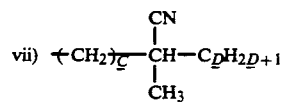

wherein C denotes an integer of 0-2 and D denotes an integer of 1-15 (optically active or inactive).

In the above-mentioned formula (III), more preferred compounds thereof may include those represented by the formulas (IIIaa) to (IIIdc):

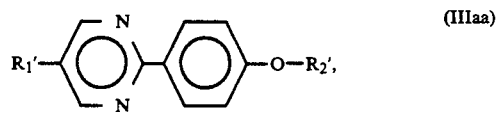

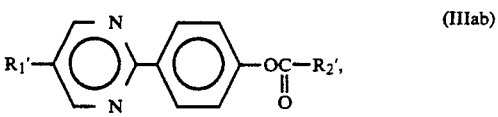

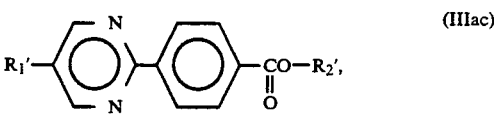

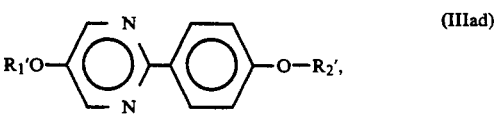

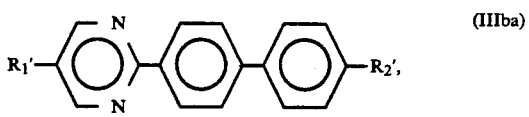

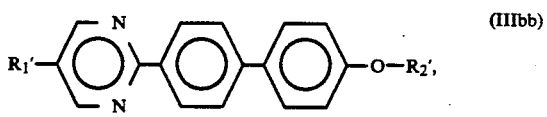

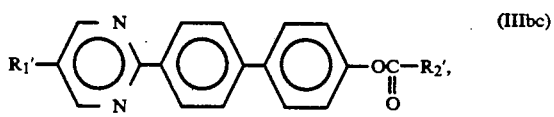

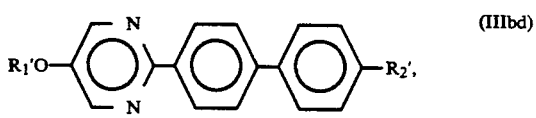

Herein, $R_1'$ and $R_2'$ respectively denote a linear or branched alkyl group having 1-18 carbon atoms capable of including one or two or more non-neighboring methylene groups which can be replaced with —CH halogen— and capable of further including one or two or more non-neighboring methylene groups other than those directly connected to $X_1'$ or $X_2'$ which can be replaced with at least one species of

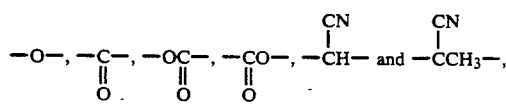

with proviso that $R_1'$ and $R_2'$ respectively do not connect to a ring structure by a single bond when $R_1'$ and $R_2'$ respectively denote a halogenated alkyl group containing one methylene group replaced with —CH halogen—.

Further, preferred examples of $R_1'$ and $R_2'$ may respectively include those represented by the following groups (i) to (vii):

i) a linear alkyl group having 1-15 carbon atoms;

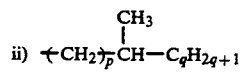

wherein p denotes an integer of 0-5 and q denotes an integer of 1-11 (optionally active or inactive);

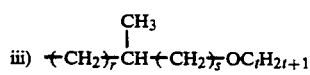

wherein r denotes an integer of 0-6, s denotes 0 or 1, and t denotes an integer of 1-14 (optically active or inactive);

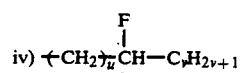

wherein u denotes 0 or 1 and v denotes an integer of 1-16;

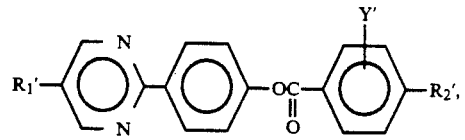 (IIIca)

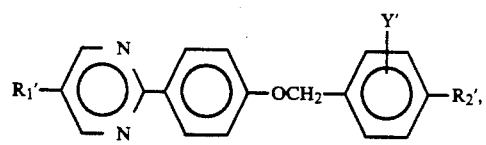 (IIIcb)

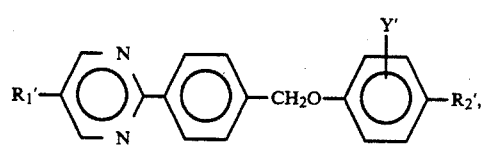 (IIIcc)

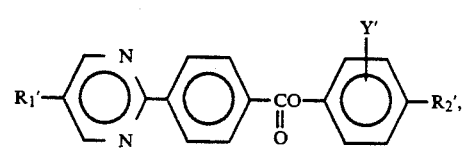 (IIIcd)

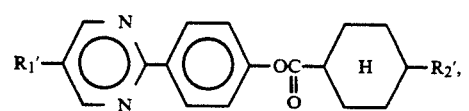 (IIIda)

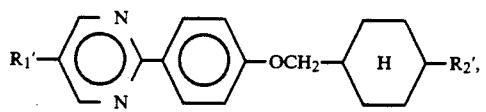 (IIIdb)

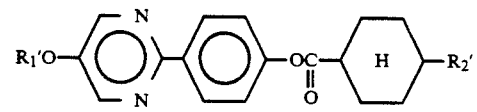 (IIIdc)

In the above-mentioned formula (IV), more preferred compounds thereof may include those represented by the formulas (IVaa) to (IVcd):

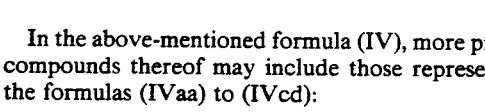 (IVaa)

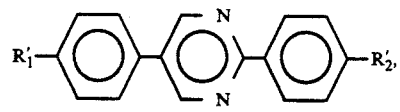 (IVab)

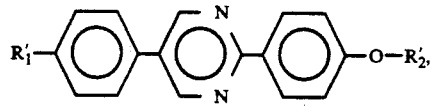 (IVba)

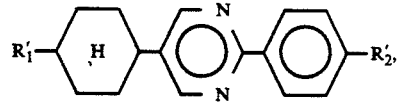 (IVca)

and

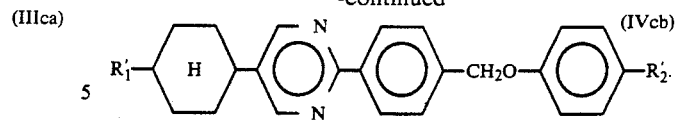 (IVcb)

In the above-mentioned formula (V), more preferred compounds thereof may include those represented by the formulas (Vaa) to (Vbf):

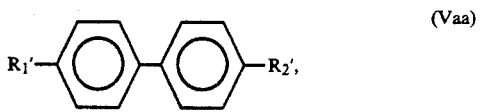 (Vaa)

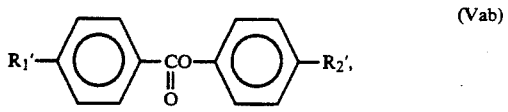 (Vab)

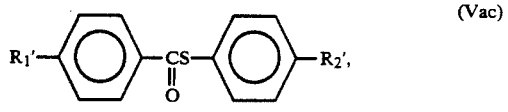 (Vac)

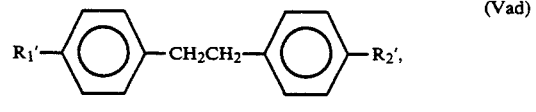 (Vad)

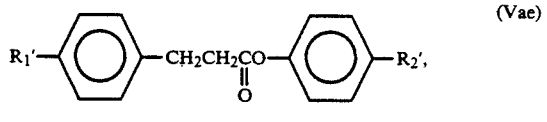 (Vae)

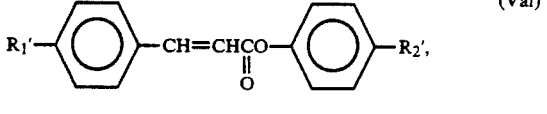 (Vaf)

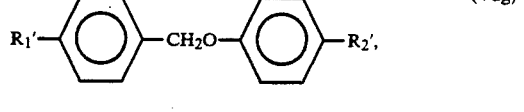 (Vag)

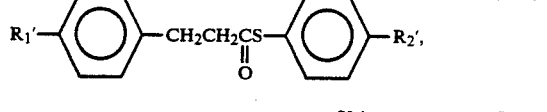 (Vah)

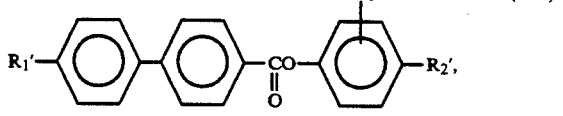 (Vba)

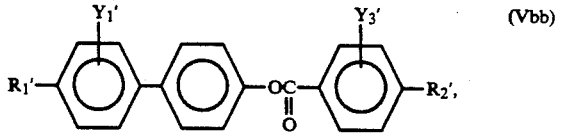 (Vbb)

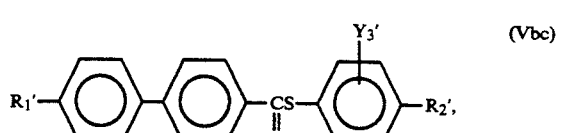 (Vbc)

-continued

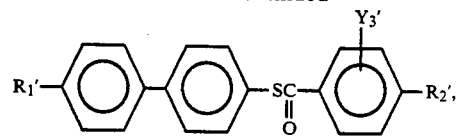 (Vbd)

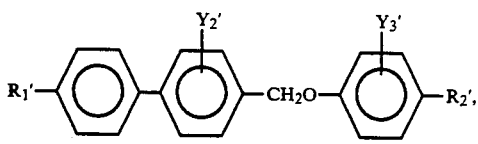 (Vbe)

and

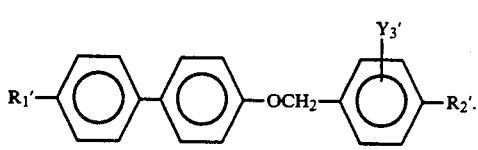 (Vbf)

In the above-mentioned formula (VI), more preferred compounds thereof may include those represented by the formulas (VIaa) to (VIfa):

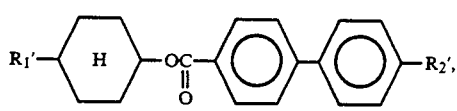 (VIaa)

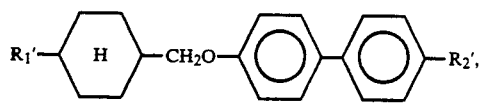 (VIab)

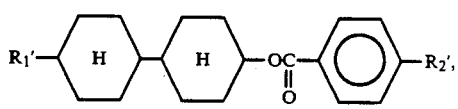 (VIba)

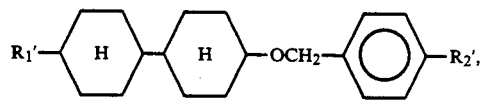 (VIbb)

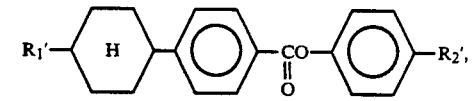 (VIda)

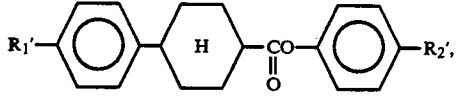 (VIea)

and

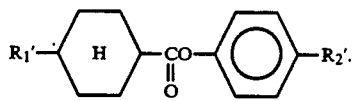 (VIfa)

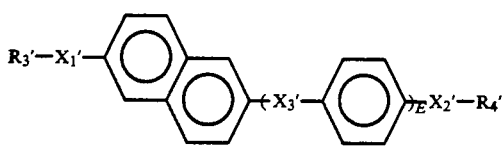 (VII)

wherein E denotes 0 or 1; $X_1'$ and $X_2'$ respectively denote a single bond,

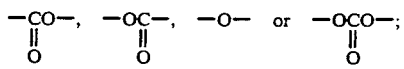

and $X_3'$ denotes a single bond,

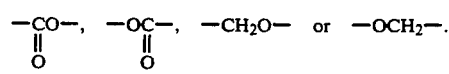

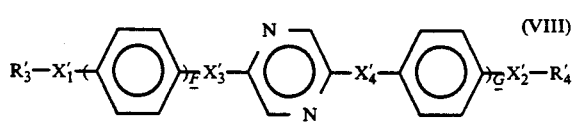 (VIII)

wherein F and G respectively denote 0 or 1; $X_1'$ and $X_2'$ respectively denote a single bond,

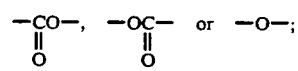

and $X_3'$ and $X_4'$ respectively denote a single bond,

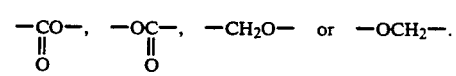

In the above formula (VII), preferred compounds thereof may include those represented by the following formulas (VIIa) and (VIIb):

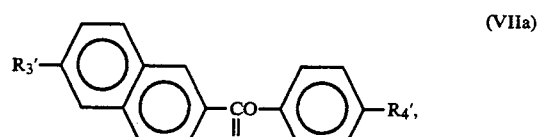 (VIIa)

and

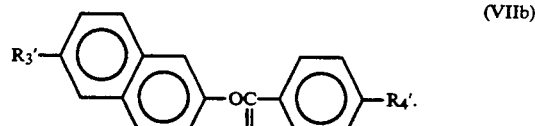 (VIIb)

In the above formula (VIII), preferred compounds thereof may include those represented by the following formulas (VIIIa) and (VIIIb).

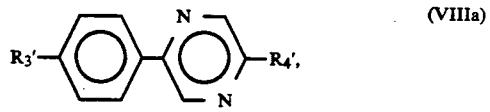 (VIIIa)

and

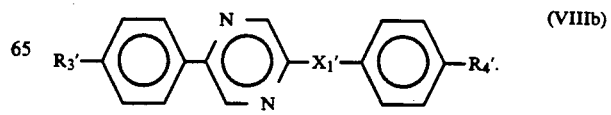 (VIIIb)

More preferred compounds of the formula (VIII) may include those represented by the formulas (VIIIaa) to (VIIIbb):

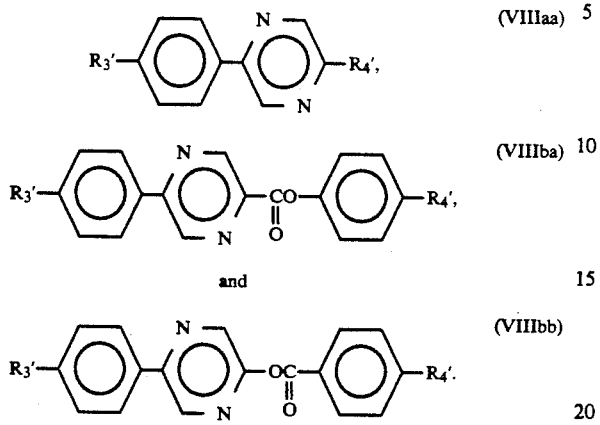

Herein, $R_3'$ and $R_4'$ respectively denote a linear or branched alkyl group having 1-18 carbon atoms capable of including one or two or more non-neighboring methylene groups which can be replaced with —CH halogen- and capable of further including one or two or more non-neighboring methylene groups other than those directly connected to $X_1'$ or $X_2'$ which can be replaced with at least one species of

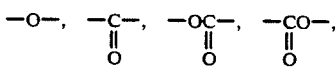
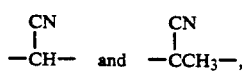

with proviso that $R_3'$ and $R_4'$ respectively do not connect to a ring structure by a single bond when $R_3'$ and $R_4'$ respectively denote a halogenated alkyl group containing one methylene group replaced with —CH halogen-.

Further, preferred examples of $R_3'$ and $R_4'$ may respectively include those represented by the following groups (i) to (vii):

i) a linear alkyl group having 1-15 carbon atoms;

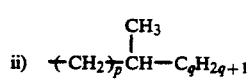

wherein p denotes an integer of 0-5 and q denotes an integer of 1-11 (optically active or inactive);

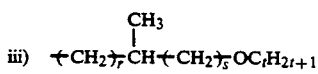

wherein r denotes an integer of 0-6, s denotes 0 or 1, and t denotes an integer of 1-14 (optically active or inactive);

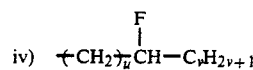

wherein u denotes an integer of 0 or 1 and v denotes an integer of 1-16;

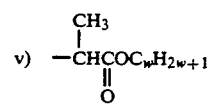

wherein w denotes an integer of 1-15 (optically active or inactive);

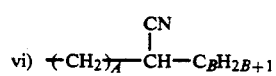

wherein A denotes an integer of 0-2 and B denotes an integer of 1-15 (optically active or inactive); and

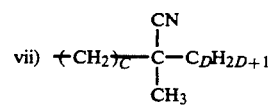

wherein C denotes an integer of 0-2 and D denotes an integer of 1-15 (optically active or inactive).

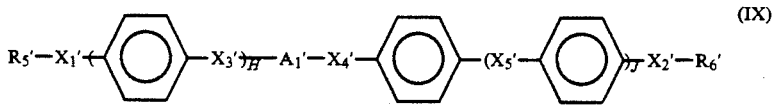

wherein H and J respectively denote 0 or 1 with proviso that H+J=0 or 1; $X_1'$ and $X_2'$ respectively denote a single bond,

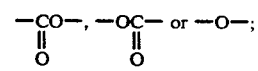

$A_1'$ denotes

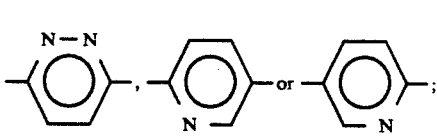

and $X_3'$ and $X_4'$ respectively denote a single bond,

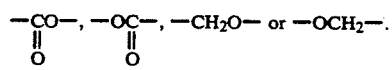

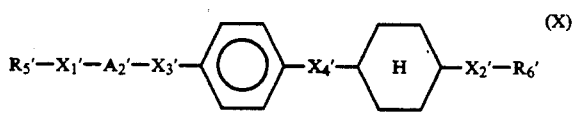

wherein $X_1'$ and $X_2'$ respectively denote a single bond,

—CO—, —OC—
 ‖       ‖
 O       O or —O—; $A_2'$ denotes

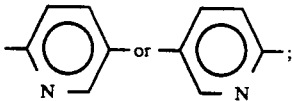

and $X_3'$ and $X_4'$ respectively denote a single bond,

—CO—, —OC—, —CH$_2$O— or —OCH$_2$—.
 ‖       ‖
 O       O

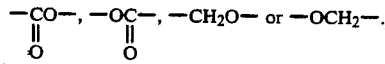 (XI)

wherein $X_1'$ and $X_2'$ respectively denote a single bond,

—CO—, —OC—
 ‖       ‖
 O       O or —O—; $A_3'$ denotes

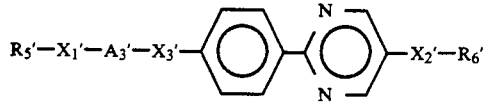

and $X_3'$ respectively denotes a single bond,

—CO—, —OC—,
 ‖       ‖
 O       O
—CH$_2$O— or —OCH$_2$—.

In the above formula (IV), preferred compounds thereof may include those represented by the following formulas (IXa) to (IXc):

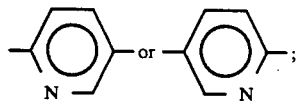 (IXa)

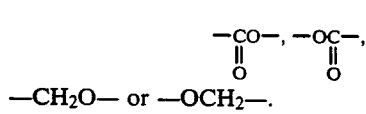 (IXb)

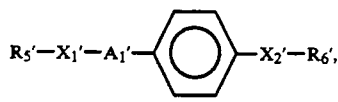 (IXc)

In the above formula (X), preferred compounds thereof may include those represented by the following formulas (Xa) and (Xb):

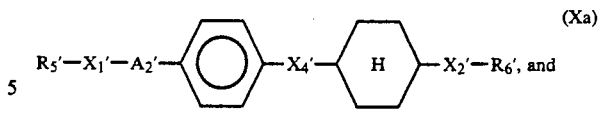 (Xa)

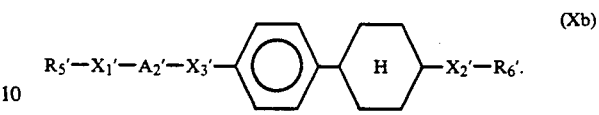 (Xb)

In the above-mentioned formula (IX), more preferred compounds thereof may include those represented by the formulas (IXaa) to (IXcc):

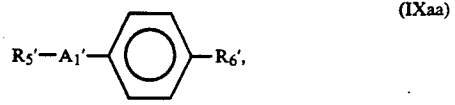 (IXaa)

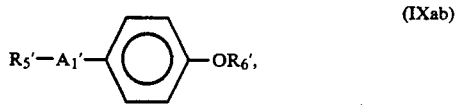 (IXab)

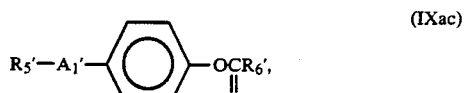 (IXac)

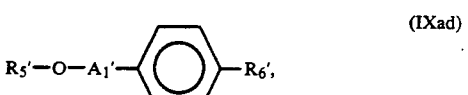 (IXad)

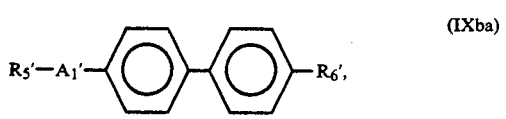 (IXba)

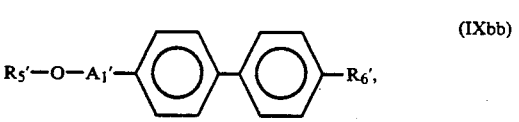 (IXbb)

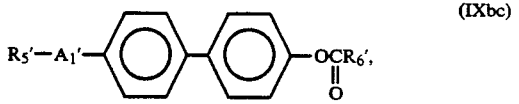 (IXbc)

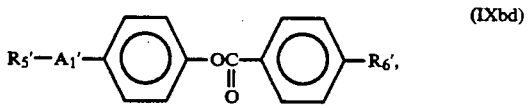 (IXbd)

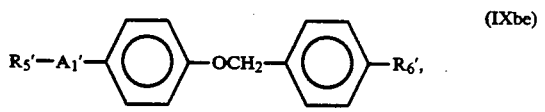 (IXbe)

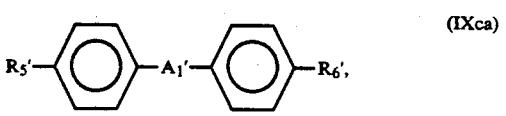 (IXca)

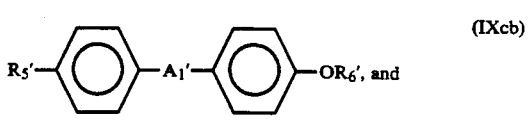 (IXcb)

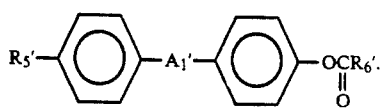
(IXcc)

In the above-mentioned formula (X), more preferred compounds thereof may include those represented by the formulas (Xaa) to (Xbb):

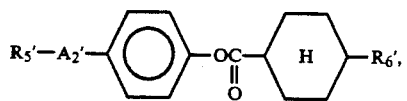
(Xaa)

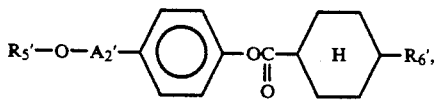
(Xab)

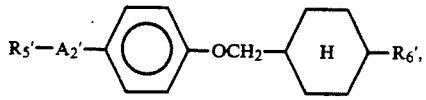
(Xac)

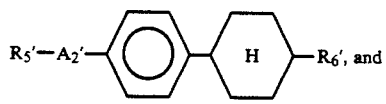
(Xba)

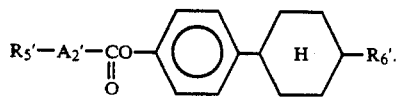
(Xbb)

In the above formula (XI), preferred compounds thereof may include those represented by the following formulas (XIa) to (XIg):

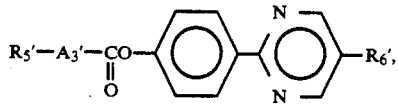
(XIa)

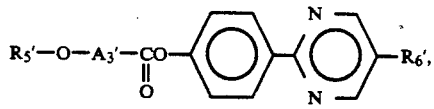
(XIb)

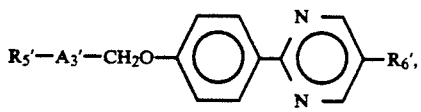
(XIc)

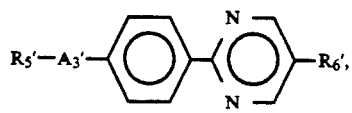
(XId)

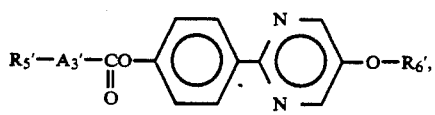
(XIe)

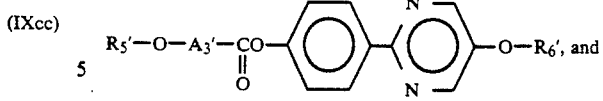
(XIf)

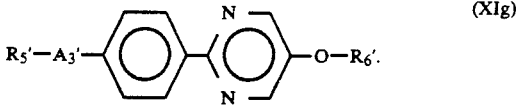
(XIg)

Herein, $R_5'$ and $R_6'$ respectively denote a linear or branched alkyl group having 1-18 carbon atoms capable of including one or two or more non-neighboring methylene groups other than those directly connected to $X_1'$ or $X_2'$ which can be replaced with at least one species of —O—, $$-\underset{\underset{O}{\|}}{C}-,\ -O\underset{\underset{O}{\|}}{C}-,\ -\underset{\underset{O}{\|}}{C}O-,\ -\underset{\underset{CH}{|}}{\overset{CN}{|}}-\ \text{and}\ -\underset{\underset{CCH_3}{|}}{\overset{CN}{|}}-.$$

Further, preferred examples of $R_5'$ and $R_6'$ may respectively include those represented by the following groups (i) to (vi):

i) a linear alkyl group having 1-15 carbon atoms;

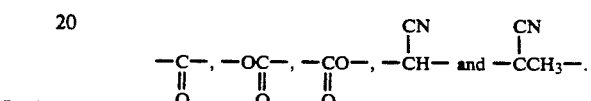

wherein p denotes an integer of 0-5 and q denotes an integer of 1-11 (optically active or inactive);

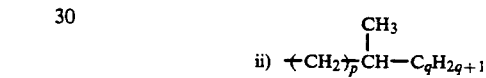

wherein r denotes an integer of 0-6, s denotes 0 or 1, and t denotes an integer of 1-14 (optically active or inactive);

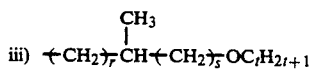

wherein w denotes an integer of 1-15 (optically active or inactive);

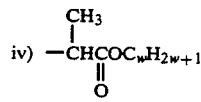

wherein A denotes an integer of 0-2 and B denotes an integer of 1-15 (optically active or inactive); and

wherein C denotes an integer of 0-2 and D denotes an integer of 1-15 (optically active or inactive).

In formulating the liquid crystal composition according to the present invention, the liquid crystal composition may desirably contain 1-80 wt. %, preferably 1-60 wt. %, more preferably 1-40 wt. % of a mesomorphic compound represented by the formula (I).

Further, when two or more species of the compounds represented by the formula (I) are used, the liquid crystal composition may desirably contain 1-80 wt %, preferably 1-60 wt. %, more preferably 1-40 wt. %, of the two or more species of the compounds represented by the formula (I).

The liquid crystal device according to the present invention may preferably be prepared by heating the liquid crystal composition assuming a chiral smectic phase prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the liquid crystal device utilizing ferroelectricity prepared as described above for explanation of the structure thereof.

Referring to FIG. 1, the liquid crystal device includes a liquid crystal layer 1 assuming a chiral smectic phase disposed between a pair of glass substrates 2 each having thereon a transparent electrode 3 and an insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2-10 wt. %, by spinner coating, dip coating, screen printing, spray coating or roller coating, followed by curing or hardening under prescribed hardening condition (e.g., by heating). The insulating alignment control layer may have a thickness of ordinarily 30Å–1 micron, preferably 30–3000 Å, further preferably 50–1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a liquid crystal assuming a chiral smectic phase is sealed up to provide a liquid crystal layer 1 in a thickness of generally 0.5 to 20 microns, preferably 1 to 5 microns.

The ferroelectric liquid crystal provided by the composition of the present invention may desirably assume a SmC* phase (chiral smectic C phase) in a wide temperature range including room temperature (particularly, broad in a lower temperature side) and also shows high-speed responsiveness, a smaller temperature-dependence of response speed and wide drive voltage margin when contained in a device.

Particularly, in order to show a good alignment characteristic to form a uniform monodomain, the ferroelectric liquid crystal may show a phase transition series comprising isotropic phase - Ch phase (cholesteric phase) - SmA phase (smectic A phase) - SmC* phase (chiral smectic C phase) on temperature decrease.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

FIG. 2 is a schematic illustration of a liquid crystal cell (device) utilizing ferroelectricity for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment ($P\perp$) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments ($P\perp$) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics by using voltage application means 31a and 31b, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

Figure 5:
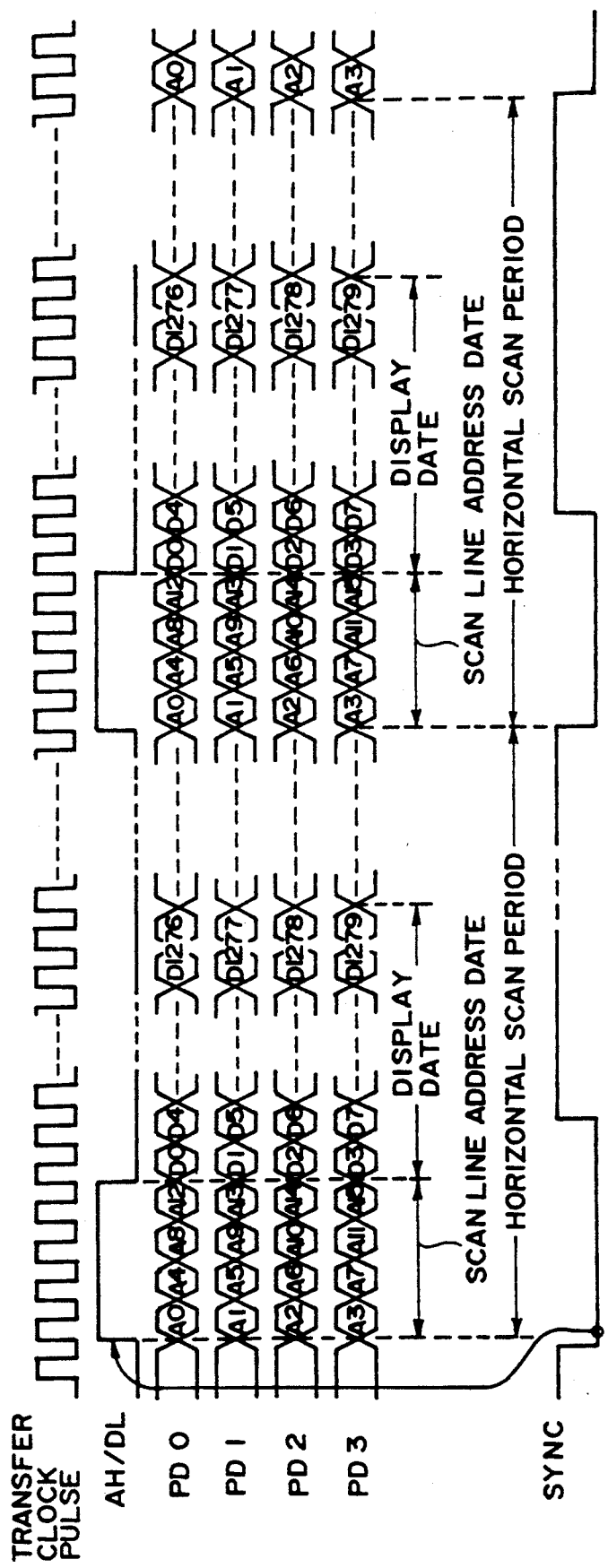
FIG. 5 is a time chart of image data communication showing time correlation between signal transfer and driving with respect to a liquid crystal display apparatus and a graphic controller.

Based on the arrangement and data format comprising image data accompanied with scanning line address data and by adopting communication synchronization using a SYNC signal as shown in FIGS. 4 and 5, there is provided a liquid crystal display apparatus of the present invention which uses the liquid crystal device according to the present invention as a display panel portion.

Referring to FIG. 4, the ferroelectric liquid crystal display apparatus 101 includes a graphic controller 102, a display panel 103, a scanning line drive circuit 104, a data line drive circuit 105, a decoder 106, a scanning signal generator 107, a shift resistor 108, a line memory 109, a data signal generator 110, a drive control circuit 111, a graphic central processing unit (GCPU) 112, a host central processing unit (host CPU) 113, and an image data storage memory (VRAM) 114.

Image data are generated in the graphic controller 102 in an apparatus body and transferred to a display panel 103 by signal transfer means shown in FIGS. 4 and 5. The graphic controller 102 principally comprises a CPU (central processing unit, hereinafter referred to as "GCPU") 112 and a VRAM (video-RAM, image data storage memory) 114 and is in charge of management and communication of image data between a host CPU 113 and the liquid crystal display apparatus (FLCD) 101. The control of the display apparatus is principally realized in the graphic controller 102. A light source is disposed at the back of the display panel 103.

Hereinbelow, the present invention will be explained more specifically with reference to examples. It is however to be understood that the present invention is not restricted to these examples.

EXAMPLE 1

4-[3-(butyldimethylsilyl)propoxy]phenyl 5-octylthiophene-2-carboxylate (Example Compound No. I-4) was synthesized through the following steps i)–iii).

i)
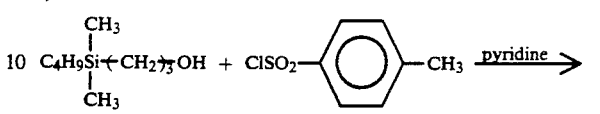

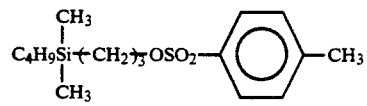

ii)
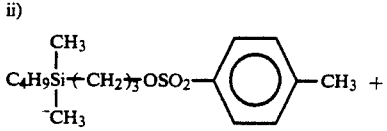

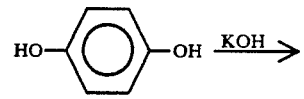

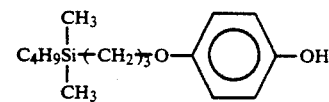

iii)
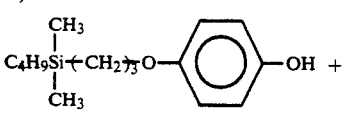

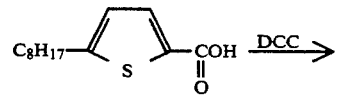

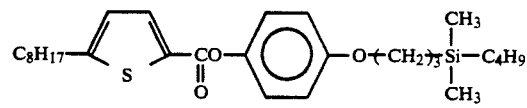

Step i) Production of 3-(butyldimethylsilyl)propyl p-toluenesulfonate 5.0 g (28.68 mM) of butyldimethyl-3-hydroxypropylsilane was added 50 ml of pyridine, followed by stirring. To the mixture, 5.4 g (28.32 mM) of p-toluenesulfonyl chloride was added under cooling on an ice bath, followed by stirring for 0.5 hour and further stirring for 4 hours at room temperature. After the reaction, the reaction mixture was poured into water, acidified with hydrochloric acid (pH≈2) and extracted with ethyl acetate, followed by washing with water and drying with anhydrous magnesium sulfate. The magnesium sulfate in the resultant mixture was filtered off and the filtrate was condensed into a solid to obtain 3-(butyldimethylsilyl)propyl p-toluenesulfonate (Yield: 81.7 %).

Step ii) Production of 4-[3-(butyldimethylsilyl)propoxy]phenol

The above-obtained 3-(butyldimethylsilyl)propyl p-toluenesulfonate was added dropwise in 45 min. to a mixture of 2.32 g (21.1 mM) of hydroquinone, 1.13 g (17.1 mM) of 85 %-potassium hydroxide, 6 ml of methanol and 30 ml of ethanol under stirring at 65° C., followed by stirring for 0.5 hour and further stirring for 6 hour at 80° C. After the reaction, the reaction mixture was poured into cold water, acidified with hydrochloric acid (pH≃2) and extracted with ethyl acetate, followed by washing with water and drying with anhydrous magnesium sulfate. The magnesium sulfate in the resultant mixture was filtered off and the filtrate was condensed into a solid, followed by purification by silica gel column chromatography (eluent: toluene) to obtain 2.05 g of 4-[3-(butyldimethylsilyl)propoxy]phenol (Yield: 50.6 %).

Step iii) Production of 4-[3-butyldimethylsilyl)propoxy]phenyl 5-octylthiophene-2-carboxylate 15 ml of dichloromethane was added to 0.38 g (1.58 mM) of 5-octylthiophene-2-carboxylic acid and 0.42 g (1.58 mM) of 4-[3-(butyldimethylsilyl)propoxy]phenol, followed by stirring at room temperature to the mixture, 0.31 g (1.50 mM) of N,N'-dicyclohexylcarbodiimide (DCC) and 0.02 g of 4-pyrrolidinopyridine were added, followed by stirring for 5 hours at room temperature. The resultant dicyclohexylurea was recovered by filtration, followed by washing with dichloromethane to be added to the filtrate. The resultant dichloromethane solution was condensed into a solid under reduced pressure, followed by purification by silica gel column chromatography (eluent: toluene) and recrystallization from ethanol to obtain 0.45 g of 4-[3-(butyldimethylsilyl)propoxy]phenyl 5-octylthiophene-2-carboxylate (Yield: 61.4 %).

Phase transition temperature (°C.)

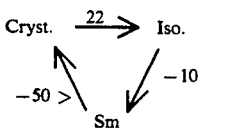

Herein, the respective symbols denote the following phases; Iso.: isotropic phase; Sm: smectic phase (unidentified); and Cryst.: crystal.

EXAMPLE 2

4-[3-(butyldimethylsilyl)propoxycarbonyl]biphenyl 5-hexylthiophene-2-carboxylate (Example Compound I-10) was synthesized through the following steps i) and ii).

Step i) Production of 3-butyldimethylsilylpropyl 4'-hydroxybiphenyl-4-carboxylate 2.27 g (10.6 mM) of 4-hydroxybiphenyl-4'-carboxylic acid, 3.71 g (21.3 mM) of butyldimethyl-3-hydroxypropylsilane, 0.25 g (1.31 mM) of p-toluenesulfonic acid and 30 ml of xylene were mixed and heat-refluxed for 8 hours under stirring. After the reaction, the reaction mixture was cooled, followed by distilling-off of xylene under reduced pressure. The resultant residue was dissolved in ethyl acetate and washed with water, followed by drying with anhydrous magnesium sulfate. The magnesium sulfate in the resultant mixture was filtered off and the filtrate was condensed into a solid under reduced pressure, followed by purification by silica gel column chromatography (eluent: toluene) to obtain 1.87 g of 3-butyldimethyl-silylpropyl 4'-hydroxybiphenyl-4-carboxylic acid (Yield; 47.6 %).

Step ii) Production of 4-3-butyldimethylsilyl)propoxycarbonyl]biphenyl 5-hexylthiophene-2-carboxylate 20 ml of dichloromethane was added to 0.58 g (2.73 mM) of 5-hexylthiophene-2-carboxylic acid and 1.0 g (2.70 mM) of 3-butyldimethylsilylpropyl 4'-hydroxybiphenyl-4-carboxylic acid, followed by stirring at room temperature. To the mixture, 0.55 g (2.67 mM) of DCC and 0.05 g of 4-pyrrolidinopyridine were added, followed by stirring for 5 hours at room temperature. The resultant dicyclohexylurea was recovered by filtration, followed by washing with dichloromethane to be added to the filtrate. The resultant dichloromethane solution was condensed into a solid under reduced pressure, followed by purification by silica gel column chromatography (eluent: toluene) and recrystallization from ethanol to obtain 0.25 g of 4-[3-(butyldimethylsilyl)propoxycarbonyl]biphenyl 5-hexylthiophene-2-carboxylic acid (Yield: 17%).

Phase transition temperature (°C.)

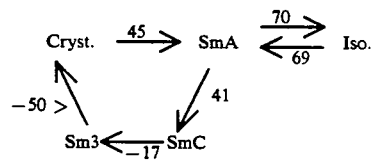

SmA: smectic A phase,
SmC: smectic C phase, and
Sm3: smectic phase (unidentified).

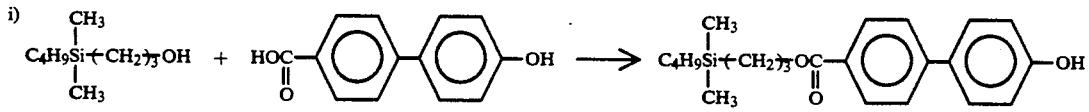

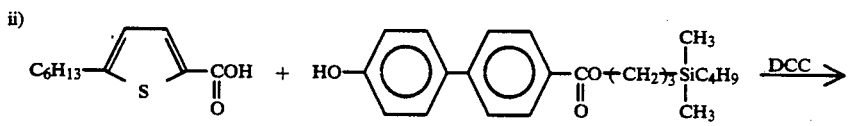

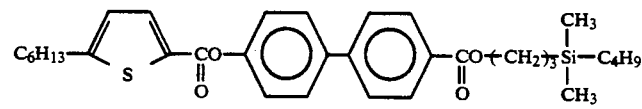

EXAMPLE 3

2-decyl-5-[4-(3-butyldimethylsilylpropyl)phenyl]thiophene (Example Compound No. I-22) was synthesized through the following steps i)-v).

i)
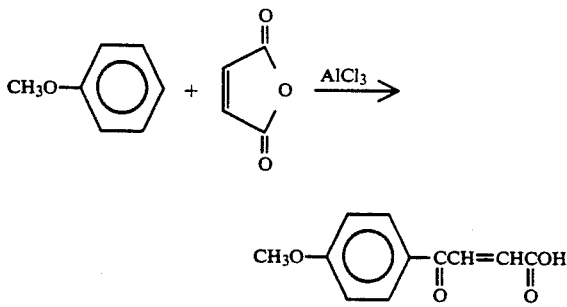

ii)
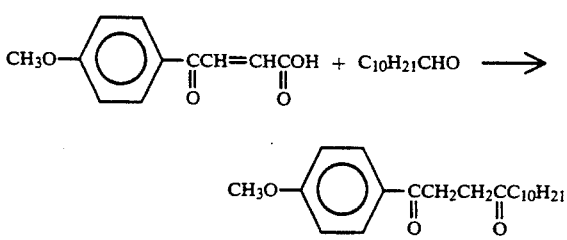

iii)
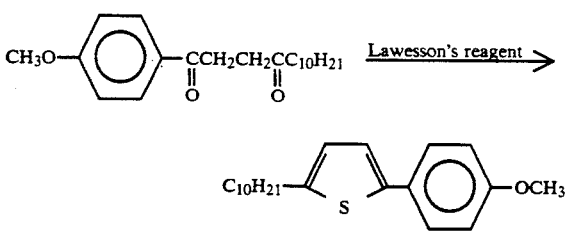

iv)
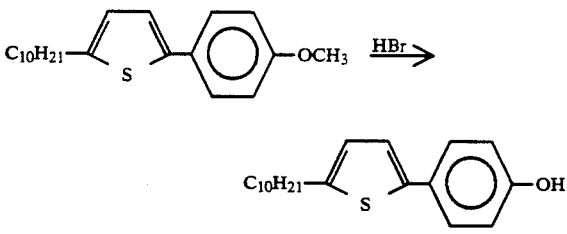

v)
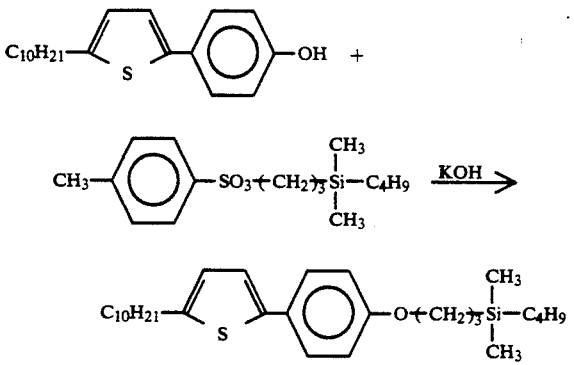

Step i) Production of β-(p-methoxybenzoyl)acrylic acid

In a 10 liter-reaction vessel, 500 g (4.63 M) of anisole, 500 g (5.10 M) of maleic anhydride and 3 liters of nitrobenzene were placed and cooled below 0° C. To the mixture, 1375 g of anhydrous aluminum chloride was added little by little in 90 min. below 5 ° C. under stirring, followed by further stirring 24hours below 5° C. After the reaction, a mixture solution of 700 ml of concentrated hydrochloric acid and 2.1 liters of water was added to the reaction mixture, followed by extraction with ethyl acetate. The organic layer was washed with water and dried, followed by distilling-off of ethyl acetate under reduced pressure. The resultant liquid was poured into 6 liters of hexane to precipitate a crystal. The crystal was recovered by filtration and recrystallized from benzene to obtain 450 g of an objective product (Yield: 47.2 %).

Step ii) Production of 1-(4-methoxyphenyl)-1,4-tetradecanedione

In a 1 liter-reaction vessel, 95.0 g ($4.61 \times 10^{-1}$ M) of -(p-methoxybenzoyl)acrylic acid, 48.9 g ($4.61 \times 10^{-1}$ M) of sodium carbonate and 460 ml of ethanol were placed and stirred for 50 min. at room temperature. To the mixture, 78.4 g ($4.16 \times 10^{-1}$ M) of n-undecylaldehyde, 12.4 g of 3-benzyl-5-(2-hydroxymethyl)-4-methyl-1,3-thiazolium bromide and 46.6 g of triethylamine were added, followed by heat-refluxing for 8 hours and distilling-off of the solvent. The resultant residue was recovered by adding 500 ml of water and 1 liter of chloroform. The resultant organic layer was successively washed with 10 %-sulfuric acid (200 ml×2), 5 %-sodium hydrogencarbonate aqueous solution (200 ml×2) and water (200 ml×2), followed by drying and distilling-off of the solvent to obtain 154 g of a crude product. The crude product was recrystallized from ethanol to obtain 94.7 g of an objective product (Yield: 61.9 %).

Step iii) Production of 2-decyl-5-(p-methoxyphenyl)thiophene

In a 1 liter-reaction vessel, 63.0 g ($1.90 \times 10^{-1}$ M) of 1-(4-methoxyphenyl)-1,4-tetradecanedione, 76.9 g ($1.90 \times 10^{-1}$ M) of Lawesson's reagent and 450 ml of toluene were placed and heat-refluxed for 15 min., followed by distilling-off the solvent. The resultant residue was purified by silica gel column chromatography (eluent: n-hexane/ethyl acetate =20/1) to obtain 62.8 g of an objective product.

Step iv) Production of 2-decyl-5-(4-hydroxyphenyl)thiophene

In a 1 liter-reaction vessel, 50.0 g ($1.52 \times 10^{-1}$ M) of 2-decyl-5-(p-methoxyphenyl)thiophene, 500 ml of a solution of 25 %-hydrogen bromide in acetic acid and 24 ml of 57 %-hydroiodic acid were placed, followed by stirring for 2 hours at 100° C. After the reaction, the reaction mixture was poured into 3 liters of water to precipitate a crystal. The crystal was recovered by filtration and washed with water, followed by drying and recrystallization from n-hexane to obtain 14.7 g of an objective product (Yield: 30.6%).

Step v) Production of 2-decyl-5-[4-(3-butyldimethylsilylpropoxy)phenyl]thiophene 0.32 g (1.0 mM) of 2-decyl-5-(4-hydroxyphenyl) thiophene, 0.07 g of 85%-KOH and 12 ml of n-butanol were mixed. To the mixture, 0.33 g (1.0 mM) of 3-(butyldimethylsilyl)propyl p-toluenesulfonate was added dropwise, followed by stirring for 7 hours at 100° C. After the reaction, the reaction mixture was poured into water and extracted with ethyl acetate, followed by washing with water and drying with anhydrous magnesium sulfate. The magnesium sulfate in the resultant mixture was filtered off and the filtrate was condensed into a solid, followed by purification by silica gel column chromatography (eluent: toluene) and recrystallization from a mixture solvent (ethanol/ethyl acetate) to obtain 0.28 g of 2-decyl-5-[4-(3-butyldimethylsilyl-propoxy)phenyl]thiophene (Yield: 59.2%).

Phase transition temperature (°C)

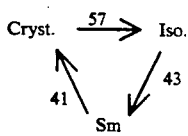

EXAMPLE 4

2-(4-hexylphenyl)-5-[4-(3-butyldimethylsilylpropoxy)phenyl]thiophene (Example Compound No. I-29) was synthesized through the following steps i)–iv).

i)
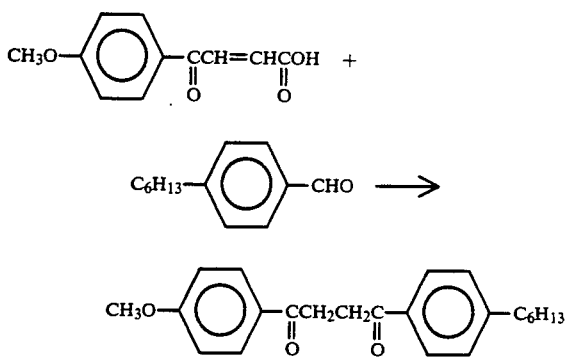

ii)
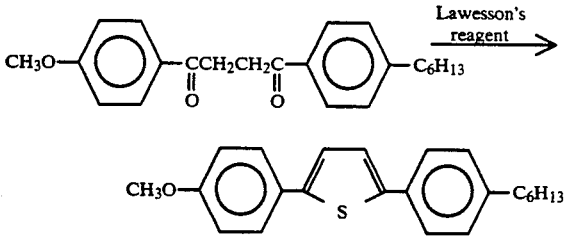

iii)
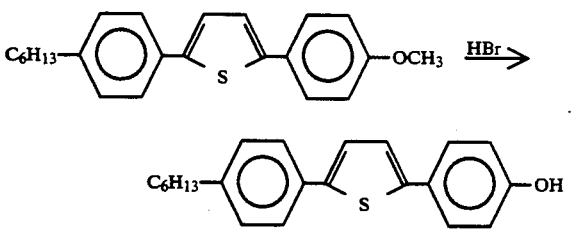

iv)
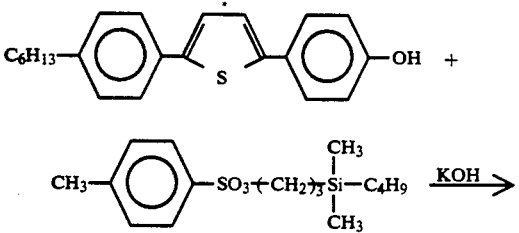

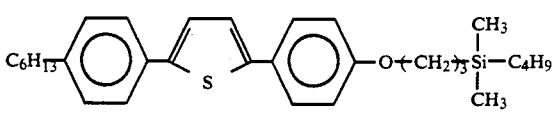

Step i) Production of 1-(4-methoxyphenyl)-4-(4-hexylphenyl)-1,4-butanedione

In a 1 liter-reaction vessel, 09.0 g ($4.37 \times 10^{-1}$ M) of β-(p-methoxybenzoyl)acrylic acid, 46.3 g ($4.37 \times 10^{-1}$ M) of sodium carbonate and 440 ml of ethanol were placed and stirred for 30 min. at room temperature. To the mixture, 83.0 g ($4.37 \times 10^{-1}$ M) of p-n-hexylbenzaldehyde, 13.6 g of 3-ethyl-5-(2-hydroxyethyl)-4-methyl-1,3-thiazolium bromide and 44.1 g of triethylamine were added, followed by heat-refluxing for 8.5 hours and distilling-off of the solvent. The resultant residue was recovered by adding 500 ml of water and 1 liter of chloroform. The resultant organic layer was successively washed with 10%-sulfuric acid (200 ml×2), 5%-sodium hydrogencarbonate aqueous solution (200 ml×2) and water (200 ml×2), followed by drying and distilling-off of the solvent to obtain 142 g of a crude product. The crude product was recrystallized from ethanol to obtain 114.0 g of an objective product (Yield: 74.1%).

Step ii) Production of 2-(4-hexylphenyl)-5-(4-methoxyphenyl)thiophene

In a 1 liter-reaction vessel, 68.0 g ($1.93 \times 10^{-1}$ M) of 1-(4-methoxyphenyl)-4-(4-hexylphenyl)-1,4-butanedione, 78.2 g ($1.94 \times 10^{-1}$ M) of Lawesson's 1,4-butane reagent and 340 ml of toluene were placed and heat-refluxed for 20 min., followed by distilling-off the solvent. The resultant residue was purified by silica gel column chromatography (eluent: n-hexane/ethyl acetate =20/1) to obtain 63.1 g of an objective product (Yield: 93.4%).

Step iii) Production of 2-(4-hexylphenyl)-5-(4-hydroxyphenyl)thiophene

In a 1 liter-reaction vessel, 50.0 g ($1.43 \times 10^{-1}$ M) of 2-(4-hexylphenyl)-5-(4-methoxyphenyl)thiophene, 500 ml of a solution of 25%-hydrogen bromide in acetic acid and 24 ml of 57%-hydroiodic acid were placed, followed by stirring for 20 hours at 100° C. After the reaction, the reaction mixture was poured into 3 liters of water to precipitate a crystal. The crystal was recovered by filtration and washed with water, followed by drying and successive recrystallization from ethanol and chloroform to obtain 24.6 g of an objective product (Yield: 51.2%).

Step iv) Production of 2-(4-hexylphenyl)-5-[4-(3-butyl-dimethyl-silylpropoxy)phenyl]thiophene 0.67 g (2.0 mM) of 2-(4-hexylphenyl)-5-(4-hydroxyphenyl)thiophene, 0.19 g of 85%-KOH and 2 ml of n-butanol were mixed. To the mixture, a solution of 0.73 g (2.2 mM) of 3-butyldimethylsilyl)propyl p-toluenesulfonate in 1 ml of n-butanol was added, followed by heat-refluxing for 7 hours under stirring. After the reaction, the reaction mixture was poured into water and extracted with ethyl acetate, followed by washing with water and drying with anhydrous magnesium sulfate. The magnesium sulfate in the resultant mixture was filtered off and the filtrate was condensed into a solid, followed by purification by silica gel column chromatography (eluent: toluene) and recrystallization from a mixture solvent (toluene/methanol) to obtain 0.69 g of 2-(4-hexylphenyl)-5-[4-(3-butyldimethylsilylpropoxy)-phenyl]thiophene (Yield: 70/1%).

Phase transition temperature (°C.)

Cryst. ⇌ 111/107 Iso.

EXAMPLE 5

2-(4-hexylphenyl)-5-[3-fluoro-4-(3-butyldimethylsilyl-propoxy)phenyl]thiophene (Example Compound No. I-34) was synthesized through the following steps i)–iv).

i)

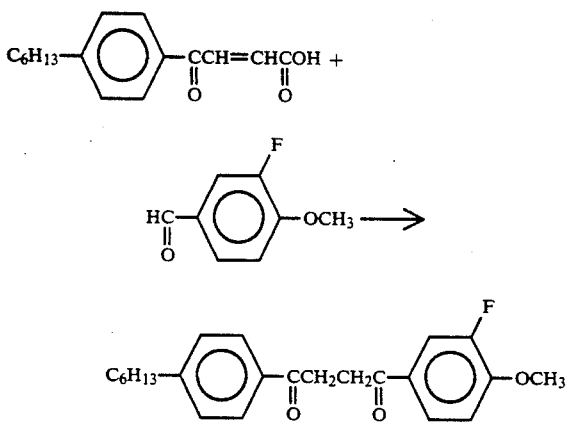

ii)

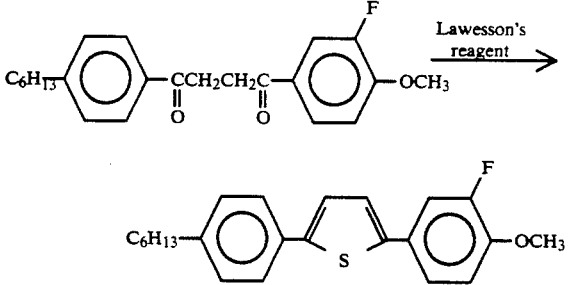

iii)

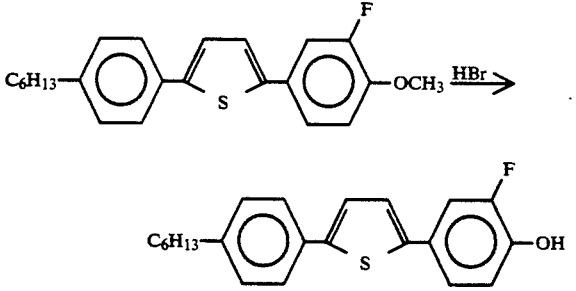

iv)

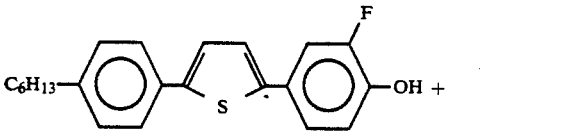

-continued

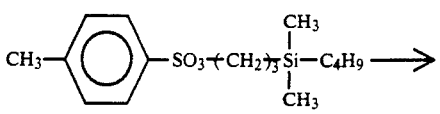

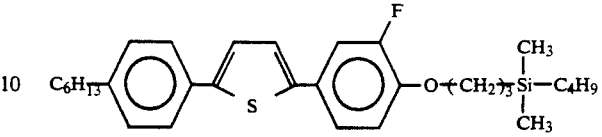

Step i) Production of 1-(4-hexylphenyl)-4-(3-fluoro-4-methoxyphenyl)-1,4-butanedione In a 200 ml-reaction vessel, 16.0 g ($6.15 \times 10^{-2}$ M) of β-(p-hexylbenzoyl)acrylic acid, 6.53 g ($6.16 \times 10^{-2}$ M) of sodium carbonate and 65 ml of ethanol were placed and stirred for 40 min. at room temperature. To the mixture, 9.48 g ($6.16 \times 10^{-2}$ M) of 3-fluoro-p-anisic aldehyde, 1.92 g of 3-ethyl-5-(2-hydroxyethyl)-4-methyl-1,3-thiazolium bromide and 6.24 g ($6.18 \times 10^{-2}$ M) of triethylamine were added, followed by heat-refluxing for 7 hours and distilling-off of the solvent. The resultant residue was recovered by adding 100 ml of water and 200 ml of chloroform. The resultant organic layer was successively washed with 10%-sulfuric acid (40 ml×2), 5%-sodium hydrogencarbonate aqueous solution (40 ml×2) and water (40 ml×2), followed by drying and distilling-off of the solvent to obtain 22.5 g of a crude product. The crude product was recrystallized from ethanol to obtain 15.0 g of an objective product (Yield: 65.9%).

Step ii) Production of 2-(4-hexylphenyl)-5-(3-fluoro4-methoxyphenyl)thiophene

In a 200 ml-reaction vessel, 15.0 g ($4.05 \times 10^{-2}$ M) of 1-(4-hexylphenyl)-4-(3-fluoro-4-methoxyphenyl)1,4-butanedione, 16.4 g ($4.05 \times 10^{-2}$ M) of Lawesson's reagent and 80 ml of toluene were placed and heat-refluxed for 3 min., followed by distilling-off the solvent. The resultant residue was purified by silica gel column chromatography (eluent: n-hexane/ethyl acetate =6/1) to obtain 15.0 g of an objective product.

Step iii) Production of 2-(4-hexylphenyl)-5-(3-fluoro4-hydroxyphenyl) thiophene

In a 300 ml-reaction vessel, 15.0 g ($4.08 \times 10^{-2}$ M) of 2-(4-hexylphenyl)-5-(3-fluoro-4-methoxyphenyl)thiophene, 150 ml of a solution of 25%-hydrogen bromide in acetic acid and 7 ml of 57%-hydroiodic acid were placed, followed by stirring for 26 hours at 100° C. After the reaction, the reaction mixture was poured into 1 liter of water to precipitate a crystal. The crystal was recovered by filtration and washed with water, followed by drying and successive purification by silica gel column chromatography (eluent: n-hexane/ethyl acetate=6/1 and benzene/hexane=2/1) to obtain 4.4 g of an objective product (Yield: 30.5%).

Step iv) Production of 2-(4-hexylphenyl)-5-[3-fluoro-4-(3-butyldimethyl-silylpropoxy)phenyl]thiophene 0.71 g (2.0 mM) of 2-(4-hexylphenyl)-5-(3-fluoro-4-hydroxyphenyl) thiophene, 0.19 g of 85%-KOH and 2 ml of n-butanol were mixed. To the mixture, a solution of 0.73 g (2.2 mM) of 3-(butyldimethylsilyl)propyl p-toluenesulfonate in 1 ml of n-butanol was added, followed by heat-refluxing for 7 hours at 100° C. under stirring. After the reaction, the reaction mixture was poured into water and extracted with ethyl acetate, followed by washing with water and drying with anhydrous magnesium sulfate. The magnesium sulfate in the resultant mixture was filtered off and the filtrate was condensed into a solid, followed by purification by silica gel column chromatography (eluent: toluene) and recrystallization from a mixture solvent (toluene/methanol) to obtain 0.81 g of 2-(4-hexylphenyl)-5-[3-fluoro-4-(3-butyldimethylsilylpropoxy)phenyl]thiophene (Yield: 79.4%).

Phase transition temperature (°C.)

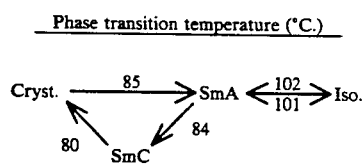

EXAMPLE 6

2-(4-hexylphenyl)-5-[4-(3-trimethylsilylpropoxy)phenyl]-1,3-thiazole (Example Compound No. I-51) was synthesized through the following steps i)–vi).

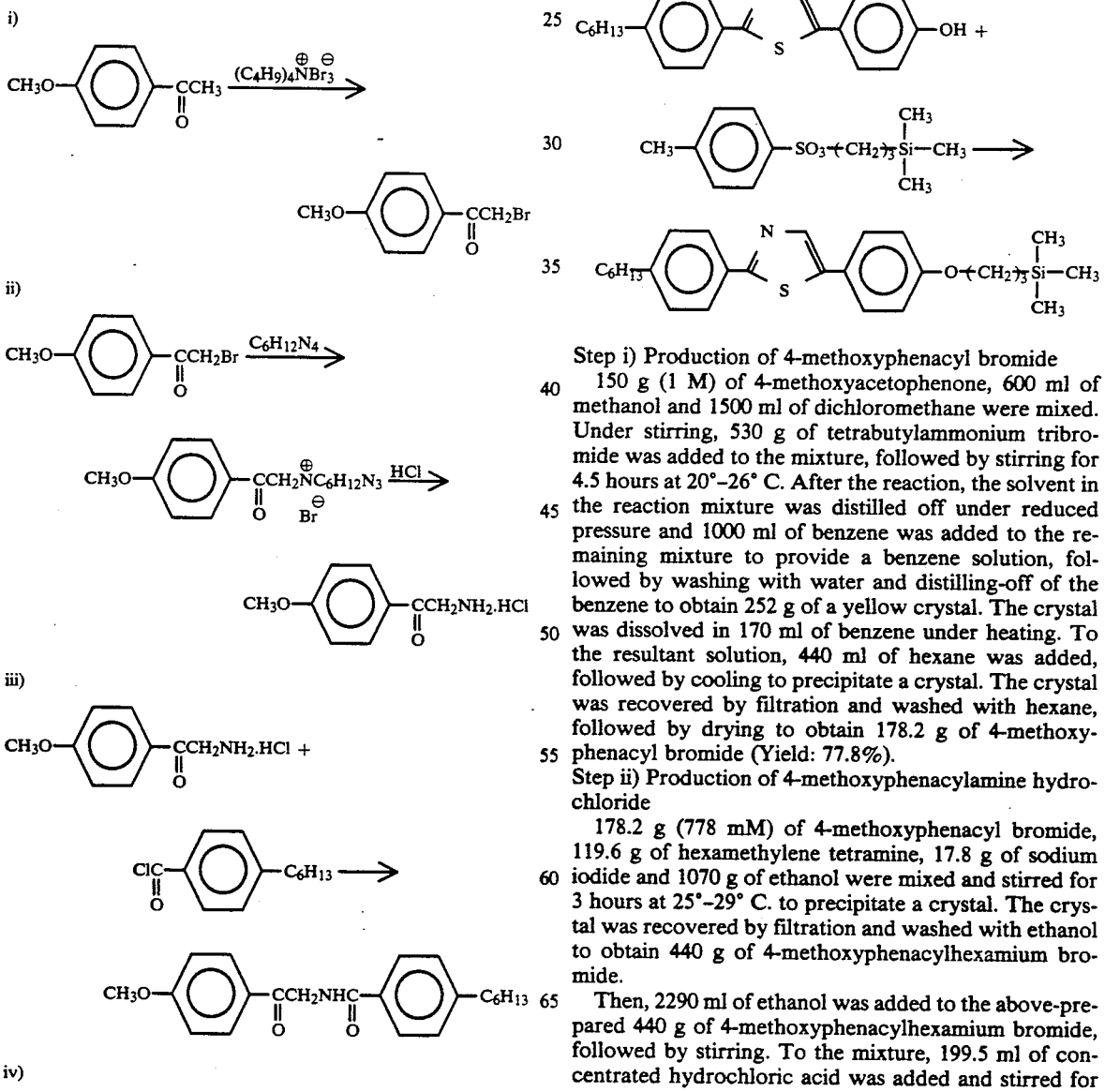

Step i) Production of 4-methoxyphenacyl bromide 150 g (1 M) of 4-methoxyacetophenone, 600 ml of methanol and 1500 ml of dichloromethane were mixed. Under stirring, 530 g of tetrabutylammonium tribromide was added to the mixture, followed by stirring for 4.5 hours at 20°–26° C. After the reaction, the solvent in the reaction mixture was distilled off under reduced pressure and 1000 ml of benzene was added to the remaining mixture to provide a benzene solution, followed by washing with water and distilling-off of the benzene to obtain 252 g of a yellow crystal. The crystal was dissolved in 170 ml of benzene under heating. To the resultant solution, 440 ml of hexane was added, followed by cooling to precipitate a crystal. The crystal was recovered by filtration and washed with hexane, followed by drying to obtain 178.2 g of 4-methoxyphenacyl bromide (Yield: 77.8%).

Step ii) Production of 4-methoxyphenacylamine hydrochloride 178.2 g (778 mM) of 4-methoxyphenacyl bromide, 119.6 g of hexamethylene tetramine, 17.8 g of sodium iodide and 1070 g of ethanol were mixed and stirred for 3 hours at 25°–29° C. to precipitate a crystal. The crystal was recovered by filtration and washed with ethanol to obtain 440 g of 4-methoxyphenacylhexamium bromide.

Then, 2290 ml of ethanol was added to the above-prepared 440 g of 4-methoxyphenacylhexamium bromide, followed by stirring. To the mixture, 199.5 ml of concentrated hydrochloric acid was added and stirred for 24 hours at 20°–27° C. The insoluble matter was filtered off and the filtrate was condensed so as to provide about 500 ml of a solution to precipitate a crystal. The crystal was recovered by filtration and washed with ethanol to obtain 82.2 g of 4-methoxyphenacylamine hydrochloride (Yield: 52.4%).

Step iii) Production of 4-hexylbenzoylaminomethyl 4-methoxyphenyl ketone

To a solution of 26.9 g (120 mM) of 4-hexylbenzoyl chloride in 206 ml of pyridine, 22.2 g (110 mM) of 4-methoxyphenacylamine hydrochloride was gradually added in 30 minutes under cooling and stirring at −10° to −5° C., followed by stirring for 30 minutes below −5° C. and heat-refluxing of 1 hour under stirring. After the reaction, the reaction mixture was cooled to room temperature and poured into 600 ml of cool water to precipitate a crystal. The crystal was recovered by filtration, washed with water and recrystallized from ethanol to obtain 19.6 g of 4-hexylbenzoylaminomethyl-4-methoxyphenylketone (Yield: 50.5%).

Step iv) Production of 2-(4-hexylphenyl)-5-(4-methoxyphenyl)-1,3-thiazole

In a 300 ml-round-bottomed flask, 19.6 g (55.5 mM) of 4-hexylbenzoylaminomethyl-4-methoxyphenyl ketone, 24.3 g (60.1 mM) of Lawesson's reagent and 97 ml of tetrahydrofuran were placed, followed by heat-refluxing for 1 hour under stirring. After the reaction, the reaction mixture was cooled and poured into a solution of 19 g of sodium hydroxide in 2 liters of water to precipitate a crystal. The crystal was recovered by filtration, successively washed with water and recrystallized two times from ethanol to obtain 15.9 g of 2-(4-hexylphenyl)-5-(4-methoxyphenyl)-1,3-thiazole (Yield: 82.9%).

Step v) Production of 2-(4-hexylphenyl)-5-(4-hydroxyphenyl)-1,3-thiazole

In a 300 ml-three-necked flask, 13.9 g (39.3 mM) of 2-(4-hexylphenyl)-5-(4-methoxyphenyl)1,3-thiazole, 76.5 ml of acetic acid and 69.5 ml of 47%-hydrobromic acid were placed, followed by heat-stirring for 16 hours at 100°–110° C. After the reaction, the reaction mixture was poured into cool water, followed by extraction with ethyl acetate. The organic layer was successively washed with water, 5%-sodium hydrogencarbonate aqueous solution and water, followed by drying and distilling-off of the solvent under reduced pressure. The residue was dissolved in a mixture solvent of ethanol/chloroform =1/1, followed by decolorization with activated carbon and distilling-off of the solvent under reduced pressure. The resultant residue was recrystallized two times from toluene to obtain 10.0 g of 2-(4-hexylphenyl)-5-(4-hydroxyphenyl)-1,3-thiazole (Yield: 75.8%).

Step vi) Production of 2-(4-hexylphenyl)-5-[4-(3-trimethylsilylpropoxy)phenyl]-1,3-thiazole 0.34 g (1.0 mM) of 2-(4-hexylphenyl)-5-(4-hydroxyphenyl)-1,3-thiazole, 0.07 g of 85%-KOH and 12 ml of n-butanol were mixed. To the mixture, 0.29 g (1.0 mM) of 3-(trimethylsilyl)propyl p-toluenesulfonate was added dropwise under stirring at 100° C., followed by further stirring for 9 hours at 100° C. After the reaction, the reaction mixture was poured into water and extracted with ethyl acetate, followed by washing with water and drying with anhydrous magnesium sulfate. The magnesium sulfate in the resultant mixture was filtered off and the filtrate was condensed into a solid, followed by purification by silica gel column chromatography (eluent: toluene) and recrystallization from a mixture solvent (ethanol/ethyl acetate) to obtain 0.32 g of 2-(4-hexylphenyl)-5-[4-(3-trimethylsilylpropoxy)phenyl]-1,3-thiazole (Yield: 70.8%).

Phase transition temperature (°C.)

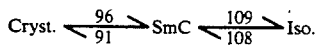

EXAMPLE 7

2-(4-hexylphenyl)-5-[4-(3-butyldimethylsilylpropylcarbonyloxy] -1,3-thiazole (Example Compound No. I-52) was synthesized through the following steps i) and ii).

i)

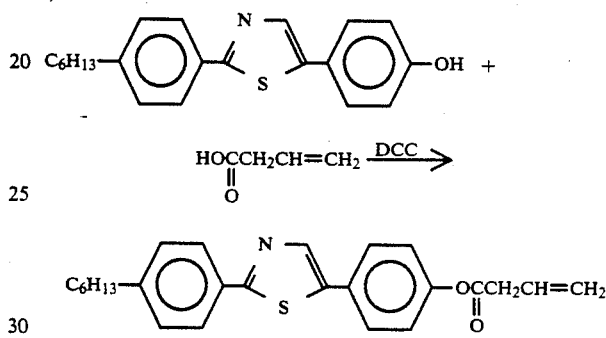

ii)

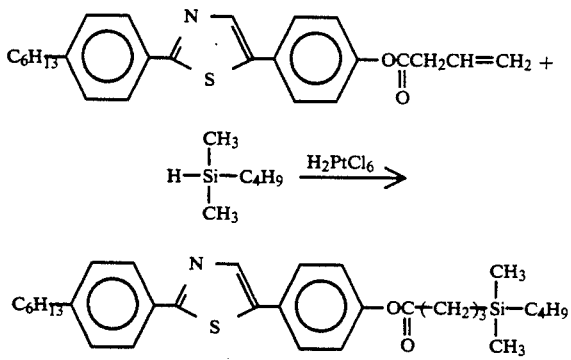

Step i) Production of 2-(4-hexylphenyl)-5-(4-allylcarbonyloxyphenyl)-1,3-thiazole 30 ml of dichloromethane was added to 2.0 g (5.93 mM) of 2-(4-hexylphenyl)-5-(4-hydroxyphenyl)-1,3-thiazole and 0.52 g (6.16 mM) of vinylacetic acid, followed by stirring at room temperature to the mixture, 1.21 g (5.86 mM) of N,N'-dicyclohexylcarbodiimide (DCC) and 0.02 g of 4-pyrrolidinopyridine were added, followed by stirring for 5 hours at room temperature. The resultant dicyclohexylurea was recovered by filtration, followed by washing with dichloromethane to be added to the filtrate. The resultant dichloromethane solution was condensed into a solid under reduced pressure, followed by purification by silica gel column chromatography (eluent: toluene) and recrystallization from a mixture solvent of ethanol/ethyl acetate to obtain 1.93 g of 2-(4-hexylphenyl)-5-(4-allylcarbonyloxyphenyl)-1,3-thiazole (Yield: 81.1%).

Step ii) Production of 2-(4-hexylphenyl)-5-[4-(3-butyldimethylsilylpropylcarbonyloxy)phenyl]-1,3thiazole 2 ml of toluene was added to 0.81 g (1.99 mM) of 2-(4-hexylphenyl)-5-(4-allylcarbonyloxyphenyl)-1,3- thiazole, followed by stirring at room temperature. To the mixture, an appropriate amount chloroplatinic acid, three drops of isopropyl alcohol and 0.24 g (2.06 mM) of butyldimethylsilane were successively added and heated to 80° C., followed by stirring for 7 hours. After the reaction, the reaction mixture was poured into water, followed by extraction with ethyl acetate. The organic layer was washed with water and dried with anhydrous magnesium sulfate. The magnesium sulfate in the resultant organic layer was filtered off, followed by distilling-off of the solvent, purification by silica gel column chromatography (eluent: toluene) and recrystallization from a mixture solvent (methanol/toluene) to obtain 0.25 g of 2-(4-hexylphenyl)-5-[4-(3-butyldimethylsilylpropylcarbonyloxy)phenyl]-1,3-thiazole (Yield: 24.3%).

Phase transition temperature (°C.)

$$\text{Cryst.} \underset{49}{\overset{51}{\rightleftarrows}} \text{SmC} \underset{89}{\overset{90}{\rightleftarrows}} \text{Iso.}$$

EXAMPLE 8

A liquid crystal composition A was prepared by mixing the following compounds in respectively indicated proportions.

| Structural formula | wt. parts |
| --- | --- |
| $C_6H_{13}O$—⟨Ph(N=N)⟩—$C_8H_{17}$ | 54.29 |
| $C_9H_{19}O$—⟨Ph(N=N)⟩—$C_8H_{17}$ | 27.14 |
| $C_8H_{17}O$—⟨Ph(N=N)⟩—$C_{10}H_{21}$ | 13.57 |
| $C_{12}H_{25}$—⟨Ph(N)⟩—⟨Ph⟩—$OCH_2\overset{*}{C}HC_6H_{13}$ (F) | 2.50 |
| $C_{10}H_{21}$—⟨Ph(N)⟩—⟨Ph⟩—$OCH_2\overset{*}{C}HC_6H_{13}$ (F) | 2.50 |

The liquid crystal composition A was further mixed with the following Example Compound No. I-29 in the proportions indicated below to provide a liquid crystal composition B.

| Ex. Comp. No. | Structural formula | wt. parts |
| --- | --- | --- |
| I-29 | $C_6H_{13}$—⟨Ph⟩—CH=CH—(S)—⟨Ph⟩—$O(CH_2)_3Si(CH_3)_2C_4H_9$ | 10 |
| | Composition A | 90 |

The liquid crystal composition B showed the following phase transition series.

Phase transition temperature (°C.)

$$\text{Cryst.} \xrightarrow{10} \text{SmC*} \xrightarrow{46} \text{SmA} \xrightarrow{66} \text{Ch.} \xrightarrow{68} \text{Iso.}$$

Ch.: Chlolesteric phase, and
SmC*: chiral smectic C phase.

EXAMPLE 9

Two 0.7 mm-thick glass plates were provided and respectively coated with an ITO film to form an electrode for voltage application, which was further coated with an insulating layer of vapor-deposited $SiO_2$ On the insulating layer, a 0.2%-solution of silane coupling agent (KBM-602, available from Shinetsu Kagaku K.K.) in isopropyl alcohol was applied by spinner coating at a speed of 2000 rpm for 15 seconds and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After alumina beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 2 microns as measured by a Berek compensator.

Then, the liquid crystal composition B prepared in Example 8 was heated into an isotropic liquid, and injected into the above prepared cell under vacuum and, after sealing, was gradually cooled at a rate of 20° C./hour to 25° C. to prepare a ferroelectric liquid crystal device.

The ferroelectric liquid crystal device was subjected to measurement of the magnitude of spontaneous polarization Ps and an optical response time (time from voltage application until the transmittance change reaches 90% of the maximum under the application of a peak-to-peak voltage Vpp of 20 V in combination with right-angle cross-nicol polarizers).

The results are shown below.

|  | 10° C. | 30° C. |
|---|---|---|
| Response time (μsec) | 421 | 196 |
| Ps (nC/cm$^2$) | 3.17 | 2.20 |

EXAMPLE 10

A liquid crystal composition C was prepared by mixing the following compounds in the respectively indicated proportions.

| Structural formula | wt. parts |
|---|---|
| $C_7H_{15}$–[pyrazine]–[phenyl]–$OC_9H_{19}$ | 12 |
| $C_{11}H_{23}$–[pyrazine]–[phenyl]–$OC_6H_{13}$ | 10 |
| $C_8H_{17}$–[pyrazine]–[phenyl]–$O(CH_2)_5\overset{*}{C}H(CH_3)CH_2C_2H_5$ | 10 |
| $C_{10}H_{21}$–[pyrazine]–[phenyl]–$O(CH_2)_4\overset{*}{C}H(CH_3)OCH_3$ | 3 |
| $C_8H_{17}$–[pyridine]–[phenyl]–[phenyl]–$OC_6H_{13}$ | 8 |
| $C_6H_{13}O$–[phenyl]–OC(O)–[naphthyl]–$OC_9H_{19}$ | 4 |
| $C_3H_7$–[cyclohexyl H]–C(O)O–[phenyl]–[pyrimidine]–$C_{11}H_{23}$ | 6 |
| $C_8H_{17}$–[cyclohexyl H]–C(O)O–[phenyl]–[pyrimidine]–$C_{11}H_{23}$ | 2 |
| $C_5H_{11}$–[cyclohexyl H]–C(O)O–[phenyl]–[pyrimidine]–$C_{11}H_{23}$ | 8 |
| $C_{10}H_{21}O$–[phenyl]–C(O)O–[phenyl]–$OCH_2\overset{*}{C}H(CH_3)C_2H_5$ | 15 |
| $C_4H_9$–[cyclohexyl H]–$CH_2O$–[phenyl]–[pyrimidine]–$C_6H_{13}$ | 7 |

-continued

| Structural formula | wt. parts |
|---|---|
| C5H11—[H]—CH2O—[benzene]—[pyrazine(N,N)]—C6H13 | 7 |
| C9H19O—[benzene]—OCH2—[benzene]—[benzene]—C7H15 | 4 |
| C6H13*CHO—[benzene]—CO—O—[benzene]—[benzene]—OCCH(CH3)OC4H9 (with chiral centers) | 2 |
| C12H25—[pyrazine]—[benzene]—OCCH(Cl)—CHC2H5·CH3 | 2 |

The liquid crystal composition C was further mixed with the following Example Compounds in the proportions indicated below to provide a liquid crystal composition D.

| Ex. Comp. No. | Structural formula | wt. parts |
|---|---|---|
| I-4 | C8H17—[thiophene,S]—CO—O—[benzene]—O—(CH2)3—Si(CH3)(CH3)—C4H9 | 2 |
| I-8 | C6H13—[thiophene,S]—CH2O—[benzene]—O—(CH2)3—Si(CH3)(CH3)—CH3 | 1 |
| I-16 | C6H13—[thiophene,S]—CH2O—[benzene]—[benzene]—OCH2—Si(CH3)(CH3)—C4H9 | 2 |
| | Composition C | 95 |

A ferroelectric liquid crystal device was prepared in the same manner as in Example 9 except for using the composition D. The ferroelectric liquid crystal device was subjected to measurement of response time in the same manner as in Example 9, whereby the following results were obtained.

|  | 10° C. | 25° C. | 40° C. |
|---|---|---|---|
| Response time (μsec) | 684 | 330 | 182 |

COMPARATIVE EXAMPLE 1

A ferroelectric liquid crystal device was prepared in the same manner as in Example 9 except that the liquid crystal composition C prepared in Example 10 was injected into a cell. The measured values of the response time of the device were as follows.

|  | 10° C. | 25° C. | 40° C. |
|---|---|---|---|
| Response time (μsec) | 784 | 373 | 197 |

EXAMPLE 11

A liquid crystal composition E was prepared by mixing the following example compounds in the indicated proportions with the liquid crystal composition C prepared in Example 10.

| Ex. Comp. No. | Structural formula | wt. parts |
|---|---|---|
| I-3 | $C_8H_{17}$—[thiophene]—CO—O—[C$_6$H$_3$F]—OCH$_2$—Si(CH$_3$)$_2$—C$_4$H$_9$ | 2 |
| I-22 | $C_{10}H_{21}$—[thiophene]—[phenyl]—O—(CH$_2$)$_3$—Si(CH$_3$)$_2$—C$_4$H$_9$ | 2 |
| I-24 | $C_{12}H_{25}$—[thiophene]—[C$_6$H$_3$F]—O—(CH$_2$)$_6$—Si(CH$_3$)$_2$—C$_2$H$_5$ | 2 |
| Composition C | | 93 |

A ferroelectric liquid crystal device was prepared in the same manner as in Example 9 except that the above liquid crystal composition E was used, and the device was subjected to measurement of optical response time. The results of the measurement are shown below.

|  | 10° C. | 25° C. | 40° C. |
|---|---|---|---|
| Response time (μsec) | 648 | 315 | 175 |

EXAMPLE 12

A liquid crystal composition F was prepared by mixing the following example compounds in the indicated proportions with the liquid crystal composition C prepared in Example 10.

A ferroelectric liquid crystal device was prepared in the same manner as in Example 9 except that the above liquid crystal composition F was used, and the device was subjected to measurement of optical response time. The results of the measurement are shown below.

|  | 10° C. | 25° C. | 40° C. |
|---|---|---|---|
| Response time (μsec) | 705 | 339 | 185 |

EXAMPLE 12

A liquid crystal composition G was prepared by mixing the following compounds in the respectively indicated proportions.

| Ex. Comp. No. | Structural formula | wt. parts |
|---|---|---|
| I-26 | $C_{10}H_{21}$—[thiophene]—[C$_6$H$_3$F]—O—CO—(CH$_2$)$_3$—Si(CH$_3$)$_2$—C$_4$H$_9$ | 2 |
| I-29 | $C_6H_{13}$—[phenyl]—[thiophene]—[phenyl]—O—(CH$_2$)$_3$—Si(CH$_3$)$_2$—C$_4$H$_9$ | 1 |
| I-34 | $C_6H_{13}$—[phenyl]—[thiophene]—[C$_6$H$_3$F]—O—(CH$_2$)$_3$—Si(CH$_3$)$_2$—C$_4$H$_9$ | 1 |
| I-35 | $C_6H_{13}$—[phenyl]—[thiophene]—[C$_6$H$_3$F]—O—CO—(CH$_2$)$_4$—Si(CH$_3$)$_2$—C$_2$H$_5$ | 1 |
| Composition C | | 95 |

| Structural formula | wt. parts |
|---|---|
| 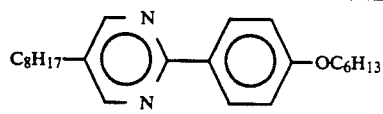 | 10 |
| 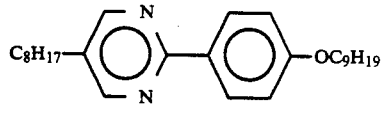 | 5 |
| 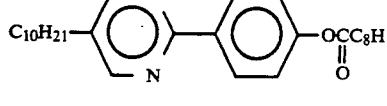 | 7 |
| 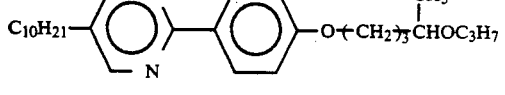 | 7 |
|  | 6 |
| 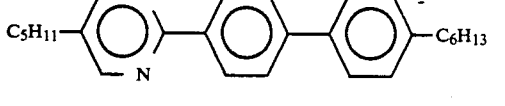 | 5 |
| 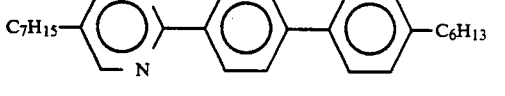 | 5 |
| 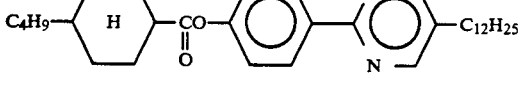 | 8 |
| 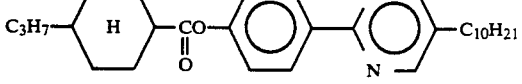 | 8 |
| 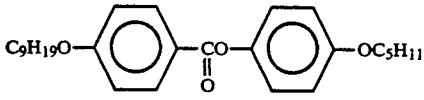 | 20 |
| 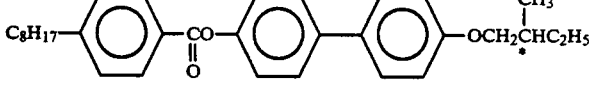 | 5 |
| 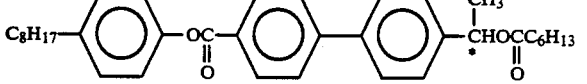 | 5 |
| 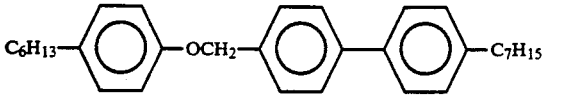 | 6 |

| Structural formula | wt. parts |
|---|---|
|  C$_{12}$H$_{25}$—[pyrimidine]—[phenyl]—OCH$_2$CHC$_6$H$_{13}$ (F, *) | 3 |

The liquid crystal composition G was further mixed with the following Example Compounds in the proportions indicated below to provide a liquid crystal composition H.

| Ex. Comp. No. | Structural formula | wt. parts |
|---|---|---|
| I-23 | C$_{10}$H$_{21}$—[thiophene]—CH=CH—[phenyl]—OC(=O)(CH$_2$)$_4$Si(CH$_3$)(CH$_3$)—C$_4$H$_9$ | 2 |
| I-43 | C$_{10}$H$_{21}$—[thiazole]—CH=CH—[phenyl(F)]—O(CH$_2$)$_6$Si(CH$_3$)(CH$_3$)—C$_6$H$_{13}$ | 1 |
| I-57 | C$_6$H$_{13}$CHCH$_2$O(F, *)—[phenyl]—[thiazole]—CH=CH—[phenyl]—O(CH$_2$)$_3$Si(CH$_3$)(CH$_3$)—C$_4$H$_9$ | 2 |
| Composition G | | 95 |

A ferroelectric liquid crystal device was prepared in the same manner as in Example 9 except that the above liquid crystal composition H was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 518 | 259 | 137 |

Further, when the device was driven, a clear switching action was observed, and good bistability was shown after the termination of the voltage application.

COMPARATIVE EXAMPLE 2

A ferroelectric liquid crystal device was prepared in the same manner as in Example 9 except that the liquid crystal composition G prepared in Example 13 was injected into a cell. The measured values of the response time of the device were as follows.

| | 10° C. | 25° C. | 40° C. |
|---|---|---|---|
| Response time (μsec) | 653 | 317 | 159 |

EXAMPLE 14

A liquid crystal composition I was prepared by mixing the following example compounds in the indicated proportions with the liquid crystal composition G prepared in Example 13.

| Ex. Comp. No. | Structural formula | wt. parts |
|---|---|---|
| I-51 | C$_6$H$_{13}$—[phenyl]—[thiazole]—CH=CH—[phenyl]—O(CH$_2$)$_3$Si(CH$_3$)(CH$_3$)—CH$_3$ | 2 |
| I-52 | C$_6$H$_{13}$—[phenyl]—[thiazole]—CH=CH—[phenyl]—OC(=O)(CH$_2$)$_3$Si(CH$_3$)(CH$_3$)—C$_4$H$_9$ | 2 |
| I-68 | C$_6$H$_{13}$CHCH$_2$O(F, *)—[phenyl]—[thiazole]—CH=CH—[phenyl]—O—CH$_2$Si(CH$_3$)(CH$_3$)—C$_2$H$_5$ | 1 |

| Ex. Comp. No. | Structural formula | wt. parts |
|---|---|---|
| | Composition G | 95 |

A ferroelectric liquid crystal device was prepared in the same manner as in Example 9 except that the above liquid crystal composition I was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 547 | 268 | 141 |

A ferroelectric liquid crystal device was prepared in the same manner as in Example 9 except that the above liquid crystal composition J was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 560 | 277 | 146 |

EXAMPLE 15

A liquid crystal composition J was prepared by mixing the following example compounds in the indicated proportions with the liquid crystal composition G prepared in Example 13.

EXAMPLE 14

A liquid crystal composition K was prepared by mixing the following compounds in the respectively indicated proportions.

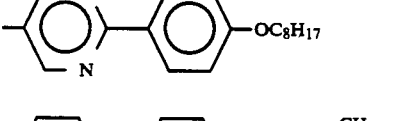

-continued
| Structural formula | wt. parts |
|---|---|
| 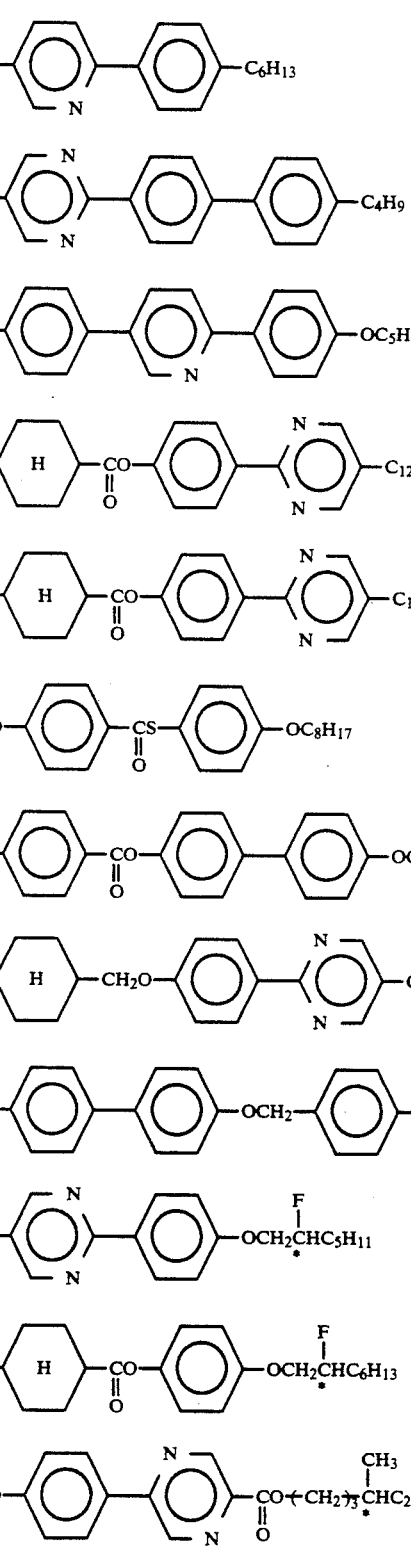 | 14 |
| 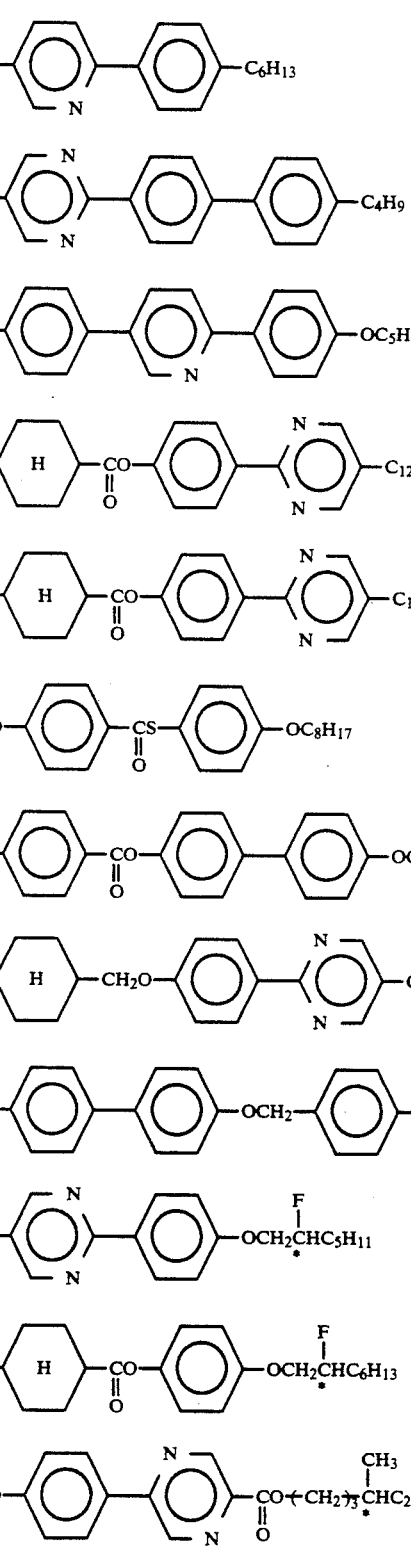 | 8 |
| 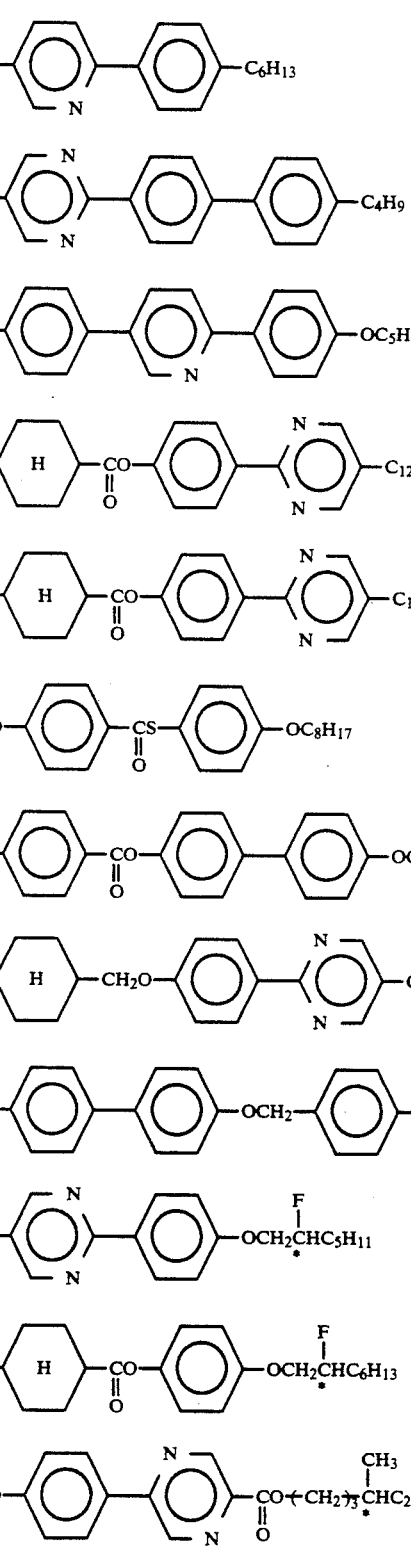 | 4 |
| 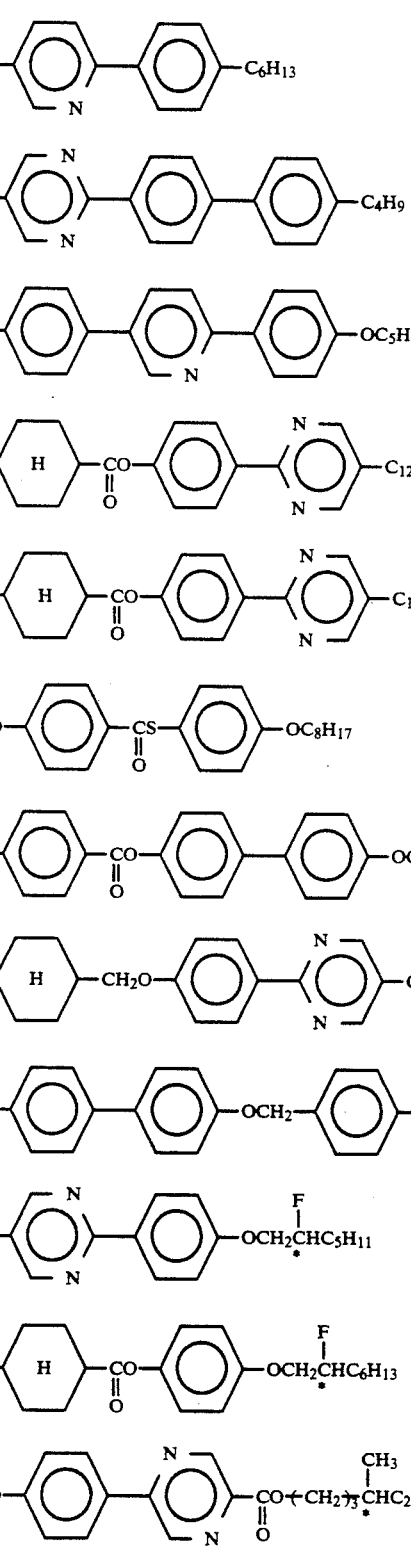 | 2 |
| 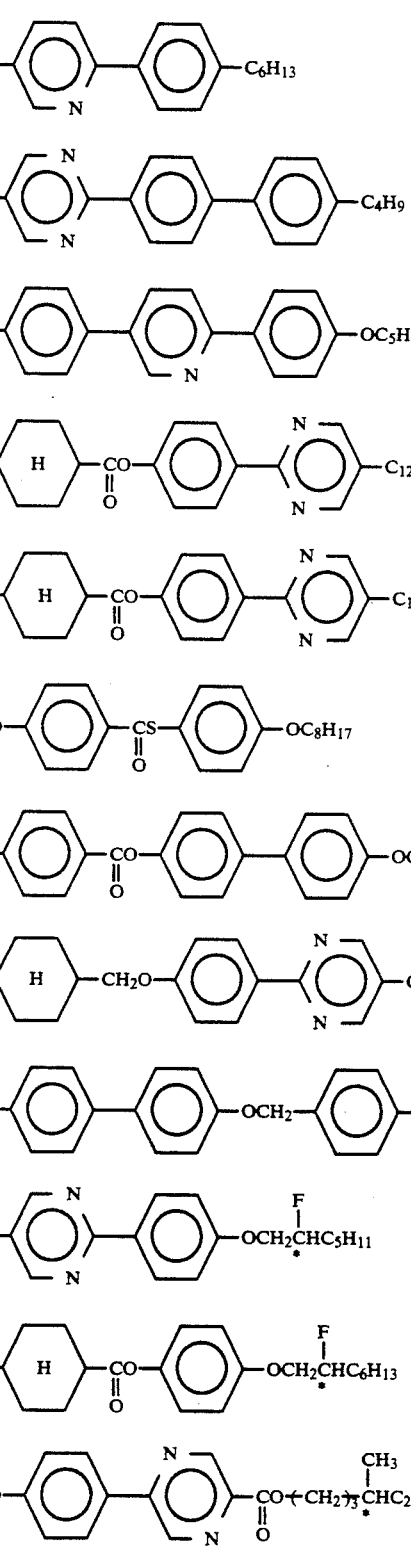 | 10 |
| 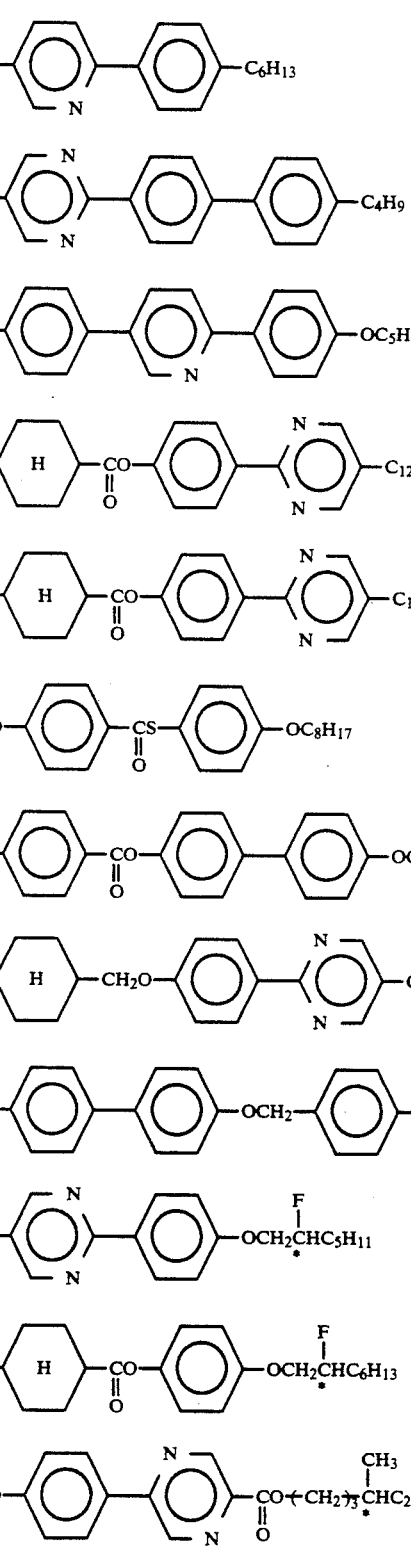 | 5 |
| 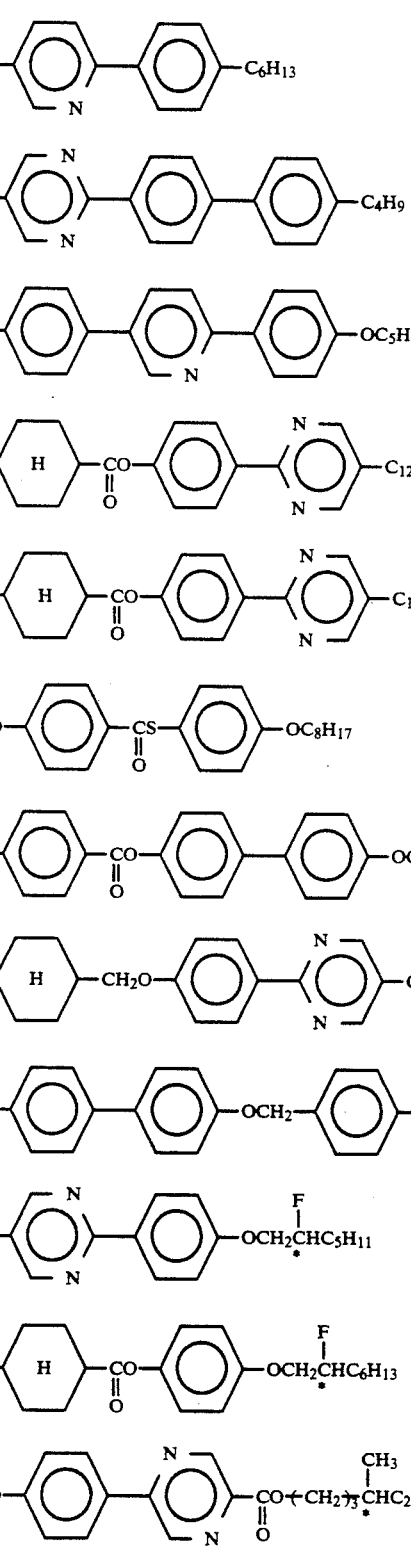 | 10 |
| 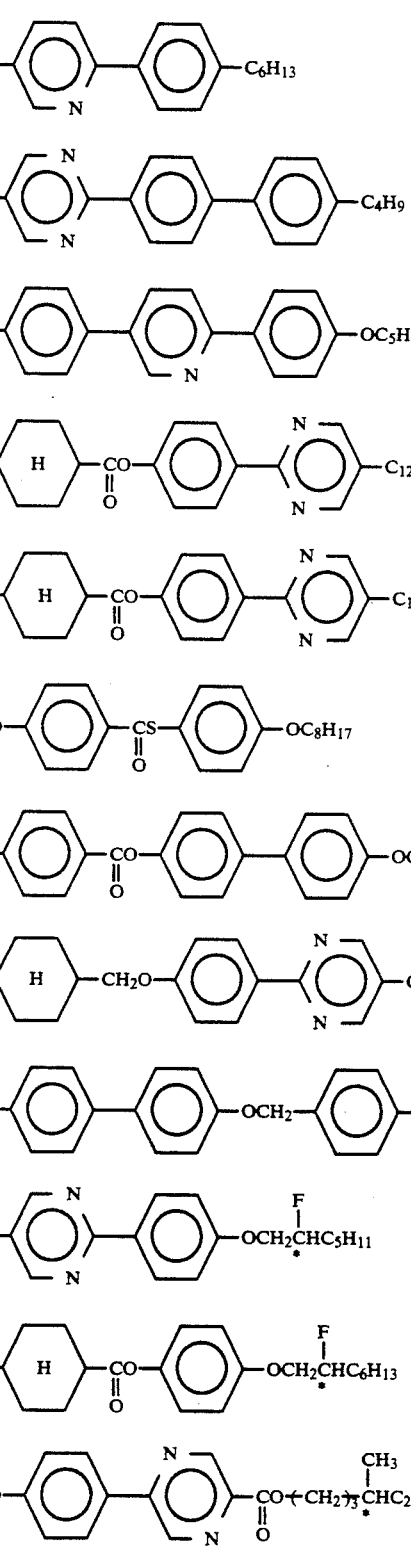 | 7 |
| 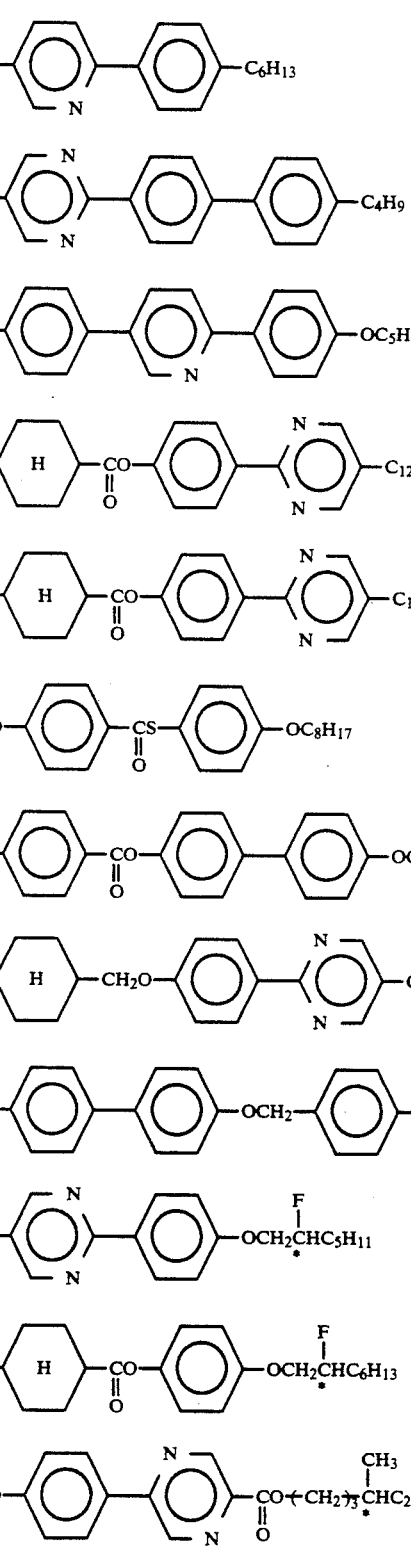 | 7 |
| 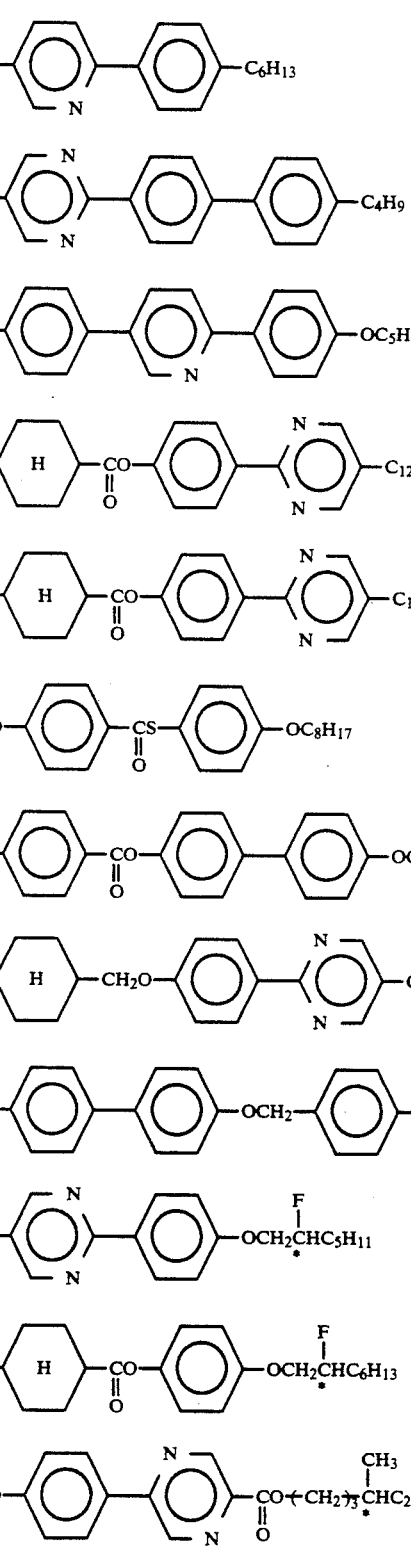 | 5 |
| 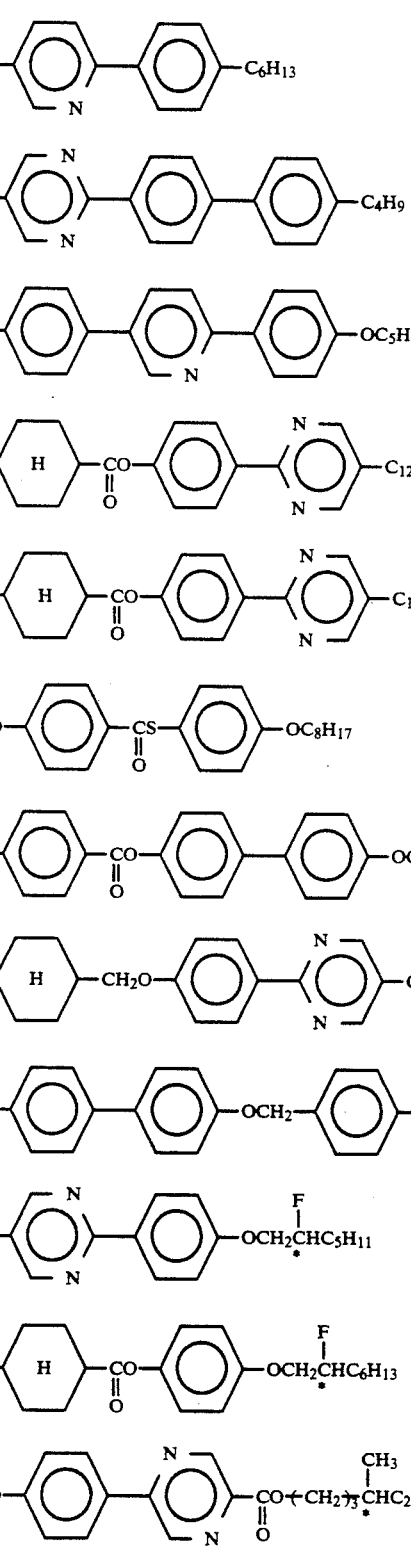 | 2 |
| 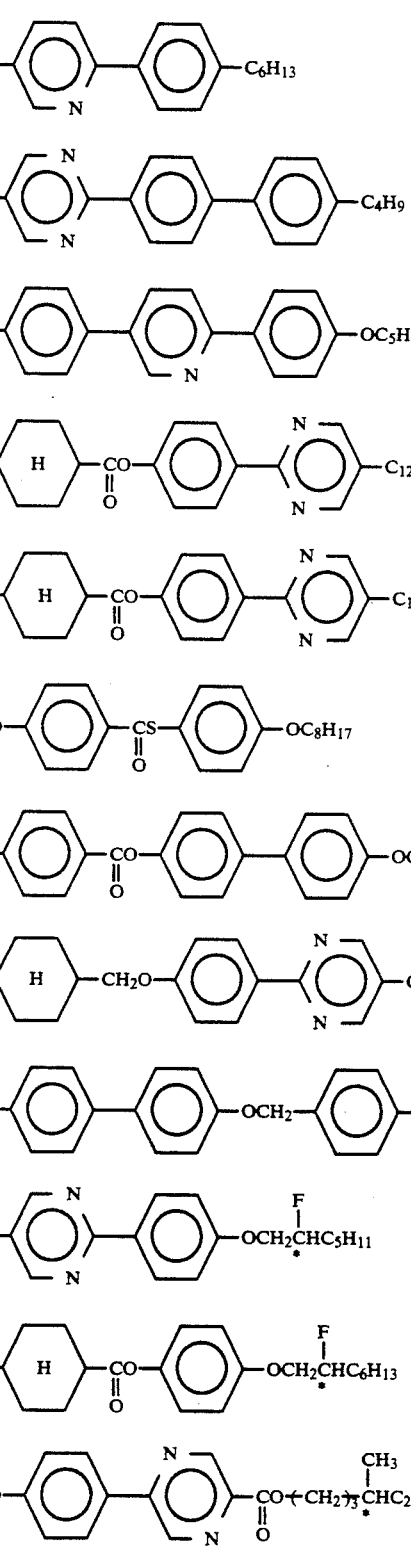 | 2 |
| 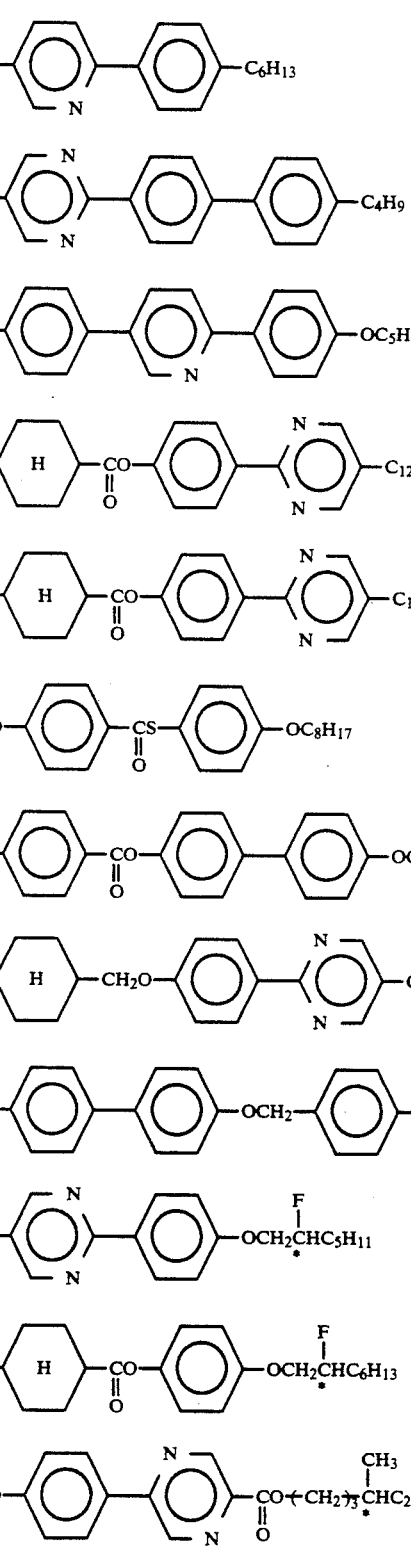 | 2 |

| Structural formula | wt. parts |
|---|---|
| $C_{12}H_{25}O-\phenyl-\pyridyl-O(CH_2)_3CHOC_3H_7$ with $CH_3$ branch | 3 |

The liquid crystal composition K was further mixed with the following Example Compounds in the proportions indicated below to provide a liquid crystal composition L.

| Ex. Comp. No. | Structural formula | wt. parts |
|---|---|---|
| I-10 | $C_6H_{13}-S-\text{=}-CO-O-\phenyl-\phenyl-O-CO(CH_2)_3Si(CH_3)_2-C_4H_9$ | 2 |
| I-88 | $C_8H_{17}-S-\text{=}-\phenyl-OCO-\phenyl-O(CH_2)_6Si(CH_3)_2-C_6H_{13}$ | 2 |
| I-93 | $C_6H_{13}-S-\text{=}-\phenyl-OCH_2-\phenyl-O(CH_2)_6Si(CH_3)_2-CH_{13}$ | 1 |
| Composition K | | 95 |

A ferroelectric liquid crystal device was prepared in the same manner as in Example 9 except that the above liquid crystal composition L was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 600 | 314 | 175 |

COMPARATIVE EXAMPLE 3

A ferroelectric liquid crystal device was prepared in the same manner as in Example 9 except that the liquid crystal composition K prepared in Example 16 was injected into a cell. The measured values of the response time of the device were as follows.

| | 10° C. | 25° C. | 40° C. |
|---|---|---|---|
| Response time (μsec) | 668 | 340 | 182 |

EXAMPLE 17

A liquid crystal composition M was prepared by mixing the following example compounds in the indicated proportions with the liquid crystal composition K prepared in Example 16.

| Ex. Comp. No. | Structural formula | wt. parts |
|---|---|---|
| I-42 | $C_{10}H_{21}-S-\text{=}-\phenyl-O(CH_2)_3Si(CH_3)_2-C_4H_9$ | 2 |
| I-86 | $C_6H_{13}-S-\text{=}-\phenyl-OCO-\phenyl-O(CH_2)_3Si(CH_3)_2-C_4H_9$ | 1 |
| I-97 | $C_{12}H_{25}-S-\text{=}-\phenyl-CH_2O-\phenyl-O(CH_2)_3Si(CH_3)_2-C_4H_9$ | 1 |
| Composition K | | 96 |

A ferroelectric liquid crystal device was prepared in the same manner as in Example 9 except that the above liquid crystal composition M was used, and the device was subjected to measurement of optical response time and observation of switching states. In the device, a monodomain with a good and uniform alignment characteristic was observed. The results of the measurement are shown below.

|  | 10° C. | 25° C. | 40° C. |
| --- | --- | --- | --- |
| Response time (μsec) | 548 | 287 | 163 |

EXAMPLE 18

A liquid crystal composition N was prepared by mixing the following example compounds in the indicated proportions with the liquid crystal composition K prepared in Example 16.

| Ex. Comp. No. | Structural formula | wt. parts |
| --- | --- | --- |
| I-92 | $C_{10}H_{21}-\overset{}{\underset{S}{\diagup\diagdown}}-\langle\bigcirc\rangle(F)-O\overset{O}{\underset{\parallel}{C}}-\langle\bigcirc\rangle-O(CH_2)_3-Si(CH_3)(C_2H_5)-CH_3$ | 1 |
| I-99 | $C_6H_{13}-\overset{N}{\underset{S}{\diagup\diagdown}}-\langle\bigcirc\rangle-O\overset{O}{\underset{\parallel}{C}}-\langle\bigcirc\rangle-O(CH_2)_3-Si(CH_3)_3$ | 1 |
| I-105 | $C_6H_{13}-\overset{N}{\underset{S}{\diagup\diagdown}}-\langle\bigcirc\rangle-OCH_2-\langle\bigcirc\rangle-O(CH_2)_8-Si(CH_3)_3$ | 1 |
| I-108 | $C_{10}H_{21}-\overset{N}{\underset{S}{\diagup\diagdown}}-\langle\bigcirc\rangle-CH_2O-\langle\bigcirc\rangle-O(CH_2)_3-Si(CH_3)(C_2H_5)-CH_3$ | 1 |
| Composition K | | 96 |

A ferroelectric liquid crystal device was prepared in the same manner as in Example 9 except that the above liquid crystal composition N was used, and the device was subjected to measurement of optical response time and observation of switching states. In the device, a monodomain with a good and uniform alignment characteristic was observed. The results of the measurement are shown below.

|  | 10° C. | 25° C. | 40° C. |
| --- | --- | --- | --- |
| Response time (μsec) | 578 | 301 | 170 |

As is apparent from the results shown in the above Examples 10–18, the ferroelectric liquid crystal devices containing the liquid crystal compositions D, E, F, H, I, J, L, M and N showed an improved low-temperature operation characteristic, a high-speed responsiveness, and a decreased temperature dependence of the response speed.

EXAMPLE 19

A blank cell was prepared in the same manner as in Example 10 by using a 2% aqueous solution of polyvinyl alcohol resin (PVA-117, available from Kuraray K.K.) instead of the 1.5% solution of polyimide resin precursor in dimethylacetoamide on each electrode plate. A ferroelectric liquid crystal device was prepared by filling the blank cell with the liquid crystal composition D prepared in Example 10. The liquid crystal device was subjected to measurement of optical response time in the same manner as in Example 9. The results are shown below.

|  | 10° C. | 25° C. | 40° C. |
| --- | --- | --- | --- |
| Response time (μsec) | 681 | 332 | 183 |

EXAMPLE 20

A blank cell was prepared in the same manner as in Example 10 except for omitting the SiO₂ layer to form an alignment control layer composed of the polyimide resin layer along on each electrode plate. A ferroelectric liquid crystal device was prepared by filling the blank cell with the liquid crystal composition D prepared in Example 10. The liquid crystal device was subjected to measurement of optical response time in the same manner as in Example 9. The results are shown below.

|  | 10° C. | 25° C. | 40° C. |
| --- | --- | --- | --- |
| Response time (μsec) | 679 | 329 | 181 |

As is apparent from the above Examples 19 and 20, also in the cases of different device structures, the devices containing the ferroelectric liquid crystal composition D according to the present invention respectively provided a remarkably improved operation characteristic at a lower temperature and also a decreased temperature-dependence of the response speed similar to those in Example 10.

As described hereinabove, according to the present invention, there is provided a mesomorphic compound which can effectively be applied to a liquid crystal device utilizing ferroelectricity when the compound per se assumes a chiral smectic phase. Further, there is also provided a liquid crystal composition containing the compound and having a chiral smectic phase, whereby a liquid crystal device comprising the composition can be operated by utilizing ferroelectricity of the composition. The present invention provides a liquid crystal device using such a composition which shows a good switching characteristic, am improved low-temperature operation characteristic and a decreased temperature-dependence of response speed. The present invention further provides a display apparatus and a display method which employ such a device as a display unit, whereby good display characteristics can be obtained in combination with a light source, a drive circuit, etc.

What is claimed is:

1. A mesomorphic compound represented by the following formula (I):

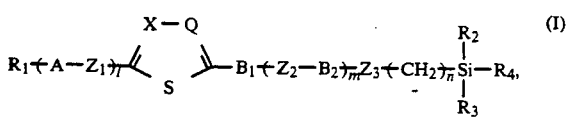

wherein $R_1$ denotes a linear or branched alkyl group having 2-16 carbon atoms capable of including one or non-neighboring two methylene groups which can be replaced with —O—, —S—, —CO—, —COO— or —OCO— and capable of including a hydrogen atom which can be replaced with a fluorine atom; A denotes —$A_1$— or —$A_1$—$a_2$: $B_2$ denotes —$B_3$— or —$B_3$—$B_4$—; $A_1$, $A_2$, $B_1$, $B_3$ and $B_4$ independently denote

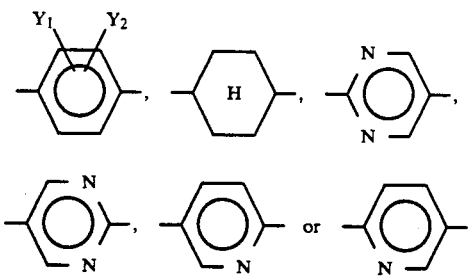

wherein $Y_1$ and $Y_2$ independently denote a hydrogen atom, F, Cl, Br, —$CH_3$, —CN or —$CF_3$, with the proviso that $B_1$ can be a single bond; $A_1$-$A_2$ and $B_1$-$B_3$-$B_4$— can not have a nitrogen-containing ring next to each other $Z_1$ and $Z_2$ independently denote a single bond, —COO—, —OCO—, —$CH_2O$— or —$OCH_2$—; $Z_3$ denotes —O—, —CO—, —COO— or —OCO—; $R_2$, $R_3$ and $R_4$ independently denote a linear or branched alkyl group having 1-16 carbon atoms capable of including one or two methylene groups, other than those directly connected to Si, which can be replaced with —O—, —COO— or —OCO— with the proviso that —O— cannot directly be connected to —O—; l and m independently denote 0 or 1 with the proviso that l+m≠0; n is an integer of 1-12; and X and Q independently denote CH or N with the proviso that X and Q cannot be N simultaneously.

2. A mesomorphic compound according to claim 1, wherein $R_1$ denotes any one of alkyl, alkoxy, alkanoyloxy and alkoxycarbonyl groups.

3. A mesomorphic compound according to claim 1, wherein $A_1$, $A_2$, $B_1$, $B_3$ and $B_4$ independently denote

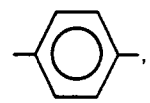

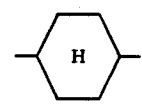

or

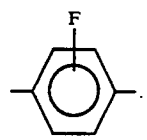

4. A mesomorphic compound according to claim 1, wherein at least two groups of $R_2$, $R_3$ and $R_4$ are methyl groups.

5. A liquid crystal composition comprising at least two mesomorphic compounds, at least one of which is a mesomorphic compound of the formula (I) according to claim 1.

6. A liquid crystal composition according to claim 5, wherein $R_1$ in the formula (I) denotes any one of alkyl, alkoxy, alkanoyloxy and alkoxycarbonyl groups.

7. A liquid crystal composition according to claim 5, wherein $A_1$, $A_2$, $B_1$, $B_3$ and $B_4$ in the formula (I) independently denote

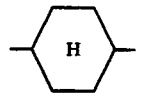

or

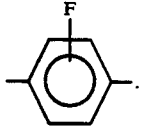

8. A liquid crystal composition according to claim 5, wherein at least two groups of $R_2$, $R_3$ and $R_4$ in the formula (I) are methyl groups.

9. A liquid crystal composition according to claim 5, which has a chiral smectic phase.

10. A liquid crystal composition according to claim 5, which comprises 1-80 wt. % of a mesomorphic compound of the formula (I).

11. A liquid crystal composition according to claim 5, which comprises 1-60 wt. % of a mesomorphic compound of the formula (I).

12. A liquid crystal composition according to claim 5, which comprises 1-40 wt. % of a mesomorphic compound of the formula (I).

13. A liquid crystal device, comprising a pair of electrode plates and a liquid crystal composition according to claim 5 disposed between the electrode plates.

14. A liquid crystal device according to claim 13, wherein $R_1$ in the formula (I) denotes any one of alkyl, alkoxy, alkanoyloxy and alkoxycarbonyl groups.

15. A liquid crystal device according to claim 13, wherein $A_1$, $A_2$, $B_1$, $B_3$ and $B_4$ in the formula (I) independently denote

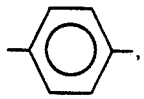

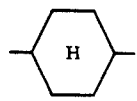

or

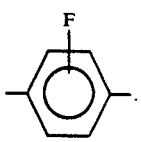

16. A liquid crystal device according to claim 13, wherein at least two groups of $R_2$, $R_3$ and $R_4$ in the formula (I) are methyl groups.

17. A liquid crystal device according to claim 13, wherein the liquid crystal composition has a chiral smectic phase.

18. A liquid crystal device according to claim 13, wherein the liquid crystal composition comprises 1-80 wt. % of a mesomorphic compound of the formula (I).

19. A liquid crystal device according to claim 13, wherein the liquid crystal composition comprises 1-60 wt. % of a mesomorphic compound of the formula (I).

20. A liquid crystal device according to claim 13, wherein the liquid crystal composition comprises 1-40 wt. % of a mesomorphic compound of the formula (I).

21. A liquid crystal device according to claim 13, which further comprises an insulating alignment control layer.

22. A liquid crystal device according to claim 21, wherein the insulating alignment control layer has been subjected to rubbing.

23. A display apparatus comprising a liquid crystal device according to claim 13, and voltage application means for driving the liquid crystal device.

24. A display apparatus according to claim 23, wherein $R_1$ in the formula (I) denotes any one of alkyl, alkoxy, alkanoyloxy and alkoxycarbonyl groups.

25. A display apparatus according to claim 23, wherein $A_1$, $A_2$, $B_1$, $B_3$ and $B_4$ in the formula (I) independently denote

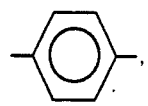

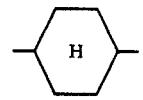

or

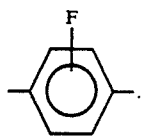

26. A display apparatus according to claim 23, wherein at least two groups of $R_2$, $R_3$ and $R_4$ in the formula (I) are methyl groups.

27. A display apparatus according to claim 23, which further comprises a drive circuit.

28. A display apparatus according to claim 23, which further comprises a light source.

29. A display method, comprising:
providing a liquid crystal composition comprising at least two mesomorphic compound, at least one of which is a mesomorphic compound of the formula (I) according to claim 1; and
switching the alignment direction of liquid crystal molecules by applying voltages to the liquid crystal composition to effect display.

30. A display method according to claim 29, wherein $R_1$ in the formula (I) denotes any one of alkyl, alkoxy, alkanoyloxy and alkoxycarbonyl groups.

31. A display method according to claim 29, wherein $A_1$, $A_2$, $B_1$, $B_3$ and $B_4$ in the formula (I) independently denote

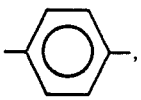

or

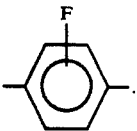

32. A display method according to claim 29, wherein at least two groups of $R_2$, $R_3$ and $R_4$ in the formula (I) are methyl groups.

33. A display method according to claim 29, wherein the liquid crystal composition has a chiral smectic phase.

34. A display method according to claim 29, wherein the liquid crystal composition comprises 1-80 wt. % of a mesomorphic compound of the formula (I).

35. A display method according to claim 29, wherein the liquid crystal composition comprises 1-60 wt. % of a mesomorphic compound of the formula (I).

36. A display method according to claim 29, wherein the liquid crystal composition comprises 1-40 wt. % of a mesomorphic compound of the formula (I).

37. A display method, comprising:

providing a liquid crystal device comprising a pair of electrode plates and a liquid crystal composition disposed therebetween comprising at least two mesomorphic compound, at least one of which is a mesomorphic compound of the formula (I) according to claim 1; and switching the alignment direction of liquid crystal molecules by applying voltages to the liquid crystal composition disposed between the electrode plates to effect display.

38. A display method according to claim 37, wherein $R_1$ in the formula (I) denotes any one of alkyl, alkoxy, alkanoyloxy and alkoxycarbonyl groups.

39. A display method according to claim 37, wherein $A_1$, $A_2$, $B_1$, $B_3$ and $B_4$ in the formula (I) independently denote

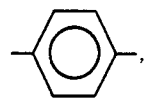

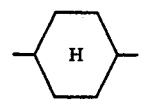

or

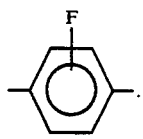

40. A display method according to claim 37, wherein at least two groups of $R_2$, $R_3$ and $R_4$ in the formula (I) are methyl groups.

* * * * *

UNITED STATES PATENT AND TRADEMARK OFFICE
CERTIFICATE OF CORRECTION

PATENT NO. : 5,217,645
DATED : June 8, 1993
INVENTOR(S) : TAKASHI IWAKI, ET AL.

It is certified that error appears in the above-identified patent and that said Letters Patent is hereby corrected as shown below:

COLUMN 1

Line 52, "halfselected" should read --half-selected--.

COLUMN 3

Line 50, "$-A_1-A_2;$" should read -- $-A_1-A_2-;$ --.

COLUMN 6

Line 14, "m = 1)" should read --m = 0)--.

COLUMN 17

Formula (I-68), "
$\begin{array}{c} F \\ | \\ C_6H_{13}CHCH_2O \end{array}$
" should read --
$\begin{array}{c} F \\ | \\ C_6H_{13}CHCH_2O \\ * \end{array}$
-- and "$-O-CH_2$" should read --  --.

COLUMN 38

Line 52, "0 to 1" should read --0 or 1--.

COLUMN 56

Line 18, "4-3-butyldimethylsilyl)propox-" should read --4-[3-(butyldimethylsilyl)propox- --.

UNITED STATES PATENT AND TRADEMARK OFFICE
CERTIFICATE OF CORRECTION

PATENT NO. : 5,217,645

DATED : June 8, 1993

INVENTOR(S) : TAKASHI IWAKI, ET AL.

It is certified that error appears in the above-identified patent and that said Letters Patent is hereby corrected as shown below:

COLUMN 58

Line 20, "-(p-methoxybenzoyl)acrylic" should read
--ß-(p-methoxybenzoyl)acrylic--.
Line 39, "1-(  ethoxyphenyl)" should read
--1-(4-methoxyphenyl)--.
Line 40, "(1.90  0-1 M)" should read --(1.90×10⁻¹ M)--.
Line 48, "(1.52×10-1 M)" should read --(1.52×10⁻¹ M)--.

COLUMN 60

Line 10, "09.0 g" should read --90.0 g--.
Line 32, "1,4-butane" should be deleted.
Line 58, "3-butyldimethylsilyl)propyl" should read
--3-(butyldimethylsilyl)propyl--.

COLUMN 61

Line 2, "(Yield: 70/1%)." should read --Yield: 70.1%).--.

COLUMN 62

Line 33, "(3-fluoro4-" should read --(3-fluoro-4- --.
Line 36, "methoxyphenyl)1,4-" should read
--methoxyphenyl)-1,4- --.
Line 43, "(3-fluoro4-" should read --(3-fluoro-4- --.

COLUMN 63

Line 7, "butyldimethylsilylpropoxy)" should read
--butyldimethylsilyl-propoxy)--.
Line 20, "(3-trimethylsilylpropoxy)-" should read
--(3-trimethylsilyl-propoxy)- --.

UNITED STATES PATENT AND TRADEMARK OFFICE
CERTIFICATE OF CORRECTION

PATENT NO. : 5,217,645
DATED : June 8, 1993
INVENTOR(S) : TAKASHI IWAKI, ET AL.

It is certified that error appears in the above-identified patent and that said Letters Patent is hereby corrected as shown below:

COLUMN 66

Line 52, "to the mixture," should read --. Thereafter,--.
Line 54, "were added," should read --were added to the mixture,--.
Line 66, "1,3thiazole" should read --1,3-thiazole--.

COLUMN 67

Line 2, "amount" should read --amount of--.

COLUMN 68

Line 31, "$SiO_2$ On" should read --$SiO_2$. On--.

COLUMN 87

Line 38, "$-A_1-a_2$:" should read -- $-A_1-A_2-$;--.
Line 55, "bond; $-A_1-A_2$" should read --bond, $-A_1-A_2$--.
Line 57, "other $Z_1$" should read --other; $Z_1$--.

COLUMN 90

Line 29, "compound" should read --compounds--.

UNITED STATES PATENT AND TRADEMARK OFFICE
CERTIFICATE OF CORRECTION

PATENT NO. : 5,217,645

DATED : June 8, 1993

INVENTOR(S) : TAKASHI IWAKI, ET AL.

It is certified that error appears in the above-identified patent and that said Letters Patent is hereby corrected as shown below:

COLUMN 91

Line 14, "compound" should read --compounds--.

Signed and Sealed this

Twenty-sixth Day of April, 1994

Attest:

BRUCE LEHMAN

Attesting Officer     Commissioner of Patents and Trademarks